(12) United States Patent
Faupel et al.

(10) Patent No.: US 6,975,899 B2
(45) Date of Patent: Dec. 13, 2005

(54) MULTI-MODAL OPTICAL TISSUE DIAGNOSTIC SYSTEM

(75) Inventors: Mark L. Faupel, Alpharetta, GA (US); Shabbir B. Bambot, Suwanee, GA (US); Tim Harrell, Norcross, GA (US); Anant Agrawal, Atlanta, GA (US)

(73) Assignee: SpectRx, Inc., Norcross, GA (US)

( * ) Notice: Subject to any disclaimer, the term of this patent is extended or adjusted under 35 U.S.C. 154(b) by 0 days.

(21) Appl. No.: 10/603,597

(22) Filed: Jun. 26, 2003

(65) Prior Publication Data

US 2004/0010197 A1 Jan. 15, 2004

Related U.S. Application Data

(63) Continuation of application No. 09/786,781, filed as application No. PCT/US99/20646 on Sep. 10, 1999, now abandoned.
(60) Provisional application No. 60/099,875, filed on Sep. 11, 1998, and provisional application No. 60/143,579, filed on Jul. 13, 1999.

(51) Int. Cl.$^7$ .................................................. A61B 6/00
(52) U.S. Cl. .................... 600/476; 600/473; 600/477; 600/407; 606/15; 606/16; 607/89
(58) Field of Search ................................ 600/476, 473, 600/474, 475, 477, 478, 479, 480, 310, 316, 342, 431, 407, 178; 607/89, 72; 606/2, 15, 16; 436/171, 172

(56) References Cited

U.S. PATENT DOCUMENTS

| | | |
|---|---|---|
| 3,494,354 A | 2/1970 | Yokota et al. |
| 4,056,724 A | 11/1977 | Harte |
| 4,071,020 A | 1/1978 | Pugliese |

(Continued)

FOREIGN PATENT DOCUMENTS

| | | |
|---|---|---|
| WO | WO 98/46133 | 10/1998 |
| WO | WO 99/57529 | 11/1999 |
| WO | WO00/15101 | 3/2000 |

OTHER PUBLICATIONS

Shabbir B. Bambot et al., "Sensing oxygen through skin using a red diode laser and fluorescence liftetimes", Biosens and Bioelectronics, vol. 10, Nov. 6/7, pp 643–652, 1995.

Kevin T. Shoemacher et al., "Ultraviolet Laser–Induced Fluorescence of Colonic Tissues: Basic Biology and Diagnostic Potential", Laser in Surgery Medicine, vol. 12, pp 63–78, 1992.

Charles E. Alpers et al., "The Prevalence of Carcinoma in Situ In Normal and Cancer Associated Breasts," Human Pathology, vol. 16, No. 8, pp. 796–807, Aug. 1985.

Danely Slaughter et al., Field Cancerization in Oral Stratified Squamous Epithelium: Clinical Implication of Multicentric Origin Cancer, vol. 6, pp. 963–968, 1952.

Cancer Diagnotistics, The World Market, Clinical Reports, PJB Publications, p. 72, 1997.

Fuchs et al., "Combined fluorescene and reflectance spectroscopy: in vivo assessment of oral cavity epithelial neoplasia", Technical Digest. Summaries of Papers Presented at the Conference of Lasers and Electro–Optics. Conference Edition. 1998, vol. 6 (IEEE Cat No. 98CH36178) pp 306–307, XP002283180 1998, Wash, DC, USA, Opt. Soc. America, USA ISBN: 1–55752–339–0.

*Primary Examiner*—Fadi H. Dahbour
(74) *Attorney, Agent, or Firm*—Fleshner & Kim, LLP

(57) ABSTRACT

An apparatus and method according to the invention combine more than one optical modality (spectroscopic method), including but not limited to fluorescence, absorption, reflectance, polarization anisotropy, and phase modulation, to decouple morphological and biochemical changes associated with tissue changes due to disease, and thus to provide an accurate diagnosis of the tissue condition.

45 Claims, 53 Drawing Sheets

U.S. PATENT DOCUMENTS

| | | |
|---|---|---|
| 4,084,905 A | 4/1978 | Schreiber et al. |
| 4,099,872 A | 7/1978 | White |
| 4,115,699 A | 9/1978 | Mizuta et al. |
| 4,122,348 A | 10/1978 | Bruck |
| 4,125,828 A | 11/1978 | Resnick et al. |
| 4,127,773 A | 11/1978 | West |
| 4,131,800 A | 12/1978 | Bruck et al. |
| 4,144,452 A | 3/1979 | Harte |
| 4,160,016 A | 7/1979 | Ullman |
| 4,161,515 A | 7/1979 | Ullman |
| 4,162,405 A | 7/1979 | Chance et al. |
| 4,203,670 A | 5/1980 | Bromberg |
| 4,213,742 A | 7/1980 | Sato |
| 4,223,680 A | 9/1980 | Jobsis |
| 4,236,526 A | 12/1980 | Richard |
| 4,266,549 A | 5/1981 | Kimura |
| 4,330,207 A | 5/1982 | Nogami et al. |
| 4,407,964 A | 10/1983 | Elings et al. |
| 4,449,535 A | 5/1984 | Renault |
| 4,501,970 A | 2/1985 | Nelson |
| 4,516,856 A | 5/1985 | Popelka |
| 4,531,834 A | 7/1985 | Nogami |
| 4,541,438 A | 9/1985 | Parker et al. |
| 4,556,057 A | 12/1985 | Hiruma et al. |
| 4,577,110 A | 3/1986 | MacBride et al. |
| 4,600,306 A | 7/1986 | Hara et al. |
| 4,632,550 A | 12/1986 | Hara et al. |
| 4,643,877 A | 2/1987 | Opitz et al. |
| 4,661,711 A | 4/1987 | Harjunmaa |
| 4,675,529 A | 6/1987 | Kushida |
| 4,681,859 A | 7/1987 | Kramer |
| 4,682,594 A | 7/1987 | Mok |
| 4,686,371 A | 8/1987 | Birch et al. |
| 4,697,870 A | 10/1987 | Richards |
| 4,718,417 A | 1/1988 | Kittrell et al. |
| 4,722,607 A | 2/1988 | Anselment et al. |
| 4,731,326 A | 3/1988 | Thompson et al. |
| 4,751,190 A | 6/1988 | Chiapetta et al. |
| 4,753,530 A | 6/1988 | Knight et al. |
| 4,755,684 A | 7/1988 | Leiner et al. |
| 4,758,727 A | 7/1988 | Tomei et al. |
| 4,768,513 A | 9/1988 | Suzuki |
| 4,772,093 A | 9/1988 | Abele et al. |
| 4,785,806 A | 11/1988 | Deckelbaum |
| 4,786,170 A | 11/1988 | Groebler |
| 4,786,813 A | 11/1988 | Svanberg et al. |
| 4,828,984 A | 5/1989 | Schwartz |
| 4,833,332 A | 5/1989 | Robertson, Jr. et al. |
| 4,840,485 A | 6/1989 | Gratton |
| 4,852,579 A | 8/1989 | Gilstad et al. |
| 4,855,930 A | 8/1989 | Chao et al. |
| 4,877,583 A | 10/1989 | Miwa et al. |
| 4,877,965 A | 10/1989 | Dandliker et al. |
| 4,894,547 A | 1/1990 | Leffell et al. |
| 4,894,806 A | 1/1990 | Jen et al. |
| 4,895,156 A | 1/1990 | Schulze |
| 4,913,142 A | 4/1990 | Kittrell et al. |
| 4,925,804 A | 5/1990 | Hale et al. |
| 4,930,516 A | 6/1990 | Alfano et al. |
| 4,937,457 A | 6/1990 | Mitchell |
| 4,947,850 A | 8/1990 | Vanderkooi et al. |
| 4,957,114 A | 9/1990 | Zeng et al. |
| 4,972,331 A | 11/1990 | Chance |
| 4,973,848 A | 11/1990 | Kolobanov et al. |
| 4,981,138 A | 1/1991 | Deckelbaum et al. |
| 4,988,212 A | 1/1991 | Sun et al. |
| 5,003,977 A | 4/1991 | Suzuki et al. |
| 5,014,707 A | 5/1991 | Schwarz et al. |
| 5,021,661 A | 6/1991 | Masutani |
| 5,022,757 A | 6/1991 | Modell |
| 5,030,832 A | 7/1991 | Williams et al. |
| 5,034,010 A | 7/1991 | Kittrell et al. |
| 5,039,219 A | 8/1991 | James et al. |
| 5,042,494 A | 8/1991 | Alfano |
| 5,043,585 A | 8/1991 | Fehrenbach et al. |
| 5,053,626 A | 10/1991 | Tillotson |
| 5,061,075 A | 10/1991 | Alfano et al. |
| 5,061,076 A | 10/1991 | Hurley |
| 5,062,431 A | 11/1991 | Potter |
| 5,090,415 A | 2/1992 | Yamashita et al. |
| 5,092,331 A | 3/1992 | Nakamura et al. |
| 5,104,392 A | 4/1992 | Kittrell et al. |
| 5,106,387 A | 4/1992 | Kittrell et al. |
| 5,111,821 A | 5/1992 | Potter |
| 5,115,137 A | 5/1992 | Andersson-Engels et al. |
| 5,119,815 A | 6/1992 | Chance |
| 5,122,974 A | 6/1992 | Chance |
| 5,125,404 A | 6/1992 | Kittrell et al. |
| 5,127,405 A | 7/1992 | Alcala et al. |
| 5,131,398 A | 7/1992 | Alfano et al. |
| 5,143,066 A | 9/1992 | Komives et al. |
| 5,151,869 A | 9/1992 | Alcala |
| 5,154,164 A | 10/1992 | Chikama |
| 5,168,162 A | 12/1992 | Oong et al. |
| 5,187,672 A | 2/1993 | Chance |
| 5,192,278 A | 3/1993 | Hayes et al. |
| 5,196,709 A | 3/1993 | Berndt et al. |
| 5,201,318 A | 4/1993 | Rava et al. |
| 5,201,908 A | 4/1993 | Jones |
| 5,205,291 A | 4/1993 | Potter |
| 5,212,099 A | 5/1993 | Marcus |
| 5,213,105 A | 5/1993 | Gratton et al. |
| 5,257,202 A | 10/1993 | Feddersen et al. |
| 5,261,410 A | 11/1993 | Alfano et al. |
| 5,290,275 A | 3/1994 | Kittrell et al. |
| 5,293,872 A | 3/1994 | Alfano et al. |
| 5,303,026 A | 4/1994 | Strobl et al. |
| 5,304,173 A | 4/1994 | Kittrell et al. |
| 5,313,941 A | 5/1994 | Braig et al. |
| 5,315,993 A | 5/1994 | Alcala |
| 5,318,023 A | 6/1994 | Vari et al. |
| 5,318,024 A | 6/1994 | Kittrell et al. |
| 5,323,008 A | 6/1994 | Studholme et al. |
| 5,329,353 A | 7/1994 | Ichimura et al. |
| 5,332,905 A | 7/1994 | Brooker et al. |
| 5,340,716 A | 8/1994 | Ullman et al. |
| 5,345,941 A | 9/1994 | Rava et al. |
| 5,348,018 A | 9/1994 | Alfano et al. |
| 5,348,890 A | 9/1994 | Ichikawa et al. |
| 5,349,954 A | 9/1994 | Tiemann et al. |
| 5,353,799 A | 10/1994 | Chance |
| 5,363,854 A | 11/1994 | Martens et al. |
| 5,369,496 A | 11/1994 | Alfano et al. |
| 5,370,119 A | 12/1994 | Mordon et al. |
| 5,377,676 A | 1/1995 | Vari et al. |
| 5,383,467 A | 1/1995 | Auer et al. |
| 5,386,827 A | 2/1995 | Chance et al. |
| 5,395,752 A | 3/1995 | Law et al. |
| 5,402,778 A | 4/1995 | Chance |
| 5,408,996 A | 4/1995 | Salb |
| 5,413,108 A | 5/1995 | Alfano |
| 5,419,323 A | 5/1995 | Kittrell et al. |
| 5,421,337 A | 6/1995 | Richards-Kortum et al. |
| 5,421,339 A | 6/1995 | Ramanujam et al. |
| 5,422,719 A | 6/1995 | Goldstein |
| 5,435,307 A | 7/1995 | Friauf et al. |
| 5,439,000 A | 8/1995 | Gunderson et al. |
| 5,452,723 A | 9/1995 | Wu et al. |
| 5,459,323 A | 10/1995 | Morgan |
| 5,460,182 A | 10/1995 | Goodman et al. |
| 5,460,971 A | 10/1995 | Gottlieb |
| 5,467,767 A | 11/1995 | Alfano et al. |

| | | | | | |
|---|---|---|---|---|---|
| 5,474,910 A | 12/1995 | Alfano | 5,678,550 A | 10/1997 | Bassen et al. |
| 5,479,099 A | 12/1995 | Jiles et al. | 5,683,888 A | 11/1997 | Campbell |
| 5,480,775 A | 1/1996 | Ito et al. | 5,687,730 A | 11/1997 | Doiron et al. |
| 5,485,530 A | 1/1996 | Lakowicz et al. | 5,697,373 A | 12/1997 | Richards-Kortum et al. |
| 5,489,536 A | 2/1996 | Ekechukwu | 5,699,795 A | 12/1997 | Richards-Kortum et al. |
| 5,491,343 A | 2/1996 | Brooker | 5,699,798 A | 12/1997 | Hochman et al. |
| 5,492,118 A | 2/1996 | Gratton et al. | 5,701,902 A | 12/1997 | Vari et al. |
| 5,497,769 A | 3/1996 | Gratton et al. | 5,701,903 A | 12/1997 | Sano et al. |
| 5,500,536 A | 3/1996 | Nogami et al. | 5,713,352 A | 2/1998 | Essenpreis et al. |
| 5,503,616 A | 4/1996 | Jones | 5,713,364 A | 2/1998 | DeBaryshe et al. |
| 5,504,336 A | 4/1996 | Noguchi | 5,722,406 A | 3/1998 | Papaioannou |
| 5,507,287 A | 4/1996 | Palcic et al. | 5,762,609 A | 6/1998 | Benaron et al. |
| 5,515,847 A | 5/1996 | Braig et al. | 5,769,791 A | 6/1998 | Benaron et al. |
| 5,515,864 A | 5/1996 | Zuckerman | 5,772,597 A | 6/1998 | Goldberger et al. |
| 5,517,313 A | 5/1996 | Colven, Jr. | 5,785,658 A | 7/1998 | Benaron et al. |
| 5,533,508 A | 7/1996 | Doiron | 5,797,836 A | 8/1998 | Lucey et al. |
| 5,536,235 A | 7/1996 | Yabe et al. | 5,807,261 A | 9/1998 | Benaron et al. |
| 5,548,124 A | 8/1996 | Takeshima et al. | 5,807,263 A | 9/1998 | Chance |
| 5,553,614 A | 9/1996 | Chance | 5,827,177 A | 10/1998 | Oneda et al. |
| 5,555,885 A | 9/1996 | Chance | 5,852,494 A | 12/1998 | Skladnev et al. |
| 5,557,415 A | 9/1996 | Nielsen et al. | 5,893,712 A | 4/1999 | Stone et al. |
| 5,562,100 A | 10/1996 | Kittrell et al. | 5,901,261 A | 5/1999 | Wach |
| 5,564,417 A | 10/1996 | Chance | 5,902,246 A | 5/1999 | McHenry et al. |
| 5,565,982 A | 10/1996 | Lee et al. | 5,912,179 A | 6/1999 | Alvarez et al. |
| 5,579,773 A | 12/1996 | Vo-Dinh et al. | 5,916,210 A | 6/1999 | Winston |
| 5,582,168 A | 12/1996 | Samuels et al. | 5,919,140 A | 7/1999 | Perelman et al. |
| 5,590,660 A | 1/1997 | MacAulay et al. | 5,920,399 A | 7/1999 | Sandison et al. |
| 5,596,987 A | 1/1997 | Chance | 5,929,985 A | 7/1999 | Sandison et al. |
| 5,596,992 A | 1/1997 | Haaland et al. | 5,941,822 A | 8/1999 | Skladnev et al. |
| 5,601,079 A | 2/1997 | Wong et al. | 5,941,834 A | 8/1999 | Skladnev et al. |
| 5,601,087 A | 2/1997 | Gunderson et al. | 5,949,077 A | 9/1999 | Alfano et al. |
| 5,612,540 A | 3/1997 | Richards-Kortum et al. | 5,953,477 A | 9/1999 | Wach et al. |
| 5,619,992 A | 4/1997 | Guthric et al. | 5,983,125 A | 11/1999 | Alfano et al. |
| 5,623,932 A | 4/1997 | Ramanujam et al. | 5,984,861 A | 11/1999 | Crowley |
| 5,624,847 A | 4/1997 | Lakowicz et al. | 5,987,346 A | 11/1999 | Benaron et al. |
| 5,626,134 A | 5/1997 | Zuckerman | 5,991,653 A | 11/1999 | Richards-Kortum et al. |
| 5,628,310 A | 5/1997 | Rao et al. | 6,021,344 A | 2/2000 | Lui et al. |
| 5,630,423 A | 5/1997 | Wang et al. | 6,055,451 A | 4/2000 | Bambot et al. |
| 5,635,402 A | 6/1997 | Alfano et al. | 6,070,093 A | 5/2000 | Oosta et al. |
| 5,647,368 A | 7/1997 | Zeng et al. | 6,091,984 A | 7/2000 | Perelman et al. |
| 5,664,574 A | 9/1997 | Chance | 6,104,939 A | 8/2000 | Groner et al. |
| 5,673,701 A | 10/1997 | Chance | 6,167,297 A | 12/2000 | Benaron |
| 5,674,182 A | 10/1997 | Suzuki et al. | 6,246,901 B1 | 6/2001 | Benaron |

MULTI-MODAL OPTICAL TISSUE DIAGNOSTIC SYSTEM

This application is a Continuation of application Ser. No. 09/786,781 filed Mar. 9, 2001 now abandoned which is a 371 of PCT/US99/20646, filed Sep. 10, 1999, which published on Mar. 23, 2000 with Publication No. WO 00/15101 in the English language and which claimed priority to U.S. Provisional Application Nos. 60/099,875 filed Sep. 11, 1998 and 60/143,579 filed Jul. 13, 1999.

BACKGROUND OF THE INVENTION

1. Field of the Invention

The invention relates to apparatus and methods for determining tissue characteristics of, for example, a human or animal.

2. Background of the Related Art

Spectroscopic methods for determining tissue characteristics are known and have been widely used to interrogate changes in tissue. A number of these distinct spectroscopic techniques are available that provide specific information depending on the nature of the interaction of light with cells and the natural chromophores present in tissue. These interactions include the absorption of light at a particular wavelength, the reemission of absorbed light as fluorescence, the scattering (redirection) of light at a particular wavelength and the change in polarization between the absorbed or scattered light and the reemitted light.

For example, it is known to irradiate a target tissue with electromagnetic radiation and to detect returned electromagnetic radiation to determine characteristics of the target tissue. In known methods, the amplitudes and wavelengths of the returned radiation are analyzed to determine characteristics of the target tissue. For instance, U.S. Pat. No. 4,718,417 to Kittrell et al. discloses a method for diagnosing the type of tissue within an artery, wherein a catheter is inserted into an artery and excitation light at particular wavelengths is used to illuminate the interior wall of the artery. Material or tissue within the artery wall emits fluorescent radiation in response to the excitation light. A detector detects the fluorescent radiation and analyzes the amplitudes and wavelengths of the emitted fluorescent radiation to determine whether the illuminated portion of the artery wall is normal, or covered with plaque. The contents of U.S. Pat. No. 4,718,417 are hereby incorporated by reference.

U.S. Pat. No. 4,930,516 to Alfano et al. discloses a method for detecting cancerous tissue, wherein a tissue sample is illuminated with excitation light at a first wavelength, and fluorescent radiation emitted in response to the excitation light is detected. The wavelength and amplitude of the emitted fluorescent radiation are then examined to determine whether the tissue sample is cancerous or normal. Normal tissue will typically have amplitude peaks at certain known wavelengths, whereas cancerous tissue will have amplitude peaks at different wavelengths. Alternatively the spectral amplitude of normal tissue will differ from cancerous tissue at the same wavelength. The disclosure of U.S. Pat. No. 4,930,516 is hereby incorporated by reference. The above described methods are referred to as fluorescence spectroscopy.

Still other patents, such as U.S. Pat. No. 5,369,496 to Alfano et al., disclose methods for determining characteristics of biological materials, wherein a target tissue is illuminated with light, and backscattered or reflected light is analyzed to determine the tissue characteristics. The contents of U.S. Pat. No. 5,369,496 are hereby incorporated by reference. This type of method is referred to as absorption spectroscopy.

It is also known to look at the decay time of fluorescent emissions to determine the type or condition of an illuminated tissue. These methods are referred to as time resolved spectroscopy. Generally, apparatus for detection of the lifetime of fluorescent emissions have concentrated on directly measuring the lifetime of the fluorescent emissions. Typically, a very short burst of excitation light is directed at a target tissue, and fluorescent emissions from the target tissue are then sensed with a detector. The amplitude of the fluorescent emissions are recorded, over time, as the fluorescent emissions decay. The fluorescent emissions may be sensed at specific wavelengths, or over a range of wavelengths. The amplitude decay profile, as a function of time, is then examined to determine a property or condition of the target tissue.

For instance, U.S. Pat. No. 5,562,100 to Kittrell et al. discloses a method of determining tissue characteristics that includes illuminating a target tissue with a short pulse of excitation radiation at a particular wavelength, and detecting fluorescent radiation emitted by the target tissue in response to the excitation radiation. In this method, the amplitude of the emitted radiation is recorded, over time, as the emission decays. The amplitude profile is then used to determine characteristics of the target tissue. Similarly, U.S. Pat. No. 5,467,767 to Alfano et al. also discloses a method of determining whether a tissue sample includes cancerous cells, wherein the amplitude decay profile of fluorescent emissions are examined. The contents of U.S. Pat. Nos. 5,562,100 and 5,467,767 are hereby incorporated by reference.

Other U.S. patents have explained that the decay time of fluorescent emissions can be indirectly measured utilizing phase shift or polarization anisotropy measurements. For instance, U.S. Pat. No. 5,624,847 to Lakowicz et al. discloses a method for determining the presence or concentration of various substances using a phase shift method. U.S. Pat. No. 5,515,864 to Zuckerman discloses a method for measuring the concentration of oxygen in blood utilizing a polarization anisotropy measurement technique. Each of these methods indirectly measure the lifetime of fluorescent emissions generated in response to excitation radiation. The contents of U.S. Pat. Nos. 5,624,847 and 5,515,864 are hereby incorporated by reference.

None of the prior art methods discussed above alone is sufficient to accurately measure changes in tissue characteristics. That is, as more fully discussed below, as tissue undergoes changes from normal to, for example, cancerous tissue, fluorescence spectroscopy becomes less effective in determining tissue characteristics because it is less sensitive to the morphological changes occurring, as compared to absorption spectroscopy. Likewise, absorption spectroscopy alone is insufficient to assess changes in tissue characteristics because it is less sensitive to biochemical changes in tissue, as compared to fluorescence spectroscopy.

It is known to combine two or more measurement techniques to arrive at a more accurate ultimate determination. For example, U.S. Pat. No. 5,582,168 to Samuels et al., the contents of which are hereby incorporated by reference, discloses an apparatus and method for detecting changes in the lens of an eye. Samuels et al. teach measuring both transmission or Raman or fluorescence emission, as well as scattering, reflection or similar effects. The material under examination is then normalized using a ratio of the fluorescence emission intensity to the scattering or reflected intensity. However, while this method addresses biochemical changes due to disease, it does not address morphological changes due to disease.

Further, generally, prior art spectroscopic methods focus on tissue characteristics at a single point or minium number of points on the tissue. Taking measurements at just one point or a minimum number of points can be misleading as it does not provide a sufficient sampling of tissue area to accurately reflect the tissue's condition.

SUMMARY OF THE INVENTION

The invention focuses on providing methods and apparatus that provide accurate measurements of changes in characteristics of tissues. The methods and apparatus according to the invention combine more than one optical modality (spectroscopic method), including but not limited to fluorescence, absorption, reflectance, polarization anisotropy, and phase modulation to decouple morphological and biochemical changes associated with tissue changes, and thus to provide an accurate diagnosis of the tissue's condition. The measurements taken according to the various spectroscopic methods can be equally weighted for diagnostic purposes, or can be weighted in various manners to produce the best diagnostic results. For example, the results may be weighted based on characteristics particular to the tissue subject, such as, for example, patient ages, hormonal metabolism, mucosal viscosity, circulatory and nervous system differences.

The invention encompasses apparatus and methods for determining characteristics of target tissues, wherein excitation electromagnetic radiation is used to illuminate a target tissue and electromagnetic radiation returned from the target tissue is analyzed to determine the characteristics of the target tissue. Some apparatus and methods embodying the invention can be used to perform a diagnosis at or slightly below the tissue surface of, for example, a human or animal. For instance, methods and apparatus embodying the invention could be used to diagnose the condition of skin, the lining of natural body lumens such as the gastrointestinal tract, or the surfaces of organs or blood vessels. Other apparatus and methods embodying the invention can be used to perform a diagnosis deep within tissues of, for example, a human or animal, where the excitation radiation has to pass through several centimeters of tissue before it interacts with the target tissue, such as in diagnosis of tumors and lesions deep in a breast of a human or animal.

According to a preferred embodiment of the invention, an apparatus and method are provided which utilize fluorescence in combination with reflectance in order to decouple the biochemical changes from the morphological changes. The fluorescence and reflectance information may be separately analyzed and compared, or alternatively, can be calibrated to take into account the attenuation due to absorption and scattering. Other combinations of spectroscopic methods besides fluorescence and reflectance may also be appropriate.

Measurements using the various spectroscopic methods may be taken simultaneously, or may be taken one after the other provided that a critical timing window, defined as the time period between the measurements, is maintained below a certain time interval.

The above described techniques are preferably used to determine characteristics of multiple portions of a target tissue. The target tissue may be analyzed as a whole by simultaneously taking measurements at a plurality of interrogation points covering substantially the entire tissue surface, or by taking measurements at only a portion of the plurality of interrogation points covering substantially the entire tissue surface at timing intervals until measurements have been taken at all of the plurality of interrogation points.

Further, the target tissue can be divided into a plurality of field areas to create a field pattern. Measurements may then be taken at a plurality of interrogation points within each of the field areas. The field areas may be then separately analyzed and compared in order to diagnose a condition of the target tissue. The target tissue can then be redivided into a different set of field areas and the field areas analyzed and compared in order to diagnose the condition of the tissue. The field areas may be all identically sized and/or shaped, or may have varied sizes and/or shapes. Further, the target tissue may be redivided into field areas of the same size and shape as the original field areas, which then are merely repositioned, or it may be redivided into field areas of a different size and/or shape, or of varied sizes and/or shapes.

As discussed above, techniques embodying the invention can be used to determine the conditions of multiple portions of a target tissue, and the determined conditions can be used to create a map of the target tissue. Such a map could then be either displayed on a display screen, or presented in hard copy format.

Further, the techniques can be used to feed information into a pattern recognition algorithm, or neural network.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

Preferred embodiments of the invention will now be described with reference to the following drawing figures, wherein like elements are referred to with like reference numerals, and wherein.

DETAILED DESCRIPTION OF PREFERRED EMBODIMENTS

Figure 1:
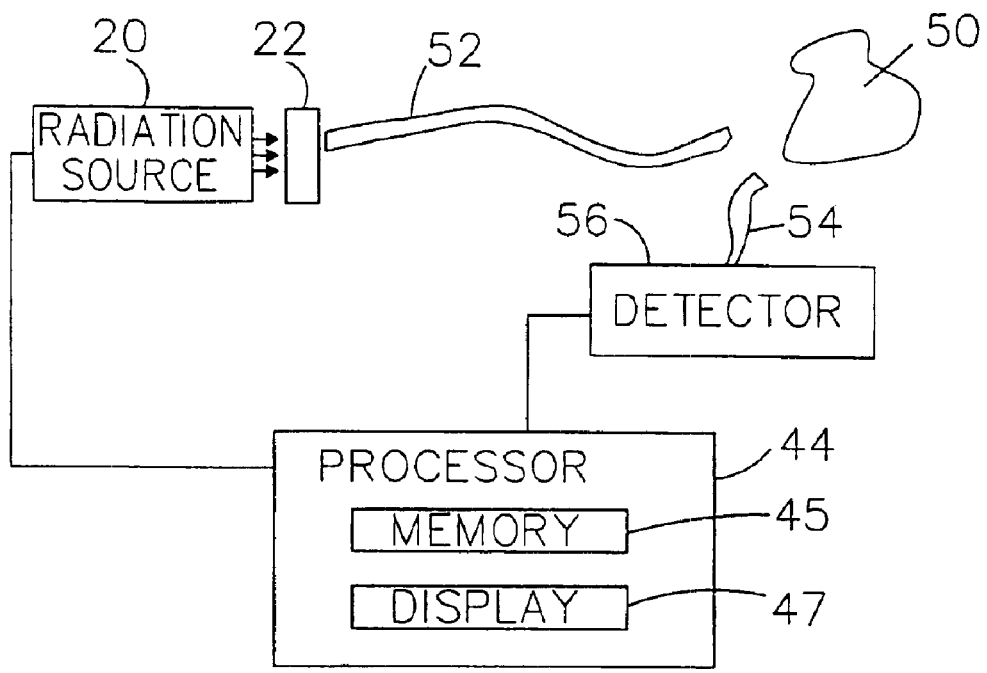
FIG. 1 is a schematic diagram showing an apparatus embodying the invention capable of performing a phase shift measurement.

In the prior art methods in the Background of the Invention Section, the information content of the interaction of light (and consequently the spectroscopic method used) is, generally speaking, specific to the type of change in tissue. That is, tumorous tissue differs from normal tissue in several ways. Tumorous tissue is generally derived from normal tissue after the latter has undergone several changes. These changes can be induced by various intrinsic and extrinsic factors. These include the presence of certain inherited traits, chromosomal mutation, virus induced malignant transformation of cells and the mutagenic effects of UV and X-ray irradiation, to name a few.

The earliest changes that occur in the course of normal cells becoming malignant are biochemical. One of the first changes noted is that of increased glycolytic activity which allows tumors to grow to a large size with decreased oxygen requirements. Invasive tumor cells secrete type IV collegenase destroying the basement membrane barrier, a principle component of which it Collagen IV. This allows the invading tumor cells to pervade into the underlying stroma or connective tissue. A number of other enzymes (e.g. cathepsins, hyaluronidases, proteoglycans and type I, II and III collagenases weaken the extracellular matrix and contribute to further tumor invasion. As tumors enlarge in size to beyond 1–2 mm$^3$, the supply of oxygen and other nutrients becomes limiting. A number of tumors have been shown to secrete tumor angiogenesis factors, which induce the formation of blood vessels within the tumor to supply the necessary oxygen and nutrients for sustained tumor growth.

Morphological changes appear later in the course of tumor progression. Such changes are defined as any change in average cell size, cell appearance, cell arrangement and the presence of non-native cells. In addition, increased perfusion due to the effects of angiogenesis results in an overall difference in tissue appearance. Normal tissue is highly differentiated in cell type and arrangement. In addition, normal cells are highly tissue specific. Tumor cells lose this tissue specificity, as well as cell differentiation and arrangement. A marked difference between tumor and normal cells is the change in the cytoskeleton, the network of microtubules and microfilaments in the cytoplasm. The cytoskeleton in normal cells is highly organized whereas that in tumor cells is disorganized. Moreover because tumor cells are rapidly dividing, the chromatin content in the nucleus and the nuclear size are both higher than in normal cells.

Absorption spectroscopy is more sensitive to the morphological changes that occur later in tumor progression. Measurements are made either in a transmission geometry where the sample is placed between the light source and detector, or in a reflectance geometry where the source and detector, are on the same side. In any configuration, changes in tissue absorption that occur between tumors and normal tissue can be measured. For example, the increased vascularization due to angiogenesis causes increased blood absorption. Light propagating through and reemitted from tissue is, however, strongly affected by light scattering interactions and does not simply depend on the absorption spectrum of tissue chromophores. Therefore, in addition to reporting changes in absorption, such techniques are sensitive to changes in size, structure and arrangement of cells and cellular organelles, all of which contribute to a change in the scattering properties of tissue. Tumor cells have enlarged nuclei and since nuclei have a different refractive index from that of the cell cytoplasm, they serve as efficient light scatterers. A similar behavior is observed from other cell organelles such as, for example, mitochondria and endoplasmic reticuli.

In absorption spectroscopy therefore, two effects, absorption and scattering, dictate the amount of radiation measured at the detector. Simply stated, these effects can either be additive or may tend to cancel out each other. It is necessary, therefore, to in some way to decouple these effects to provide an accurate measurement of tissue properties. A number of techniques have been described in the prior art to accomplish this. See, for example, U.S. Pat. No. 5,630,423 to Wang, et al. and the references cited therein, which are hereby incorporated by reference. It is now possible to obtain within reasonable accuracy the coefficients for scattering and absorption.

A different approach to absorption spectroscopy is the use of reflectance depolarization techniques. In this approach linearly polarized light is directed on the tissue and the returned reflective image is viewed through polarizers parallel and perpendicular to the direction of polarization of the incident light. The parallel component has sampled the surface tissue and the perpendicular component, after sampling deeper tissue, is scattered multiple times and is consequently depolarized. By analyzing photons that have sampled surface tissue the absorption spectrum of this tissue independent of scattering effects can be generated. Additionally, by modulating the extent of depolarization in the returned radiation used for analysis, the depth of tissue interrogated can be controlled.

Early biochemical changes are best detected by the change in fluorescence properties of native chromophores. The principle fluorophores present in tissue are the aromatic amino acids tyrosine, phenylalanine and typtophan, the metabolites NAD(H) and FAD(H) and structural proteins collagen and elastin. All of these fluorophores possess characteristic absorption and fluorescence spectra. The fluorescence properties of these molecules depends upon their physicochemical environment including pH, salvation and oxidation state. For example, the reduced form NAD(H) fluoresces while the oxidized form does not. The reverse is true for FAD(H). The action of various proteases secreted by tumor cells as described above, on structural proteins, causes the fluorescent moieties (tryptophan, phenylalanine etc.) to be exposed to a different local environment (different salvation, viscosity and hydrophobicity) thus changing their fluorescent characteristics.

Although biochemical changes precede the morphological changes that occur as a result of the former, it is unrealistic to think of diseased tissue that differs from surrounding normal tissue only in its intrinsic biochemistry. If this were true then by simply measuring the fluorescence one could identify and locate disease. In reality varying degrees of morphological change accompany the biological changes. These changes appear later in the course of tumor progression and are defined as any change in average cell nuclei, cell size, cell appearance, cell arrangement and the presence of non native cells. In addition, effects of the host response such as, for example, increased perfusion from angiogenesis results in an overall difference in tissue appearance. The morphological changes add more complexity to the measurements by absorbing and scattering both excitation and fluorescent light thereby altering the true fluorescence signal. If the tumor is early, the possibility of measurable morphological changes having occurred are low and consequently fluorescence alone may be able to identify early tumors from nearby normal tissue. However, once significant changes in morphology have occurred the measurement now involves the added complication of deconvolving or decoupling the effects of fluorescence spectral changes from changes in fluorescence signal due to scattering and reabsorption. For example, in the diagnosis of hyperplasia and adenomatous polyps from normal colonic tissue, a decrease in 390 nm fluorescence (337 nm excitation) is seen as the tissue types change from normal as taught by Shoemacher et. al at pages 63–78 of Lasers in Surg. Med (12) 1992, which is hereby incorporated by reference. This could be interpreted as a decrease in collagen fluorescence or an increase in hemoglobin absorption. In fact, the authors show that the effect is due to a screening of fluorescence from collagen (itself unchanged) in the submucosal layer by the thickening mucosa in an adenoma.

Clearly, therefore simply measuring the change in fluorescence spectral shifts or intensity changes will not be sufficient for accurately measuring changes in tissue characteristics, and making, for example, a fluorescence based diagnosis. It is difficult to make a fluorescence measurement that is truly independent of the effect of scattering and absorbance.

In order to aecouple the effects of biochemical and morphological changes, the relative degrees of which vary depending upon the extent of tumor progression, a multimodal approach is required. Such an approach requires a device capable of measuring both fluorescence and absorption spectra of the area of interest. Both measurements must be made on the same site at preferably the same time so as to ensure identical condition.

The decoupling can be carried out in a variety of ways, which are later discussed.

Time resolved fluorescence methods are largely independent of the effects of scattering and absorbance. This is especially true for diagnosis of epithelial cancer and similar conditions where the distance traversed by light is small. Time resolved measurement measures the fluorescence lifetime of a fluorophore. This is an intrinsic molecular property and as such is independent of extraneous interferences such as fluorosphore concentration (provided a measurable signal with adequate signal to noise is present) or light source fluctuations. Such methods have been demonstrated for transcutaneous measurements from fluorescent implants and have been shown to be superior to steady state fluorescence measurements. See Bambot, et al., Biosens and Bioelectronics (10) 1995 at pages 643–652 and U.S. Pat. No. 5,628,3 10 to Rao, et al. which are hereby incorporated by reference. The same tissue biochemical changes that result in fluorescence spectral shifts and intensity changes also generally change fluorescence lifetimes. It is commonly known that non radiative processes that depopulate the excited state of fluorophore cause large changes in fluorescence lifetime. Such non radiative processes are likely the result of a changing physicochemical environment surrounding intrinsic fluorophores in an emerging tumor.

Time resolved methods are accomplished in either the time domain or frequency domain, the latter is also known as phase modulation fluorimetry. Phase modulation measurements can be accomplished with cheaper and less complex instrumentation than is used to directly measure the decay time of fluorescence. For example, an intensity modulated light beam may be directed upon the sample. The fluorescence returned from the sample is also intensity modulated at the same frequency. However, because of the finite fluorescence lifetime of the fluorophore in tissue, the returned fluorescence signal is phase shifted and this phase shift is related to the fluorescence lifetime.

The biggest impediment to using time resolved methods presently is cost. This cost is proportional to the magnitude of both the modulation frequency and the frequency of light. The modulation frequency used is nominally the inverse of the lifetime of the fluorosphore being interrogated. Given the short (few nanoseconds) fluorescence lifetimes of intrinsic chromophores in tissue that serve as markers for disease, high modulation frequencies (several hundred megahertz) are required, necessitating the need for RF equipment and techniques. In addition, most intrinsic chromophores have absorption maxima at low wavelengths (high frequencies). Solid state light sources and detectors that operate at these wavelengths and that are capable of being intrinsically modulated at the requisite modulation frequencies are expensive and rare. Having said this, both areas, low wavelength light sources/detectors and RF frequency digital electronics are an active area of research and development and significant cost reductions are expected in the future.

An alternative to the phase change method discussed above to determine fluorescence lifetime is the measurement of fluorescence depolarization or anisotropy. The instrumentation used is similar to that used for reflectance depolarization. Indeed the same instrument can readily be used for measurement based on both principles. In clear solution (where photons are not depolarized due to scattering) the measurement of fluorescence polarization anisotropy provides an estimate of the fluorescence lifetime of the fluorophores being interrogated. This is represented by the Perrin Equation (Perrin et. al.) which relates fluorescence Anisotropy (r) to Lifetime (τ)

$$\frac{ro}{r} = 1 + \frac{\tau}{\phi} \qquad \text{Equation 1}$$

where $r_o$, is the anisotropy of the molecule when Brownian motion is absent, i.e. in the frozen state or in a highly viscous medium, γ is the time averaged anisotropy observed, τ is the fluorescence lifetime of the molecule and φ is the Brownian rotation correlation time.

Strictly speaking the above equation is valid only for a single exponential decay in both fluorescence lifetime and anisotropy. The anisotropy decay is single exponential only for a spherical molecule (isotropic depolarization). The rotational correlation time is defined, for simplicity, for a sphere to be;

$$\phi = \frac{\eta V}{RT} \qquad \text{Equation 2}$$

where η is the viscosity, V the volume, R the universal gas constant and T the absolute temperature.

As illustrated in Equation 1, the anisotropy reflects changes from both fluorescence lifetime and rotational correlation time. The fluorescence lifetime of intrinsic fluorophores change with tumor progression. Similarly a change in local physical properties such as microviscosity, temperature or membrane fluidity will change the rotational correlation time and resulting in a change in an isotropy. U.S. Pat. Nos. 4,115,699, 4,122,348 and 4,131,800, which are hereby incorporated by reference, disclose the measurement of changes in local microviscosity and fluidity due to malignancy using exogenous lipophilic dyes and the method of fluorescence depolarization.

The principle drawback with this technique when applied to in vivo tissue measurements is the depolarization caused by multiple scattering events in tissue. It has been shown, however, that a significant portion of the polarized excitation remains polarized before exciting the fluorophore and the resulting fluorescence is also substantially polarized when it reaches the detector. Nevertheless, it is necessary to decouple depolarization due to scattering from depolarization due to fluorescence lifetime and rotation correlation time.

The techniques according to the invention are designed to discriminate normal tissue from various cancerous tissue stages based on spectroscopic data alone. Additional factors, such as, for example, patient age, menopausal status, menstrual state, and/or previous history of disease can be added to the spectroscopic inputs in achieving better discrimination.

The multimodal approach according to the invention may be carried out in an imaging mode. In other words the multiple spectroscopic methods are used in interrogating tissue at several interrogation points at high spatial resolution concurrently. The reasoning behind this approach is the variability in spectroscopic signature of known normal tissue between patients and the fact that in 99% of the patients the entire organ is not diseased. The best way to do this without an a prior knowledge of what is normal is to measure both the normal and abnormal tissue, that is, the entire organ.

Visually normal areas on an organ with precancers or cancers are always suspect and a conclusive analysis is almost always the result of a biopsy and histology. This observation is consistent with the phenomenon of field cancerization, as discussed by D. P. Slaughter, et al., in "Field Cancerization in Oral Squamour Epithelium: Clinical Implication of Multicentric Origin" in Cancer 6, 1953, at pages 963–968, which is hereby incorporated by reference. A considerable body of evidence exists, particulary for breast cancer, which shows that supposedly normal breast epithelium derived from patient's breast cancer is "condemned" in that it is precancerous. This explains the relatively high rate of second breast cancer incident in women treated for the disease, as discussed by G. F. Schwartz, et al. in "The Prevalence of carcinoma In Situ In Normal and Cancer Associated Breasts", Hum Pathol 16, 1985, at pages 796–807, which is hereby incorporated by reference. The inventors believe a similar pattern exists with cervical cancer and may explain the high number of women (50%) with a history of negative pap tests who develop cervical cancer, as discussed in Cancer Diagnostics, The World Market, Clinica Reports, PJB Publications, 1997, at page 72, which is hereby incorporated by reference. Such a pattern further warrants the use of imaging modes in cancer detection.

The invention will now be further discussed with reference to the drawings.

FIG. 1 is a schematic diagram of an apparatus according to a preferred embodiment of the invention. The apparatus includes a source 20, which produces electromagnetic radiation that is conducted to a target tissue 50, preferably by one or more emission optical fibers 52. The apparatus may also include a filter 22 for selectively controlling the electromagnetic radiation emitted from the radiation source 20. The source 20 could comprise, for example, a laser, a light emitting diode, a fluorescent tube, an incandescent bulb, or any other type of device that is capable of emitting electromagnetic radiation, as is well known to those skilled in the art.

Electromagnetic radiation returned from target tissue 50, is sensed by a detector 56. As discussed below, the detector may employ any of the known methods for determining tissue characteristics, including but not limited to fluorescence, absorption, reflectance, anisotropy, phase change, and any other know spectroscopic methods including those methods discussed in the Background of the Invention section of this disclosure. Preferably, the detector employs two or more spectroscopic methods which provides for a better or more accurate measure of target tissue characteristics than one measurement alone, and thus a more complete diagnosis of the tissue's condition.

The returned electromagnetic radiation comprises both fluorescent emissions from fluorophores in the target tissue that have been excited by the excitation radiation and the excitation electromagnetic radiation that is scattered or reflected from the target tissue. In a preferred embodiment of the invention, as later discussed, the detector 56 makes intensity based measurements on both forms of said electromagnetic radiation. These measurements are combined to decouple the morphological changes from the biochemical changes. The detector may comprise, for example, a photomultiplier tube, a photosensitive diode, a charge coupled device, or any other type of electromagnetic radiation sensor, as is also well known to those skilled in the art.

If the detector is a small charge coupled device, it could be located at a distal end of an endoscope or catheter instrument. In this instance, the charge coupled device would already be located adjacent the target tissue such that the detector could directly sense the return radiation. The charge coupled device would then need some means for communicating its information to a processor 44.

If the detector is not a charge coupled device located at a distal end of an instrument, the returned electromagnetic radiation may be conducted to the detector 56 through one or more return optical fibers 54. The return optical fibers 54 and the excitation optical fibers 52 may be co-located within the same instrument, or they may be located in separate instruments. Alternately, the same optical fibers within an instrument may be used to perform both excitation and return functions.

The processor device 44 may include a memory 45 and a display 47. In fact, the processor device may comprise a typical personal computer.

In the preferred embodiments of the invention, the detector 56 may detect the fluorescent emissions from fluorophores in the target tissue simultaneously with the excitation electromagnetic radiation that is scattered or reflected from the target tissue to provide a complete analysis of the subject tissue. Alternatively, the device may be configured to first detect the fluorescent emissions from fluorophores in the target tissue, and then subsequently, the excitation electromagnetic radiation that is scattered or reflected from the target tissue. In the later case, the time period between detections, hereinafter referred to as the "critical timing window," must be minimized to avoid motion artifacts and/or significant tissue changes that will denigrate the overall results. The time period between detections is preferably less than approximately 0.25 seconds; however, the smaller the time period, the more accurate the results will be.

Figure 2:
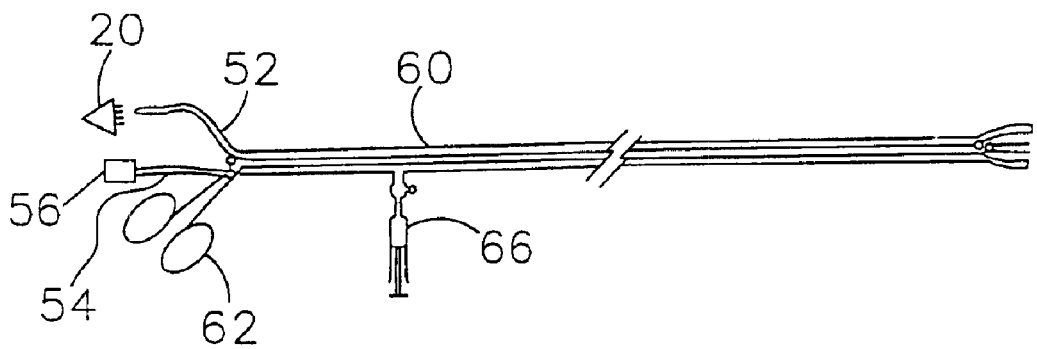
FIG. 2 is a schematic diagram of an endoscope embodying the invention.

FIG. 2 shows an endoscope that could be used to practice the measuring techniques according to the invention. The endoscope 60 includes a transmit optical fiber bundle 52, which can convey excitation electromagnetic radiation from a radiation source 20 to a target tissue. The endoscope 60 also includes a return optical fiber bundle 54 for communicating fluorescent emissions and/or reflected/scattered electromagnetic radiation from a target tissue to a detector 56. In alternative embodiments, the transmit and return optical fibers may be co-located, may be the same fibers, or may be a double set of fibers, as discussed below.

That is, it is preferable to make simultaneous detections at a plurality of interrogation points rather than at just one point or a minimum number of points. This allows evaluation of the field effect changes over an area of the tissue or substantially the entire tissue, as will be more fully discussed below. Taking measurements at just one interrogation point or a minimum number of interrogation points can be misleading as it does not provide a sufficient sampling of tissue area to accurately reflect the tissue's condition.

For example, the detector could be configured to make detections at a large number of interrogation points distributed over substantially the entire surface area of the subject tissue. That is, return optical fibers 54 could include a large number of optical fibers distributed to allow detections to be made at a corresponding large number of interrogation points on the tissue, preferably covering substantially the entire surface of the subject tissue. Each of the optical fibers could transmit excitation electromagnetic radiation to the subject tissue and then return the return electromagnetic radiation to the detector 56. The tissue could be analyzed as a whole, or divided into a plurality of field areas.

Figure 7A:
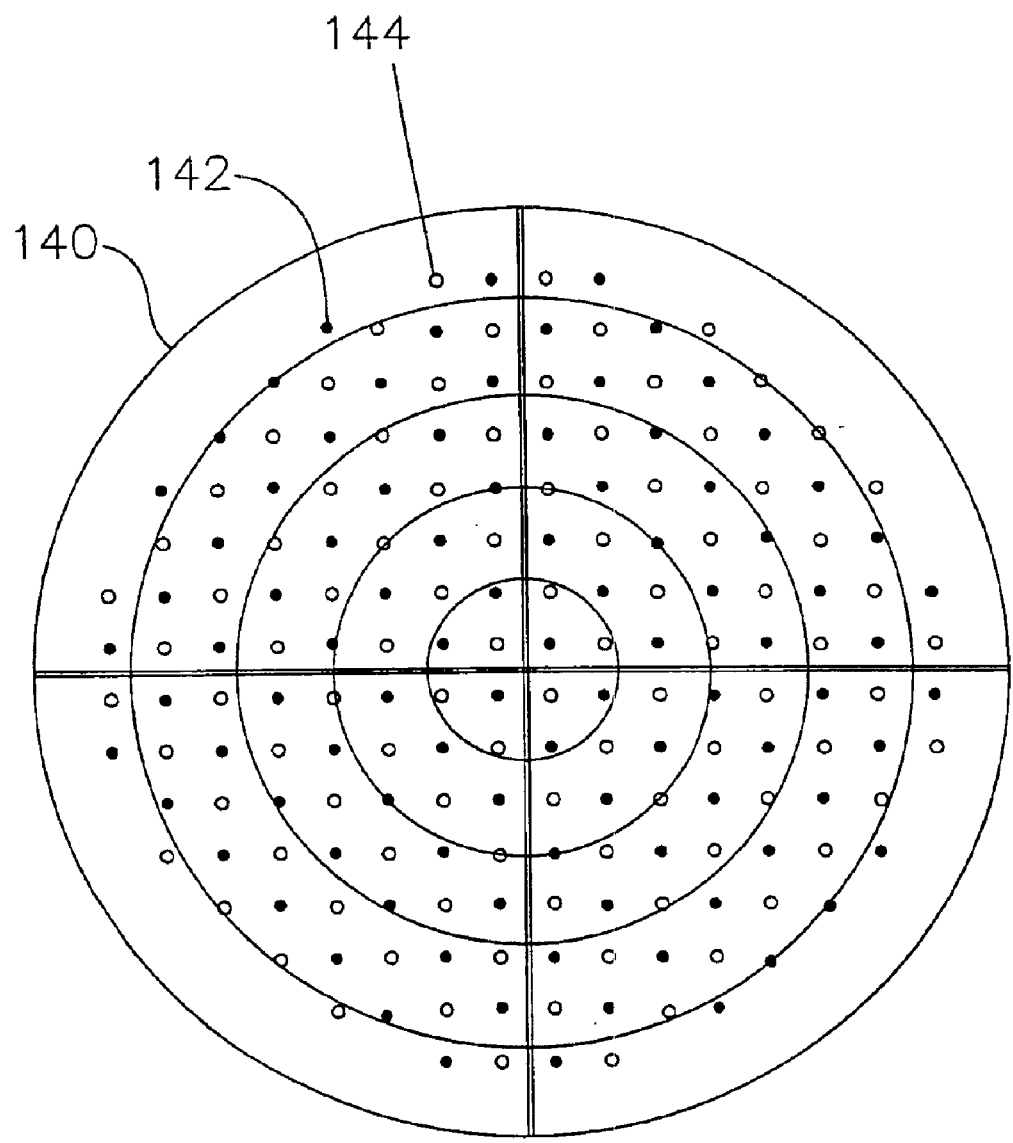
FIGS. 7A–7D, 8 and 9 show various arrangements of optical fibers.
Figure 7B:
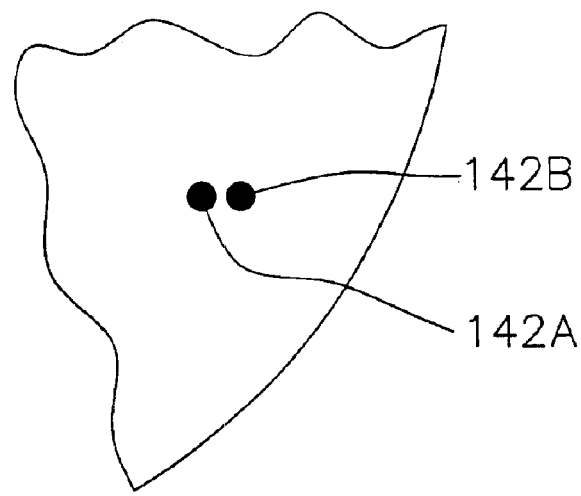

Alternatively, a transmitting optical fiber and a return optical fiber could be located at each of the interrogation points (see, for example, FIG. 7B). Further, each interrogation point could include a double set of optical fibers, a transmitting optical fiber and a return optical fiber for detecting fluorescence, and a transmitting optical fiber and a return optical fiber for detecting scattering or reflectance (see, for example, FIG. 7C). In such a case, the optical fibers could be arranged to focus on the same point on the subject tissue (see, for example, FIG. 7D).

Figure 5:
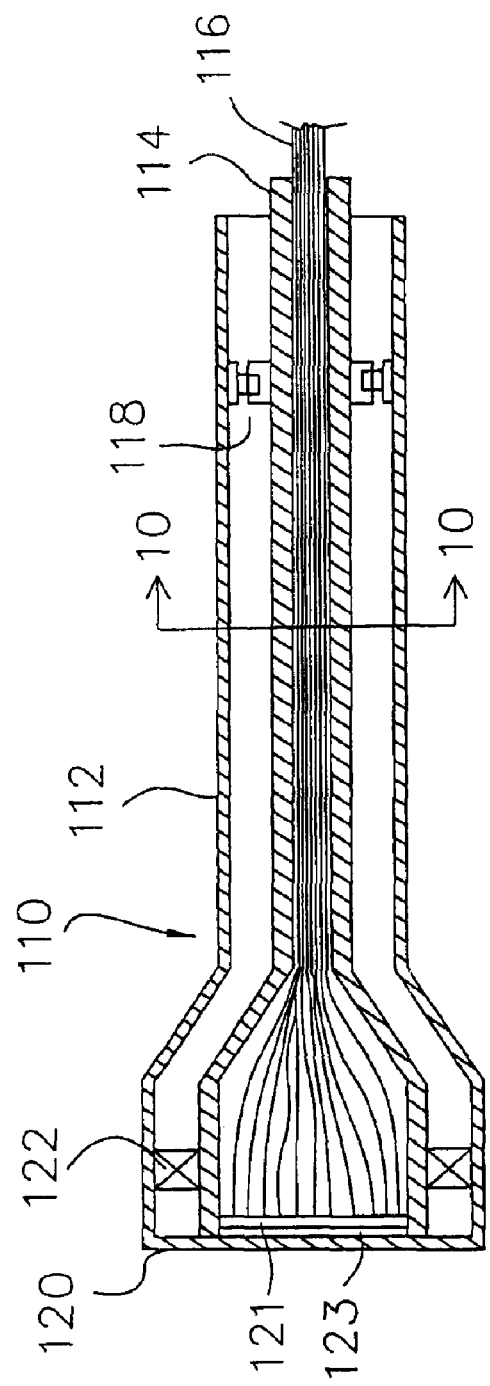
FIG. 5 is a cross-sectional view of another embodiment of the invention.

Additionally, the apparatus may include a rotatable core 114, as discussed with respect to the embodiment of FIG. 5, or alternatively, the tissue may be mounted on a rotatable table (not shown), so that the detector 56 would make detections at just a portion of the multiple interrogation points. Then, either the rotatable head or the rotatable table could be rotated and the detector would make detections at the next set of interrogation points. The process would continue to complete, for example, six rotations in order to cover substantially the entire surface of the subject tissue.

The endoscope 60 may also include a handle 62 for positioning the endoscope, or for operating a device 64 on a distal end of the endoscope 60 intended to remove tissue samples from a patient. The endoscope may also include a device 66 for introducing a dose of medication to a target tissue. Also, the source of electromagnetic radiation 20 may be configured to emit a burst of therapeutic radiation that could be delivered to a target tissue by the endoscope.

Figure 3A:
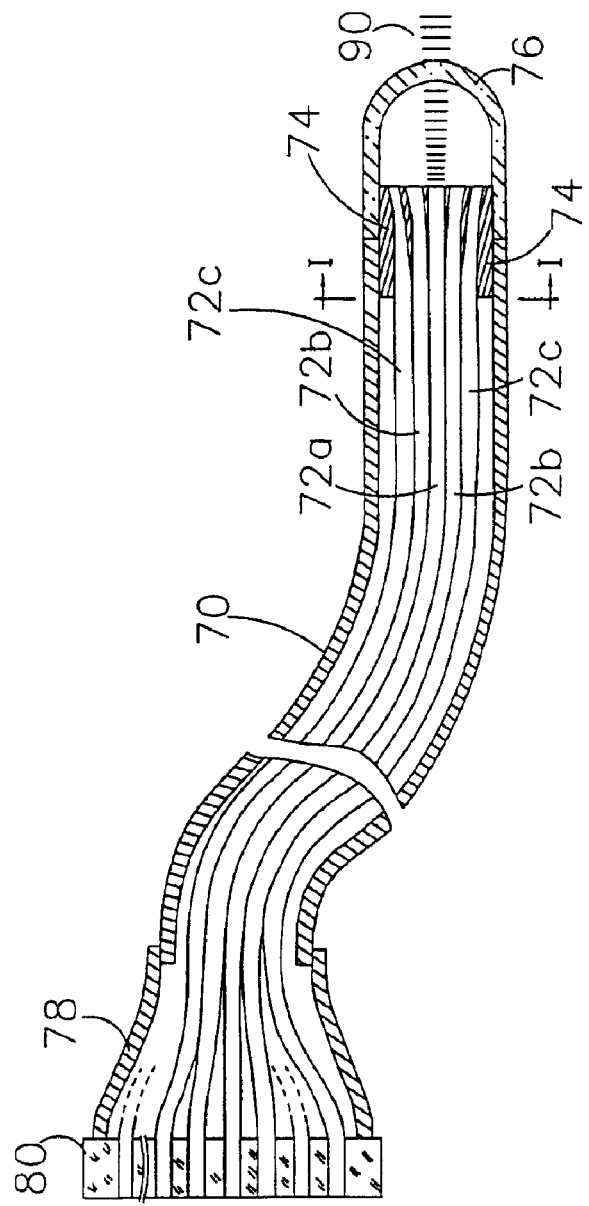
FIGS. 3A and 3B show another embodiment of the invention.
Figure 3B:
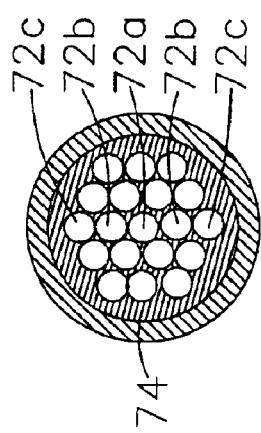

FIGS. 3A and 3B show the structure of an endoscope or catheter which may embody the invention. The apparatus includes a long body portion 70 which is intended to be inserted into a body of a human or animal. The body portion 70 must have a diameter sufficiently small to be inserted into blood vessels or other natural lumens of the human or animal.

The device includes a proximal end 80, which holds proximal ends of optical fibers 72a–72c. The optical fibers extend down the length of the device and terminate at a distal holding portion 74. The distal holding portion 74 holds the optical fibers in a predetermined orientation. The optical fibers are held such that they can illuminate selected portions of the distal end 76 of the device. This orientation also allows the distal end of the optical fibers to receive radiation from selected areas outside the distal end 76 of the device.

As best seen in FIG. 3B, the optical fibers are arranged such that there is a single central optical fiber 72a surrounded by a first ring of optical fibers 72b, which is in turn surrounded by a second ring of optical fibers 72c. Of course, other orientations of the optical fibers are possible.

By applying excitation electromagnetic radiation to selected ones of the optical fibers, and monitoring the returned electromagnetic radiation through selected ones of the optical fibers, it is possible to determine characteristics of target tissues at selected locations outside the distal end of the device. For instance, if the central optical fiber 72a emits electromagnetic radiation 90 toward a target tissue, and returned electromagnetic radiation is sensed through the same optical fiber, the returned electromagnetic radiation can be analyzed using any of the above methods to determine characteristics of a target tissue located adjacent the center of the distal end of the device. The same process can be used to determine the condition of a target tissue at different locations around the distal end of the device.

Figure 4A:
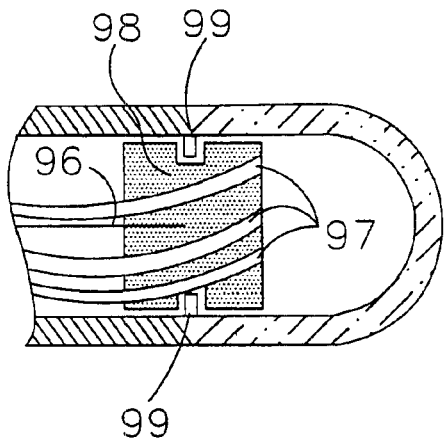
FIGS. 4A, 4B and 4C show the end portions of various embodiments of the invention.
Figure 4B:
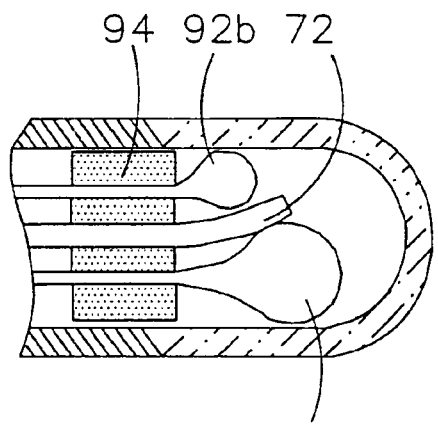
Figure 4C:
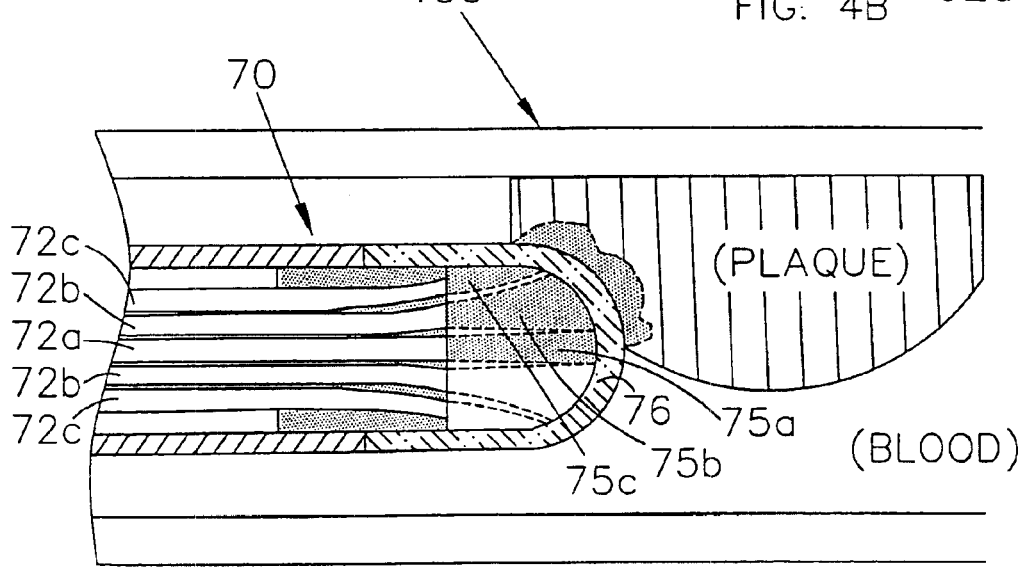

FIGS. 4A–4C show various different distal ends of the device.

In FIG. 4A, the distal ends of the optical fibers are held by a holding portion 98 that aims the distal ends of the optical fibers 97 in a particular direction. A flexible wire or bar 96 is attached to the holding portion 98 and extends to the proximal end of the device. By rotating the flexible wire or bar 96, the holding portion 98 can also be rotated. This allows the distal ends of the optical fibers to be aimed at different portions of the distal end of the device.

FIG. 4B shows another embodiment of the invention that includes one or more inflatable balloon portions 92a, 92b. An optical fiber 72 is located in the center of the device by a holding portion 94. Each of the inflatable balloons 92a, 92b is also held by the holding portion 94. By selectively inflating or deflating the different balloon portions, the optical fiber 72 may be aimed to illuminate different portions of the distal end of the device or to receive return radiation from selected locations adjacent the distal end of the device.

FIG. 4C shows an embodiment of the device similar to the embodiment shown in FIGS. 3A and 3B. This figure shows how electromagnetic radiation passing down through the optical fibers 72a–72c can be used to selectively illuminate material or tissue adjacent selected portions of the distal end of the device. In FIG. 4C, only the upper optical fibers are emitting electromagnetic radiation outside the device. This electromagnetic radiation is being used to destroy or atomize plaque which has formed on an inner wall of a blood vessel. By applying electromagnetic radiation to selected ones of the optical fibers, a doctor can carefully remove or correct problems with target tissues or materials.

Another device embodying the invention that can be used to determine tissue characteristics is shown, in longitudinal cross-section, in FIG. 5. The instrument 110 includes a cylindrical outer housing 112 with a circular end cap 120 configured to abut the target tissue. A rotating cylindrical inner core 114 is mounted in the outer housing 112. A bundle of optical fibers 116 are located inside the inner core 114.

The optical fibers 116 pass down the length of the inner core 114 and are arranged in a specific pattern at the end adjacent the end cap 120 of the outer housing 112. The end of the inner core 114 adjacent the end cap 120 is mounted within the outer housing 112 with a rotating bearing 122. The end cap 120 is at least partially transparent or transmissive so that electromagnetic radiation can pass from the optical fibers, through the end cap, to illuminate a target tissue adjacent the end cap 120. Light scattered from or generated by the target tissue would then pass back through the end cap 120 and back down the optical fibers 116.

The inner core 114 is also mounted inside the outer housing 112 by a detent mechanism 118. The detent mechanism is intended to support the inner core 114, and ensure that the inner core is rotatable within the outer housing 112 by predetermined angular amounts.

Figure 6A:
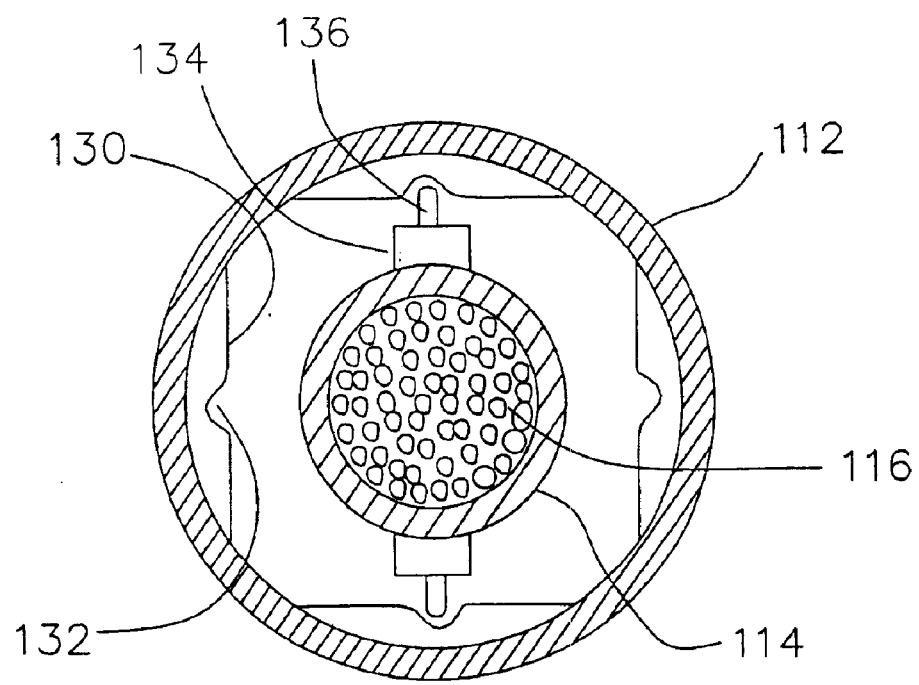
FIGS. 6A and 6B are alternative cross-sectional views of the apparatus of FIG. 5 taken along section line 10—10.

A cross sectional view of an embodiment of the instrument, taken along section line 10—10 of FIG. 5, is shown in FIG. 6A. The inner core 114 is supported within the outer housing 112 by the detent mechanism. In this embodiment, the detent mechanism includes two mounts 134 with spring loaded fingers 136 that are biased away from the inner core 114. The detent mechanism also includes four stoppers 130, each of which has a central depression 132. The spring loaded fingers 136 are configured to engage the central depressions 132 of the stoppers 130 to cause the rotatable inner core to come to rest at predetermined angular rotational positions. In the embodiment shown in FIG. 6A, four stoppers are provided in the inner surface of the outer housing 112. Thus, the inner core 114 will be rotatable in increments of approximately 90°. In alternate embodiments similar to the one shown in FIG. 6A, four mounts 134, each having its own spring loaded finger 136, could be attached to the inner core 114. The provision of four such mounts would serve to keep the inner core 114 better centered inside the outer housing 112.

Figure 6B:
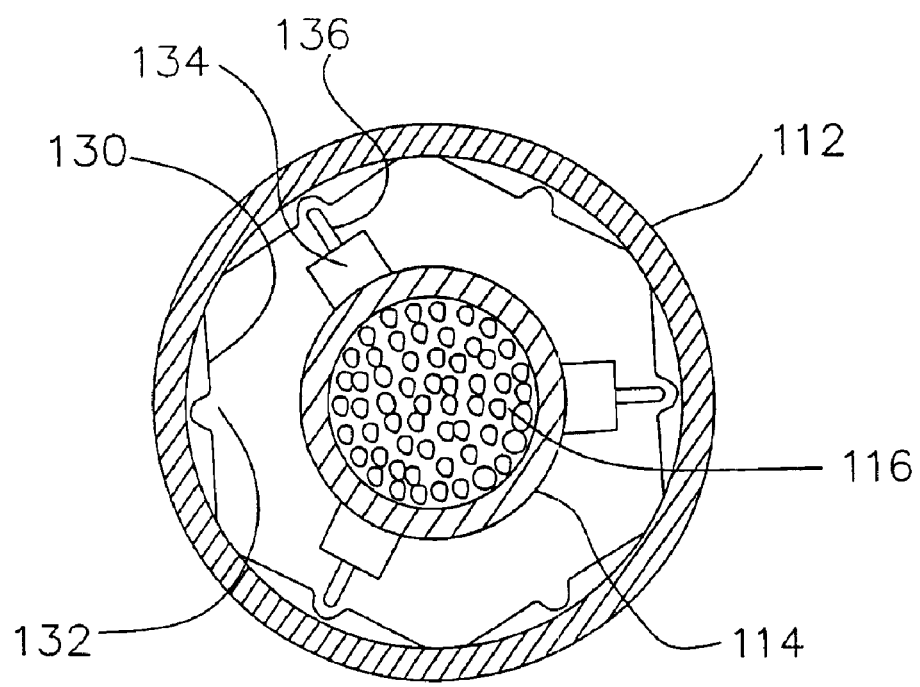

An alternate embodiment of the detent mechanism is shown in FIG. 6B. In this embodiment, six stoppers 130 are spaced around the inside of the outer housing 112. Three mounts 134, each having its own spring loaded finger 136, are mounted on the inner core 114. The three mounts 134 are spaced around the exterior of the inner core 114 approximately 120° apart. This embodiment will allow the inner core to be rotated to predetermined positions in increments of 60°. In addition, the location of the three mounts, 120° apart, helps to keep the inner core 114 supported in the center of the outer housing 112.

With reference to FIG. 5, the ends of the optical fibers may be mounted on a circular end plate 121 that holds the optical fibers in a predetermined pattern. The circular end plate 121 would be rigidly attached to the end of the cylindrical inner core 114. In addition, an index matching agent 123 may be located between the end plate 121 and the end cap 120 on the outer housing 112. The index matching agent 123 can serve as both an optical index matching agent, and as a lubricant to allow free rotation of the end plate 121 relative to the end cap 120.

A diagram showing how the optical fibers are positioned on the face of an embodiment of the instrument is shown in FIG. 7A. The face of the instrument, which would be the end cap 120 of the device shown in FIG. 5, is indicated by reference number 140 in FIG. 7A. The black circles 142 represent the locations of optical fibers behind the end cap 120. The hollow circles 144 represent the positions that the optical fibers will move to if the inner core 114 of the instrument is rotated approximately 90°. Thus, each of the circles represent positions that can be interrogated with the optical fibers.

In some embodiments of the device, a single optical fiber will be located at each of the positions shown by the black circles 142 in FIG. 7A. In this instance, excitation light would travel down the fiber and be emitted at each interrogation position indicated by a black circle 142. Light scattered from or produced by the target tissue would travel back up the same fibers to a detector or detector array, such as detector 56 shown in FIG. 1.

Figure 7C:
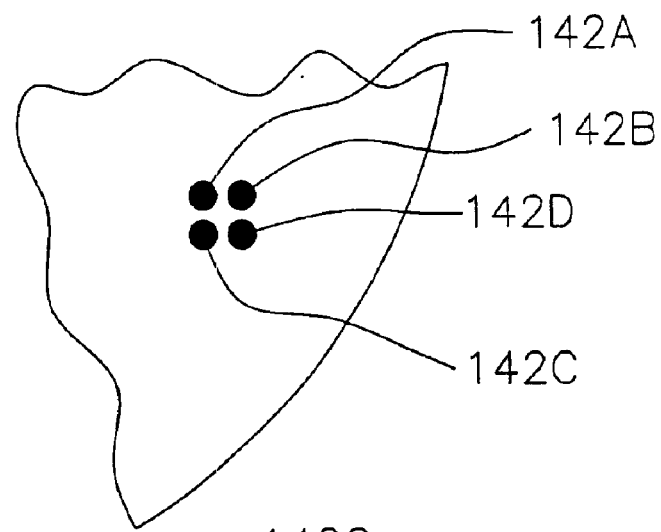
Figure 7D:
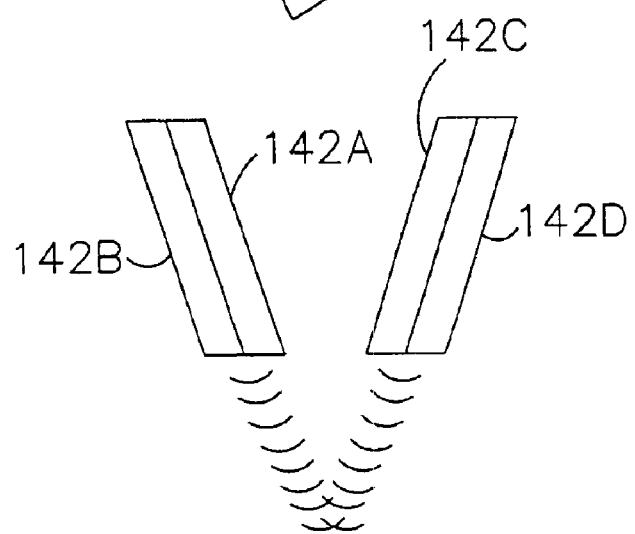

In alternate embodiments, pairs of optical fibers could be located at each position indicated by the black circles 142A, 142B, as shown in FIG. 7B. In the alternate embodiments, one optical fiber of each pair would conduct excitation light to the target tissue, and the second optical fiber of each pair would conduct light scattered from or generated by the target tissue to a detector. In still other alternate embodiments, multiple fibers for carrying excitation light and/or multiple fibers for carrying light scattered from or generated by the target tissue could be located at each interrogation position indicated by a black circles 142A, 142B, 142C, 142D to allow simultaneous detection of, for example, both fluorescence and reflectance, as shown in FIG. 7C. In this latter case, the optical fibers could be arranged to focus on the same point of subject tissue, as shown in FIG. 7D.

To use an instrument having the optical fiber pattern shown in FIG. 7A, the instrument would first be positioned so that the end cap 120 is adjacent the target tissue. The end cap 120 may be in contact with the target tissue, or it might be spaced from the surface of the target tissue. Also, an index matching material may be interposed between the end cap 120 and the target tissue. Then, the optical fibers would be used during a first measurement cycle to simultaneously measure tissue characteristics at each of the interrogation positions in FIG. 7A having a black circle 142. The tissue characteristics could be measured using any of the measurement techniques discussed above. Then, the inner core 114 would be rotated approximately 90° within the outer housing 112, and the optical fibers would be used during a second measurement cycle to simultaneously measure tissue characteristics at each of the interrogation positions in FIG. 7 having a hollow circle 144.

The instrument may include markings (not shown) on the end cap 120 or elsewhere, which acts as a locator tool to allow a user to determine how many rotations have been made, and thus how much of the tissue has been analyzed.

Constructing an instrument as shown in FIGS. 5, 6A or 6B, and having any of the optical fiber patterns shown in FIGS. 7A–7D, has many important advantages. For example, constructing an instrument in this manner allows the instrument to interrogate many more points in the target tissue than would have been possible if the inner core did not rotate. The ability to rotate the inner core 114, and take a second series of measurements at different locations on the target tissue, essentially increases the resolution of the device.

In addition, when a large number of optical fibers are packed into the tissue contacting face of an instrument, cross-talk between the optical fibers can occur. The cross-talk can occur when excitation light from one interrogation position scatters from the target tissue and enters an adjacent interrogation position. Cross-talk can also occur if excitation light from a first interrogation position travels through the target tissue and enters an adjacent interrogation position. One of the easiest ways to reduce or eliminate cross-talk is to space the interrogation positions farther apart. However, increasing the spacing between interrogation positions will reduce the resolution of the device.

An instrument embodying the invention, with a rotatable inner core, allows the interrogation positions during any single measurement cycle to be spaced far enough apart to reduce or substantially eliminate cross-talk. Because multiple measurement cycles are used, the device is able to obtain excellent resolution. Thus, good resolution is obtained without the negative impact to sensitivity or selectivity caused by cross-talk. In addition, fewer optical fibers and fewer corresponding detectors are required to obtain a given resolution.

In addition, the ability to obtain a plurality of tissue measurements simultaneously from positions spaced across the entire target tissue has other benefits. If the instrument is intended to detect cancerous growths or other tissue maladies, the target tissue area interrogated by the instrument is likely to have both normal tissue, and diseased tissue. As noted above, tissue characteristics can vary significantly from person to person, and the tissue characteristics can vary significantly over relatively short periods of time. For these reasons, one way to determine the locations of diseased areas is to establish a baseline for normal tissue, then compare the measurement results for each interrogation point to the baseline measurement. The easiest way to determine the location of a diseased area is to simply look for a measurement aberration or variance.

Because tissue characteristics can change relatively quickly, in order to establish accurate, clearly defined variances between tissue characteristics, it is desirable to take a plurality of readings simultaneously over as large an area as possible. In the preferred method according to the invention, this could include taking fluorescence measurements at a plurality of interrogation points, and then subsequently taking reflectance measurements, at the same plurality of interrogation points. Alternately, the fluorescence and reflectance measurements could be taken simultaneously. Ideally, all measurements should be conducted during the same time period. In a preferred embodiment, the apparatus and method conduct measurements at least within this critical time window. The critical time window is defined as the maximum duration of time between two spectroscopic measurements which yields the benefits described herein. Although this value may vary depending on a variety of factors including those described below, it has been determined that the critical timing window between subsequent measurements should be less than approximately 0.25 seconds and more preferably less than approximately 0.1 second, as further discussed below.

There are several effects which make it desirable to conduct fluorescent and reflectance measurements of the interrogated points either simultaneously, or as nearly simultaneously as possible. First, changes in blood pressure, which occur during each heart beat cycle can have a large affect on blood content in the tissue. Because blood strongly absorbs certain wavelengths of light, the varying amount of blood present at an interrogated point during different parts of the heart beat cycle can cause significantly varying measurement results.

To eliminate this potential error source, both fluorescent and reflectance measurements should be taken within a small enough time window that the blood content remains the same. Time periods of less than approximately 0.25 seconds should be sufficient. Another way to eliminate the potential error is to take multiple measurements of the same interrogation point during different portions of the heart beat cycle, then average the results.

Another factor to consider is patient movement. If the patient moves, even slightly, during a measurement cycle, the contact pressure between the measurement instrument and the interrogated tissue can change. This can also affect the measurement results. Thus, obtaining measurements simultaneously, or as nearly simultaneously as possible, also helps to prevent measurement errors caused by patient movement.

Also, because tissue tumors can be as small as approximately 1 mm, the resolution of the device is preferably approximately 1 mm. In other words, to obtain the requisite resolution, the spacing between interrogation positions should be approximately 1 mm. Unfortunately, when the interrogation positions are approximately 1 mm apart during a single measurement cycle, significant cross-talk can occur, and the accuracy of the measurement results is poor.

An instrument embodying the invention allows the interrogation positions to be spaced sufficiently far apart to essentially eliminate cross-talk, while still obtaining the requisite 1 mm resolution. Although not all measurements are obtained at exactly the same time, during each measurement cycle, simultaneous measurements are made at positions spaced across the entire target tissue, which should include both normal and diseased areas. Thus, the results from each measurement cycle can be used to detect variances in tissue characteristics that help to localize diseased areas. For these reasons, an instrument embodying the invention balances the competing design requirements of resolution, elimination of cross-talk, and the desire to make all measurements simultaneously to ensure that time-varying tissue characteristics are taken into account.

Figure 8:
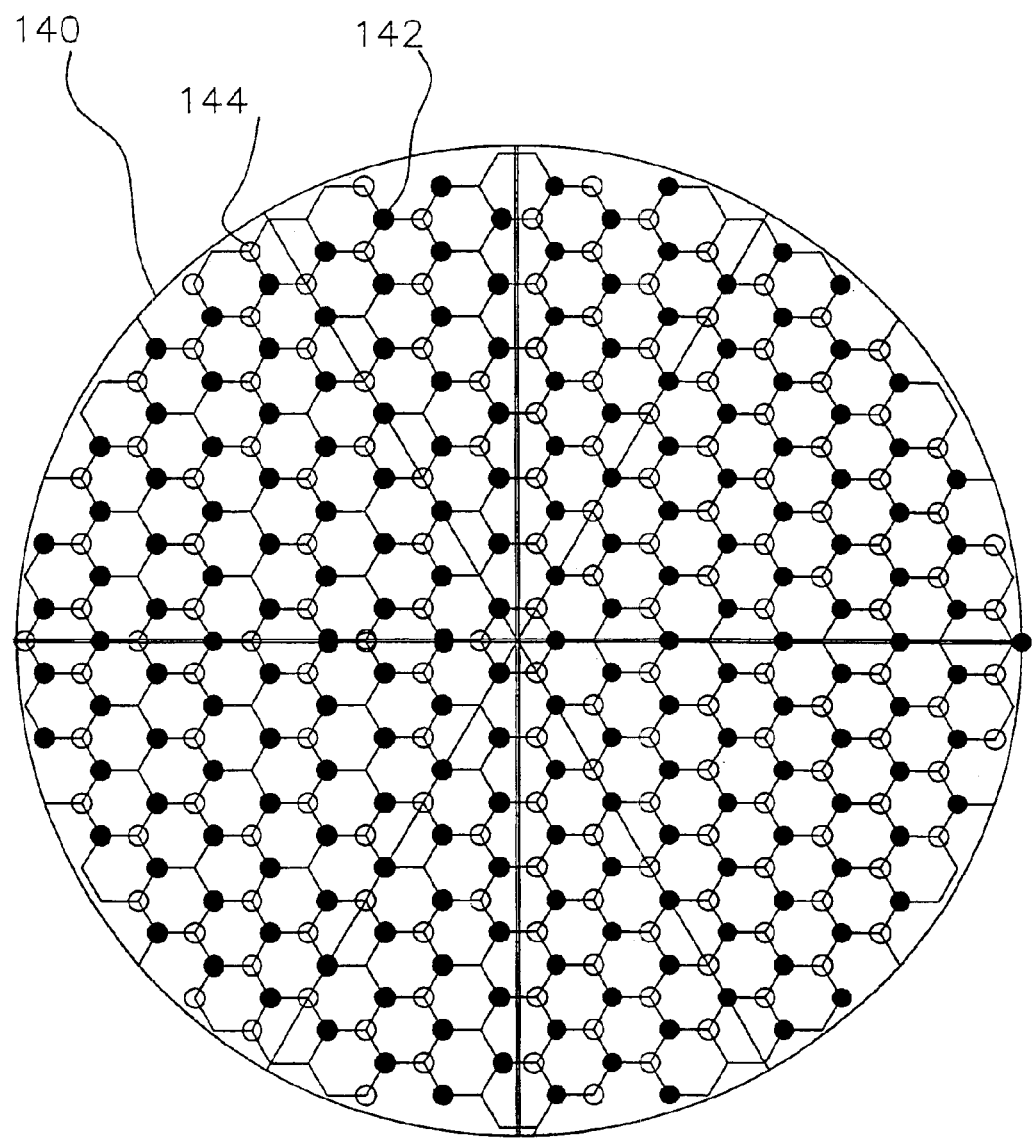

A second arrangement for the optical fibers of a device as shown in FIG. 5 is depicted in FIG. 8. In this embodiment, the interrogation positions are arranged in a hexagonal honeycomb pattern. The black circles 142 indicate the positions that would be occupied by optical fibers during a first measurement cycle, and the hollow circles 144 indicate positions that would be occupied by the optical fibers during a second measurement cycle after the inner core 112 has been rotated by approximately 60°. This pattern achieves maximum spacing between adjacent interrogation positions during each measurement cycle, and essentially doubles the resolution of the instrument.

Figure 9:
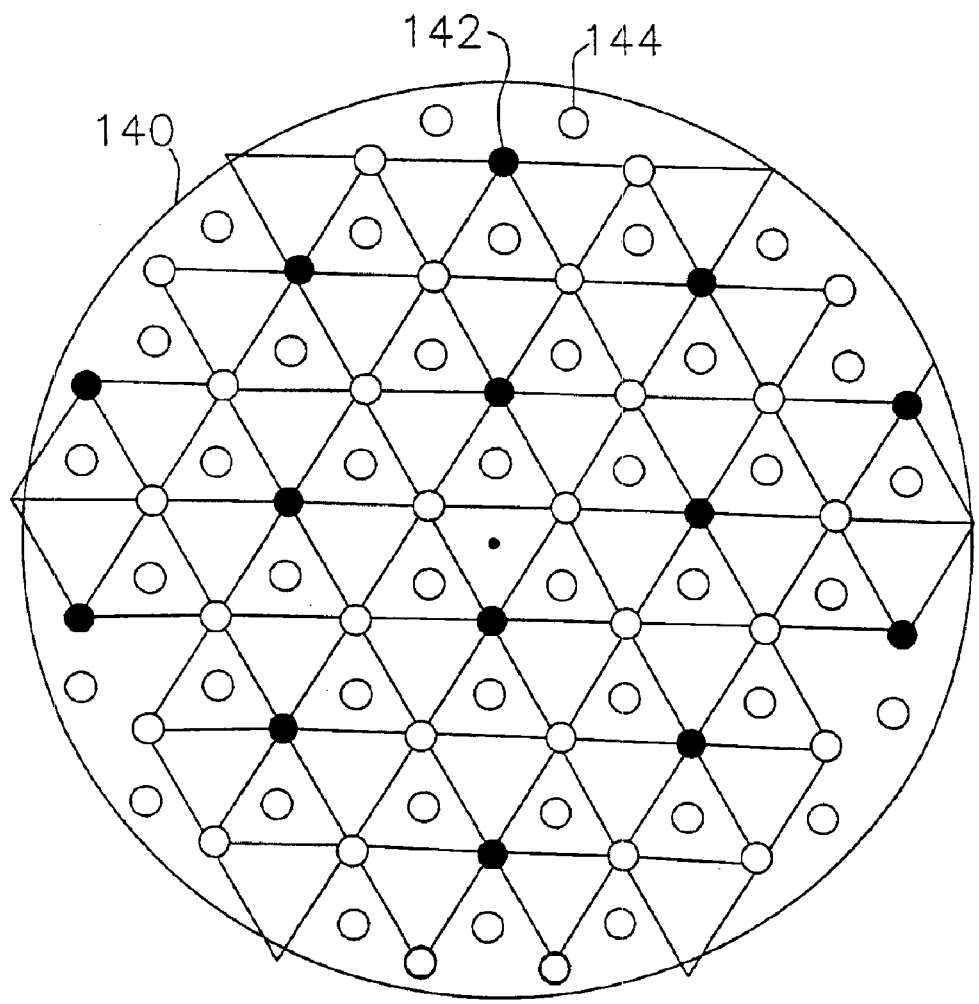

A third arrangement for the optical fibers of a device shown in FIG. 5 is depicted in FIG. 9. In this embodiment, the optical fibers are again arranged according to a hexagonal honeycomb pattern. However, far fewer optical fibers are used in this embodiment. This third embodiment is intended for use in a measurement process that calls for six measurement cycles. The inner core of the device would be rotated approximately 60° between each measurement cycle. Over the course of the six measurement cycles, the device would ultimately interrogate all the black circled 142 and hollow circled 144 interrogation positions shown in FIG. 9. This embodiment allows for even greater separation distances between the interrogation positions during a single measurement cycle (to reduce or substantially eliminate cross-talk), while still achieving excellent measurement resolution. In addition, far fewer optical fibers and corresponding detectors would be required to achieve a given measurement resolution.

Experimental studies were conducted by the applicants to determine the spacing between interrogation positions that is needed to substantially eliminate cross-talk. The studies were conducted using a pair of optical fibers at each interrogation position, wherein one fiber in each pair provides excitation light, and the other fiber in each pair is used to detect light. The excitation optical fibers had a diameter of approximately 200 $\mu$m, the detection fibers had a diameter of approximately 100 $\mu$m. Measurements were made on optical reference standards, and tissue. Under these conditions, it was necessary to space the interrogation positions approximately 3 mm apart to substantially eliminate cross-talk. Thus, if an instrument were not designed as described above, so that the inner core can rotate the interrogation positions to different locations on the target tissue, the device would only be capable of achieving a resolution of approximately 3 mm.

The presently preferred embodiment of the invention utilizes an optical fiber pattern similar to the one shown in FIG. 9. Thus, the device is designed to conduct six measurement cycles to complete all measurements within the target tissue. The inner core 114 is rotated 60° between each measurement cycle. The presently preferred embodiment utilizes optical fiber pairs at each interrogation position. Each optical fiber pair includes an excitation fiber having an approximately 200 μm diameter, and a detection optical fiber having an approximately 100 μm diameter. The arrangement of the optical fibers allows the interrogation positions to be spaced approximately 3.0–3.5 mm apart, while still achieving a resolution of approximately 1 mm.

Figure 10:
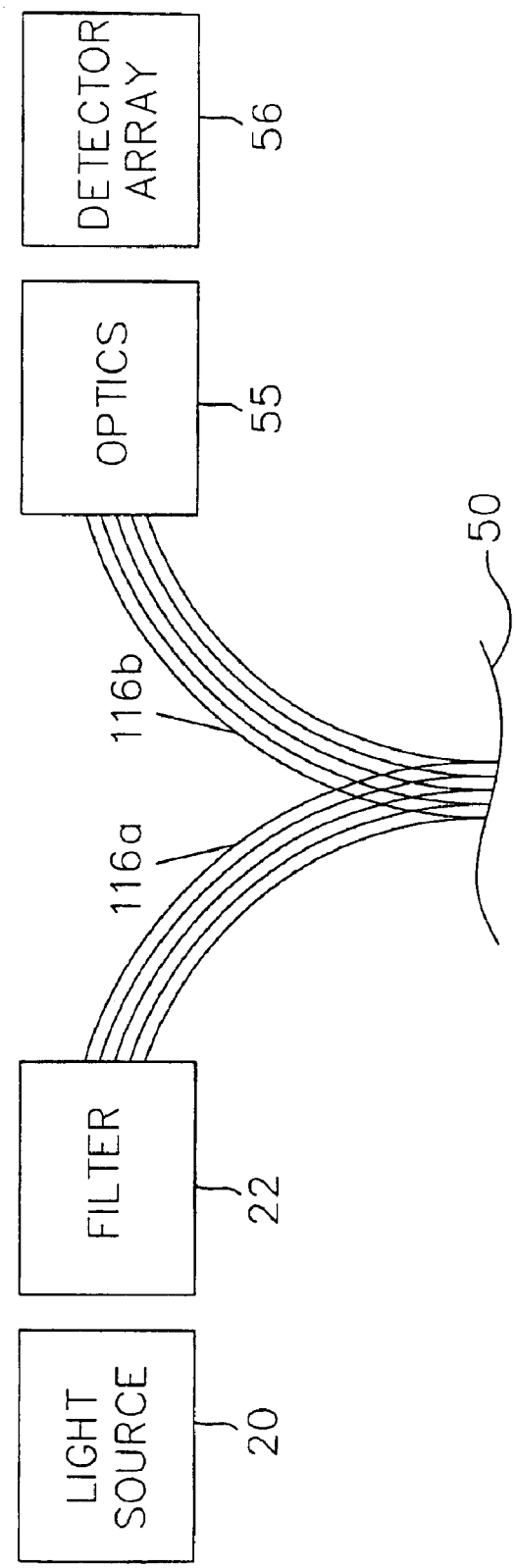
FIG. 10 shows another embodiment of the invention.

To determine the locations of diseased areas within a target tissue it is necessary to take measurements at a plurality of different locations in the target tissue spaced in at least two dimensions. Each measurement may require multiple excitation wavelengths, and detection of multiple wavelengths of scattered or generated light. Thus, the measurements involve three measurement dimensions, two dimensions for the area of the target tissue, and a third dimension comprising the spectral information. A device capable of conducting measurements in these three dimensions is shown in FIG. 10.

The instrument includes a light source 20, and a filter assembly 22. A plurality of excitation optical fibers 116a lead from the filter assembly 22 to the target tissue 50. A plurality of detection fibers 116b lead away from the target tissue 50. The excitation optical fibers 116a and the detection optical fibers 116b are arranged in pairs as described above.

The light source 20 and filter assembly 22 allow specific wavelengths of light to be used to illuminate the target tissue 50 via the excitation optical fibers 116a. The filter assembly 22 could be a single band pass optical filter, or multiple optical filters that can be selectively placed between the light source 20 and the excitation optical fibers 116a. Alternatively, the light source 20 and filter assembly 22 could be replaced with a wavelength tunable light source. In yet other alternate embodiments, a plurality of light sources, such as lasers, could be used to selectively output specific wavelengths or wavelength bands of excitation light. Other sources may also be appropriate.

The detection fibers lead to an optical system 55. The light from the detection fibers 116b passes through the optical system and into a detector array 56. The detector array may comprise a plurality of photosensitive detectors, or a plurality of spectrophotometers. The detector array 56 is preferably able to obtain measurement results for each of the detection fibers 116b simultaneously.

The optical system 55 can include a plurality of optical filters that allow the detector array 56 to determine the intensity of light at certain predetermined wavelengths. In a preferred embodiment, the detector array would be a two dimensional array of photosensitive detectors, such as a charge coupled device (CCD). The optical system would comprise a spectrograph that is configured to separate the light from each detection optical fiber 116b into a plurality of different wavelengths, and to focus the different wavelengths across a line of pixels on the CCD. Thus, each line of pixels on the CCD would correspond to a single detection fiber. The intensities of the different wavelengths of light carried by a single detection fiber 116b could be determined based on the outputs of a line pixels of the CCD. The greater the output of a particular pixel, the greater the intensity at a particular wavelength.

The preferred embodiment is able to achieve excellent flexibility. Because all wavelengths of light are always detected, the instrument software can simply select the pixels of interest for each measurement, and thereby determine the intensity at particular wavelengths. During a first measurement, certain pixels representative of fluorescent characteristics could be examined. During a subsequent measurement, different pixels representative of scattering characteristics could be examined. Also, the device could be essentially re-configured to take completely different measurements by simply changing the control software. Thus, a single device could be used for a wide variety of different kinds of measurements.

In preferred methods of the invention, one of the structures described above would be used to conduct a series of measurements cycles. Where the embodiment having the rotatable core is employed, the inner core of the device would be rotated between measurement cycles. Once all measurements of a measurement cycle are completed, the inner core would be rotated, and additional measurement cycles would be conducted.

In the preferred methods, however, measurements are conducted using two or more spectroscopic methods during each measurement cycle. For instance, during a single measurement cycle the device may conduct a measurement of fluorescent characteristics, and a measurement of reflectance characteristics. However, other measurements and combinations of spectroscopic methods may also be appropriate. Then, the fluorescence and reflectance measurements can be compared and analyzed to decouple the effects due to biochemical and morphological tissue changes to provide for a more accurate diagnosis of the tissue's conditions.

As previously discussed, the measurements can be taken over substantially the entire surface area of the subject tissue, simultaneously or in intervals, and the results analyzed. Alternatively, the subject tissue can be divided into field areas to create a field pattern. Dividing the subject tissue into field areas allows analysis of particular areas of the tissue, for example, particular areas of the tissue where changes are likely to occur.

Figure 11A:
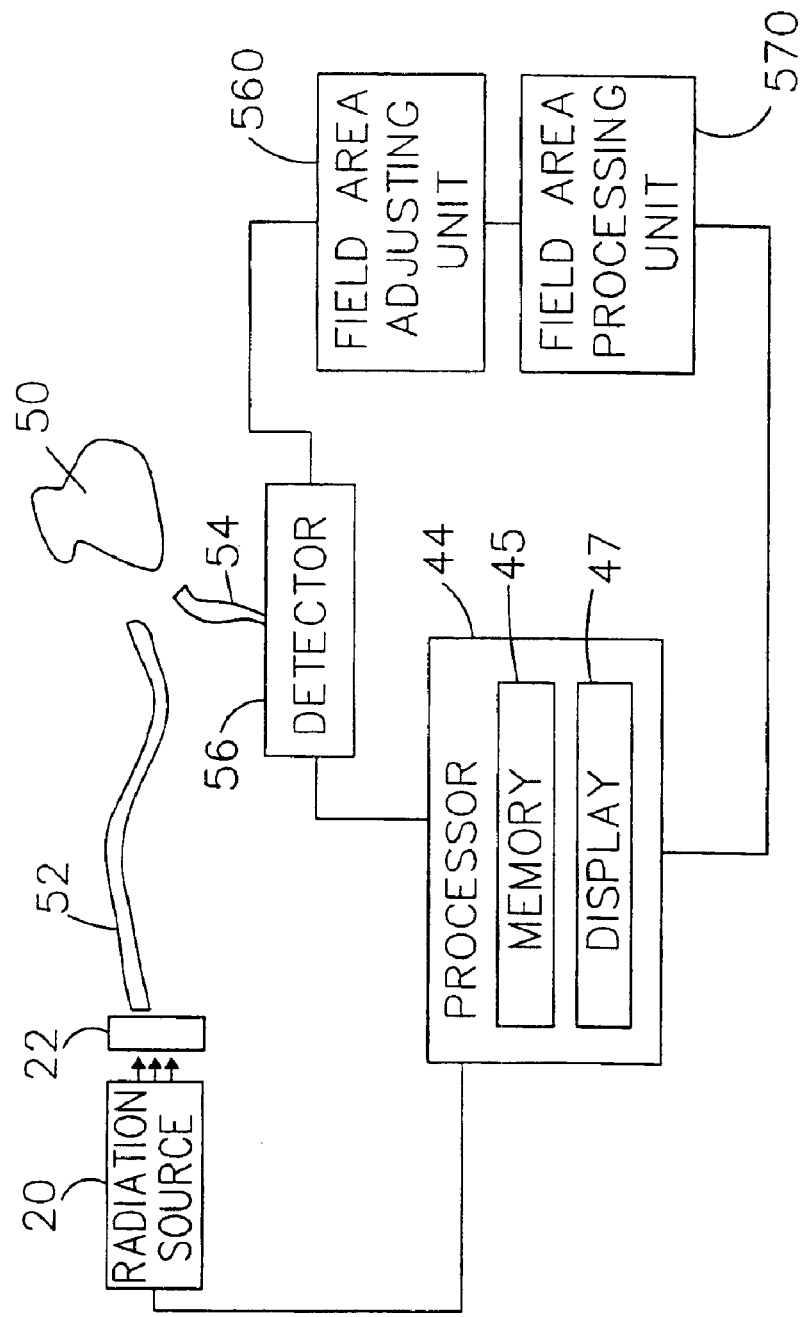
FIG. 11A is a schematic diagram showing another embodiment of the invention.
Figure 11B:
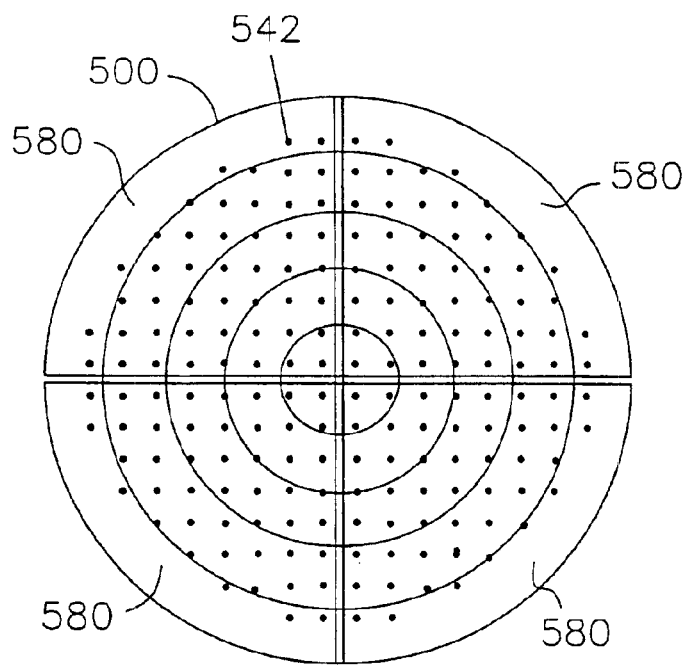
FIGS. 11B–11D show how target tissue can be divided into a plurality of field areas.
Figure 11C:
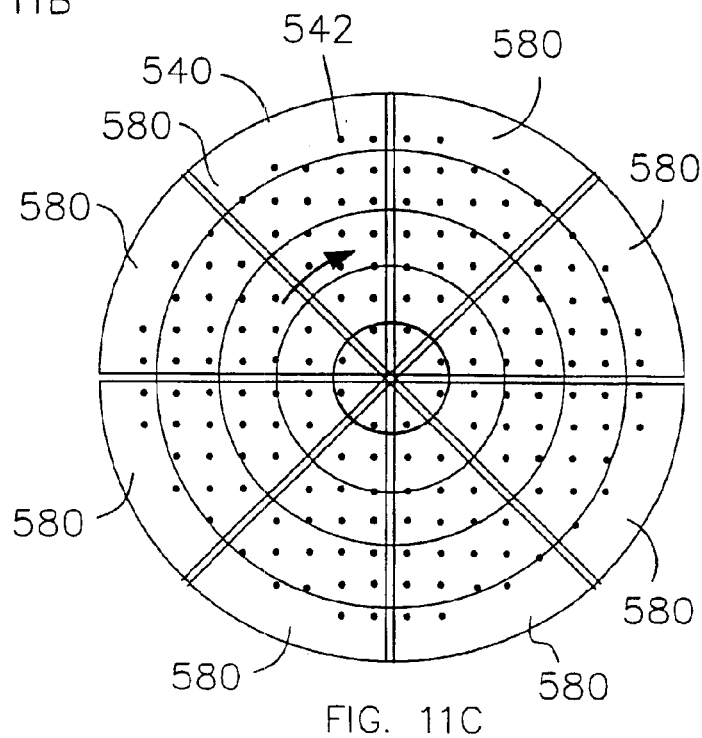
Figure 11D:
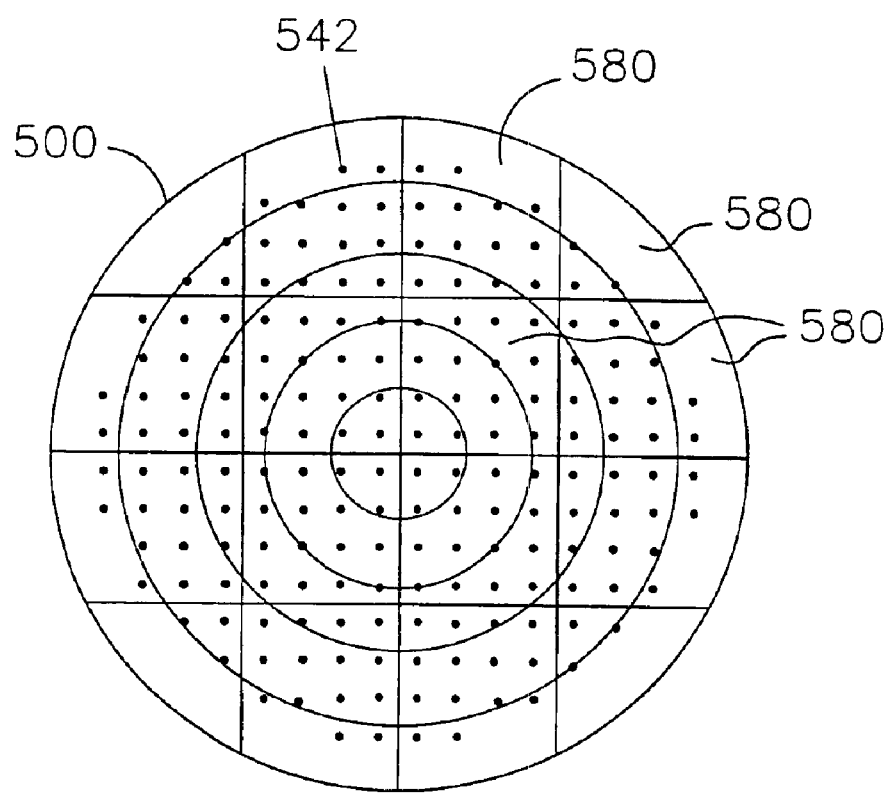

For example, the apparatus of FIG. 1 could further include a field area adjusting unit 560 and field area processing unit 570, as shown in FIG. 11A. The field area adjusting unit 560 would divide the target tissue into a plurality of field areas 580, as shown in FIGS. 11B–11D, to create a field pattern 500. The field areas 580 could be any desired shape and size (see, for example, the different sized and shaped field areas shown in FIGS. 11B–11D). Further, the divisions could be based on visual inspection of the target tissue, or on results of previous testing performed on the target tissue, and could be preprogramed into the apparatus, or input by a user. Measurements would then be taken by the detector 54 at each of a plurality of interrogation points 542 within the respective field area and the field area processing unit 570 would then analyze the measurements for each of the respective field areas 580. The field area processing unit 570 could further compare the results for each respective field area 580 to the results for other field areas 580.

FIGS. 11B and 11C show 4 and 8 "pie-shaped" field areas, respectively. In each case, after measurements were taken by the detector 54 at each of a plurality of interrogation points 542 within the respective field areas and the results analyzed by the field area processing unit 570 for each of the respective field areas 580, the field area adjusting unit 560 could reset the field areas 580 by rotating the field area to group different sets of interrogation points (see arrow in FIG. 11C), or could set field areas having a different size and shape, such as the field areas shown in FIG. 11D. As shown in FIG. 11D, these field areas do not need to be identical in size and/or shape.

Alternatively, the field area adjusting unit 560 and field area processing unit 570 could be incorporated into the processor 44 and the divisions could be preprogramed into the processor or accompanying software.

Figure 12:
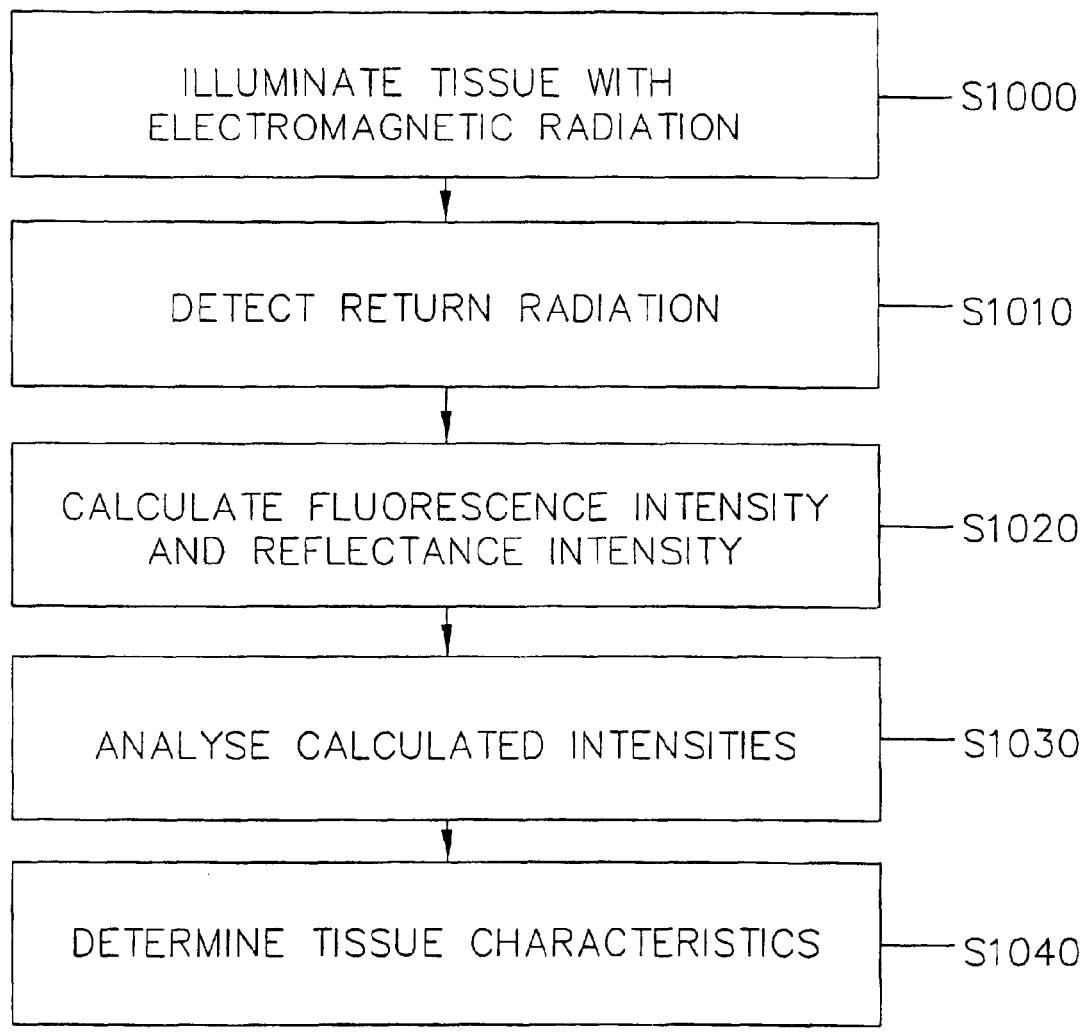
FIG. 12 shows the steps of a method embodying the invention.

FIG. 12 shows steps of a preferred method according to the invention. In a first step S1000, a target tissue is illuminated with electromagnetic radiation at predetermined wavelengths, preferably one wavelength for detecting fluorescence characteristics and one wavelength for detecting reflectance characteristics. In a second step S1010, the detector 56, preferably utilizing one of the optical fiber arrangements discussed above, detects returned electromagnetic radiation. In step S1020, the fluorescence and reflectance intensities are calculated, and in step S1030, the fluorescence and reflectance intensities are compared and analyzed using a preferred method discussed below. In step S1040, the tissue characteristics are determined.

The deconvolution, or decoupling can be carried out in a variety of ways as described below. Any or all of the discriminant parameters can be combined together in order to improve the overall discrimination.

1. Using a linear combination of fluorescence and reflectance measured intensities as the discriminant parameter.

$$P = aF_{\lambda m} + bR_{\lambda x} + cR_{\lambda m} \qquad \text{Equation 1}$$

Where $\lambda x$ is the fluorescence excitation wavelength, $\lambda m$ is the fluorescence emission wavelength, F is the fluorescence intensity and R is the reflectance intensity. The factors a, b and c are weighing factors that are empirically selected to give the best discrimination.

2. Using a linear combination for fluorescence and reflectance ratios as the discriminant parameter.

$$P = a\frac{F_{\lambda m}}{R_{\lambda m}} + b\frac{F_{\lambda m}}{R_{\lambda x}} \qquad \text{Equation 2}$$

3. Using a linear combination for fluorescence and reflectance ratios at multiple fluorescence emission wavelengths as the discriminant parameter.

$$P = a\frac{F_{\lambda 1m}}{F_{\lambda 2m}} + b\frac{R_{\lambda 1m}}{R_{\lambda 1x}} + c\frac{R_{\lambda 2m}}{R_{\lambda 2x}} \qquad \text{Equation 3}$$

Where $\lambda 1m$ and $\lambda 2m$ are two distinct fluorescence emission wavelengths, $\lambda 1x$ and $\lambda 2x$ are the corresponding excitation wavelengths, F is the fluorescence intensity and R is the reflectance intensity. The factors a, b and c are weighing factors that are empirically selected to give the best discrimination.

4. Using quantum yield (also known as quantum efficiency) measurement as the discriminant parameter. The quantum yield defines the true fluorescence yield in terms of the number of fluorescence photons generated by the fluorophore per photon of light absorbed.

$$P = \frac{aF_{\lambda m}}{1 - bR_{\lambda x}} \qquad \text{Equation 4}$$

The fluorescence and reflectance intensities are corrected for background light and normalized to the intensities measured off a calibration target. The factors a and b are weighing factors that are empirically selected to give the best discrimination.

5. Blood has broadband absorbance with three distinct visible peaks at around 410 nm, 545 nm and 575 nm. On the one hand, blood absorbance changes from increased vascularization in cancer tissue, and is an important marker for disease. On the other hand, blood absorbance related artifacts occur in the measured spectra from local bleeding and inflammation. The spectral discriminant factor described above must therefore be corrected for blood absorbance. This can either be done by normalizing the discriminant factor to blood reflectance.

$$P_{corr} = \frac{P}{R_{blood}} \qquad \text{Equation 5}$$

Or by subtracting the blood reflectance.

$$P_{corr} = P - d.R_{blood} \qquad \text{Equation 6}$$

Where d is an empirical correction factor and $R_{blood}$ is the reflectance of blood at an empirically selected wavelength.

6. Alternatively the intensity set, $F_{\lambda m}$, $R_{\lambda m}$ and $R_{\lambda x}$, where $\lambda$ is selected for each fluorophore are collectively modulated against the pathology results in a principle component analysis or a logistic regression. These can then form the basis of pattern recognition techniques, such as, for example, classification and regression trees (CART), as taught by L. Brieman, et al. in Classification and Regression Trees, Monterey Calif.: Wadsworth & Brooks/Cole, 1984, which is hereby incorporated by reference, normal networks and hybrids thereof.

The techniques according to the invention are designed to discriminate normal tissue from various cancerous tissue stages based on spectroscopic data alone. Additional factors, such as, for example, patient age, menopausal status, menstrual state, previous history of disease can be added to the spectroscopic input in achieving better discrimination.

In each of the embodiments described above, in which a plurality of measurement cycles are conducted on a target tissue, and an inner core having optical fibers arranged in a predetermined pattern is rotated between measurement cycles to make a plurality of measurements on a target tissue, alternate embodiments could use some other movement mechanism other than a rotating one. The invention encompasses other types of movement or translational devices that allow a plurality of measurements to be taken on a target tissue with a limited number of detectors that are spaced far enough apart to avoid cross-talk. Also, as previously discussed, the measurements could be taken over the entire area of the subject tissue simultaneously, or the target tissue could be divided into field areas and measurements could be taken in each field area.

Further, the apparatus and methods embodying the invention make it possible to conduct in vivo measurements of tissues on the inside of body passages or lumens. An endoscope embodying the invention can be inserted into a natural body lumen of a human or animal to search for the presence of cancerous or diseased tissue. This means that no surgery would be required to locate and examine tissues inside the body of the human or animal under study.

The use together of fluorescence measurements along with reflectance measurements provides a more accurate determination of target tissue characteristics than one of the measurements alone.

The techniques described above can be used to map the conditions of an area of target tissue. For instance, the above-described techniques can be used to determine a condition of a target tissue adjacent a distal end of a measuring device. The measuring device could then be moved adjacent a different portion of the target tissue, and the measurements could be repeated. This process could be repeated numerous times to determine the conditions of different portions of a target tissue area. The determined conditions could then be used to create a map of the target tissue area, which could be printed or displayed on a monitor.

One of the most difficult problems with in vivo tissue diagnostics and disease measurement is the biological diversity of normal tissue properties between different patients, or even within the same patient. Furthermore, this diversity is time variant both in the long term and in the short term. Long term variations may be due to patient age, hormonal milieu, metabolism, mucosal viscosity, and circulatory and nervous system differences. Short term variations may be from blood perfusion changes due to heart beat, physical movement, local temperature changes etc.

Because of the variability of tissue characteristics, to accurately determine whether a target tissue is diseased, one needs to compare measurements of the target tissue to measurements of normal tissues from the same patient. The measurements of the known normal tissue should be made concurrently or simultaneously with the measurements of the target tissue. The normal tissue measurements then serve as a baseline for normalcy, variations from which may be interpreted as disease. To arrive at a baseline measurement, a number of strategies can be used.

First, visual characteristics such as pigmentations (nevi) in skin, or polyps in the colon, can be used to identify potentially abnormal regions. Normalized or averaged spectra of multiple regions surrounding these potentially abnormal, visually distinct regions can be used to establish baseline measurements. The baseline measurements can then be compared to measurements taken on the abnormal, visually distinct regions.

Measurements of normal and abnormal regions based on visual characteristics could be automated using imaging capabilities of the measurement device itself.

In an alternate strategy, measurements can be taken on spaced apart regions along a portion of a lumen or tissue. The spacing between the regions would be dependent on the type of tissue being diagnosed. Then, differentials between individual measurements taken at different regions would be calculated. If differentials are greater than a preset amount, the tissue between the excessively high differentials would be diagnosed as diseased. In yet another alternate strategy, a gradient in spectral response as one moves away from a visually suspicious site could also be used as a marker for disease. This is easily automated and can be implemented effectively in any imaging modality.

In addition, pattern recognition algorithms (e.g. neural nets) could also be used to analyze differences in readings taken from various sites in the same patient or from multiple readings from different patients.

Preliminary testing was completed utilizing the above taught apparatus and methods to determine the effectiveness of the invention in determining tissue changes in the cervix. The results are set forth below. The testing compared the results obtained by the invention to cytology, colopscopy and histology results.

The study involved 27 human enrollees; however, data from one patient could not be collected due to an equipment error. Five of the patients were measured using a first generation probe having a rigid transparent window at the device/cervix interface and a monochrometer capable of producing excitation electromagnetic radiation at wavelengths of 290 and 460 nm. However, signal-to-noise analyses indicated that stray light and other problems rendered much of the data unusable, especially at higher wavelengths (460 nm) with respect to the fluorescence measurements and at all wavelengths with respect to the reflectance measurements. For the remaining patients, a second generation probe was used having a flexible window as well as a new monochrometer, which allowed an additional excitation electromagnetic wavelength of 350 nm to be used.

Cytology, colopscopy and histology results of the twenty-one patients are compared in Table 1 below. The histopathology results for the twenty-one patients revealed that six had moderate/high grade dysplasia or above, including one cancer. Of the fifteen sub-high grade cases tested, seven had low grade dysplasia, three had inflammation, two appeared normal at colposcopy but had a history of cervical disease and were treated with a topical therapeutic ninety days prior under a separate experimental protocol, two had abnormal Pap results but were not biopsied due to normal colposcopy, and one had both normal Pap test and colposcopy results and therefore was not biopsied.

TABLE 1

| Patient Number | Cytology from Pap Test | Coposcopy Diagnosis | Histology from Biopsy |
|---|---|---|---|
| 101-001 | ASCUS | Low Grade Dysplasia | Low Grade Dysplasia |
| 101-002 | Low Grade Dysplasia | Low Grade Dysplasia | No dysplasia seen |
| 101-003 | High Grade Dysplasia | High Grade Dysplasia | High Grade Dysplasia |
| 101-004 | Cancer | Cancer | Invasive Cancer |
| 101-005 | Low Grade Dysplasia | No Lesion Seen | No Biopsy |
| 101-006 | ASCUS | No Lesion Seen | Inflammation |
| 101-007 | Reactive Changes | High Grade Dysplasia | High Grade Dysplasia |
| 101-008 | ASCUS | Low Grade Dysplasia | Low Grade Dysplasia |
| 101-009 | ASCUS | Low Grade Dysplasia | Low Grade Dysplasia |
| 101-010 | Normal | Normal | No Biopsy (Normal) |
| 101-011* | N/A | N/A | N/A |
| 101-012 | ASCUS | Metaplasia | Low Grade Dysplasia |
| 101-013 | Reactive Changes | High Grade Dysplasia | Inflammation |
| 101-014 | Not available yet | Low Grade Dysplasia | Inflammation |
| 101-015 | ASCUS | No Lesion Seen | No Biopsy |
| 101-016 | ASCUS | Metaplasia | High Grade Dysplasia |
| 101-017 | High Grade Dysplasia | No Lesion Seen | High Grade Dysplasia |
| 102-001 | Normal | Low Grade Dysplasia | Low Grade Dysplasia |
| 102-002 | High Grade Dysplasia | Parakeratosis | No lesion seen** |
| 102-003 | Normal | Low Grade Dysplasia | Low Grade Dysplasia |
| 102-004 | Inflammation | High Grade Dysplasia | Low Grade Dysplasia |
| 102-005 | Normal | Metaplasia | High Grade Dysplasia |

*Patient enrolled but not measured.
**There was no lesion seen on colposcopy, but there might be changes inside the canal.

Of the six high grade dysplasias/cancer, the Pap test mis-classified three as being either normal, reactive or ASCUS (sensitivity=50%). Of the ten sub-high grade cases for which both Pap test and biopsy results were available, the Pap test classified all ten as sub-high grade (specificity=100%). Colposcopy also classified only three of six high grade/cancer cases accurately (50% sensitivity) but correctly classified eight of ten sub-high grade lesions correctly (specificity=80%).

Intensities were examined at specific wavelengths which correspond to the presence and activity of known biomolecules in cervical tissue. Fluorescence measurements were taken at wavelengths of approximately 290 nm (Tryptophan), 350 nm (NADH) and 460 nm (FAD). Reflectance measurements were taken at wavelengths of approximately 320 nm, 420 nm Hemoglobin) and a range of 540–580 nm (Hemoglobin). These reference the dominant biomolecules forthese wavelengths; however, secondary biomolecules, such as, for example, collagen and elastin may also be excited. A reflectance peak was found at about 320 nm which appears to represent a point in the spectrum where the above discussed and other biomolecules do not absorb, thus producing the observed reflectance peak.

The measurements were made using a fiber optic system, which acquired fluorescence and reflectance intensity data as a series of CCD images. In order to extract meaningful data, the tissue spectra underwent a series of correction and calibration operations prior to tissue measurements. Wavelength calibration was performed, which involves assigning a wavelength to each spectral data point. Background subtraction was performed, which involves removing the "dark" signal present on the CCD and any ambient light signal (e.g. from room lights) acquired during tissue measurements. Intensity calibration was performed, which involves normalizing tissue spectral intensities by the intensities measured of a fluorescence/reflectance standard. Stray light correction was performed, which involves correcting tissue fluorescence spectra for excitation monochromator stray light. Also, a system response correction was performed, which involves correcting for the non-uniform spectral response of the collection system (optical fibers, filter, spectrograph, CCD).

In order to assess data quality, signal-to-noise ratio (SNR), cross talk and variability were examined. Signal-to-noise ratio is electronic noise from the CCD as well as optical "noise" and artifacts superimposed on the fluorescence signal. If the SNR is greater than needed, the exposure time can be reduced. If the SNR is too low, the exposure time may need to be increased and other options explored. Cross talk occurs when the amount of light collected by a given collection optical fiber is influenced by other surrounding excitation fibers. This parameter is strongly dependent on the stand off between the fibers and the tissue. Variability involves the amount of inter- and intra-patient variability in spectra (e.g., intensity and/or location of peaks) measured from epithelium in a given state (normal, dysplastic, etc.) which would influence the diagnostic capability of fluorescence/reflectance-based discrimination.

During this testing, three general types of data analysis were performed: mean, standard deviation and coefficient of variance. The mean, standard deviation and coefficient of variance of the intensity at each of the wavelengths for all the spectra from a patient were calculated. Analyses were performed using measurements taken at 252 data points distributed over the whole surface of the cervix. The cervix was also divided into quadrants and measurements were made for each quadrant. Then, quadrants containing normal tissue biopsy results were compared with quadrants containing tissue having abnormal biopsy results.

Inspection of the spectra for each patient from the 252 points on the cervix would be the most straightforward means of estimating SNR. For assessing crosstalk and variability, an effective means is to produce false-color maps of the cervix based on the spectral data. A key parameter of each spectrum (e.g. intensity at a signal wavelength, intensity ratio between two wavelengths) can be color coded and mapped to the location at which it was measured on the cervix. Maps of this type allow the large volume of data acquired from each patient to be condensed to a more manageable form for obtaining qualitative insight into spatial relationships in the data.

The fluorescence and reflectance intensity measurements, at each of the respective wavelengths, for all 252 data points on the cervix, was then analyzed in several different ways. First, the mean, standard deviation and the coefficient of variance was calculated using the measurement results from all 252 data points. Graphs depicting these calculated values appear in FIGS. 13–26. The data points are characterized as normal, low grade dysplasia/inflammation, or high grade displasia based on a histological examination that was performed subsequent to the spectroscopic measurements.

Next, the cervix was divided into zones, or field areas, and mean, standard deviation and coefficient of variance values were calculated on a zone-by-zone basis. The results for each zone can then be compared to one another to attempt to localize potentially abnormal zones on the cervix. The calculated values for each zone were then examined to determine if a sufficient signal-to-noise ration had been obtained. If the signal-to-noise ratio for a particular zone was too low, the data for that zone was discarded.

Also, as mentioned above, a subsequent histological examination was performed on the tissue samples collected from each patient. If a tissue sample was taken and analyzed for a particular zone having the requisite signal-to-noise ratio, the result is plotted in FIGS. 27–38. However, if a tissue sample for a particular zone of a patient was not obtained and analyzed, there was no way to characterize the data point, and the results were not plotted in FIGS. 27–38. Thus, the data points in FIGS. 27–38 only represent quadrants that had a sufficiently high signal-to-noise ratio, and that were subsequently histologically analyzed to determine their actual condition.

Finally, the data was analyzed on a "by-rotation basis." As described above, the device used to collect the data has forty-two (42) optical fiber interrogation points distributed over the face that contacts the cervix. A first measurement cycle is conducted to collect 42 measurement results. Then, the optical fibers are rotated 60°. During a second measurement cycle, an additional 42 measurement results are obtained at the new locations. This process of rotation and measurement is repeated until measurements have been conducted at all 252 points across the cervix.

The obtained measurements were analyzed on a by-rotation basis. In other words, the mean, standard deviation and coefficient of variance was calculated for the 42 measurements taken during the first measurement cycle, the new values were calculated using the 42 measurements taken during each subsequent measurement cycle. Note, that the measurement results from each cycle are substantially evenly distributed over the entire cervix. All the calculated values for each by-rotation measurement cycle are shown in FIGS. 39–50.

Figure 13:
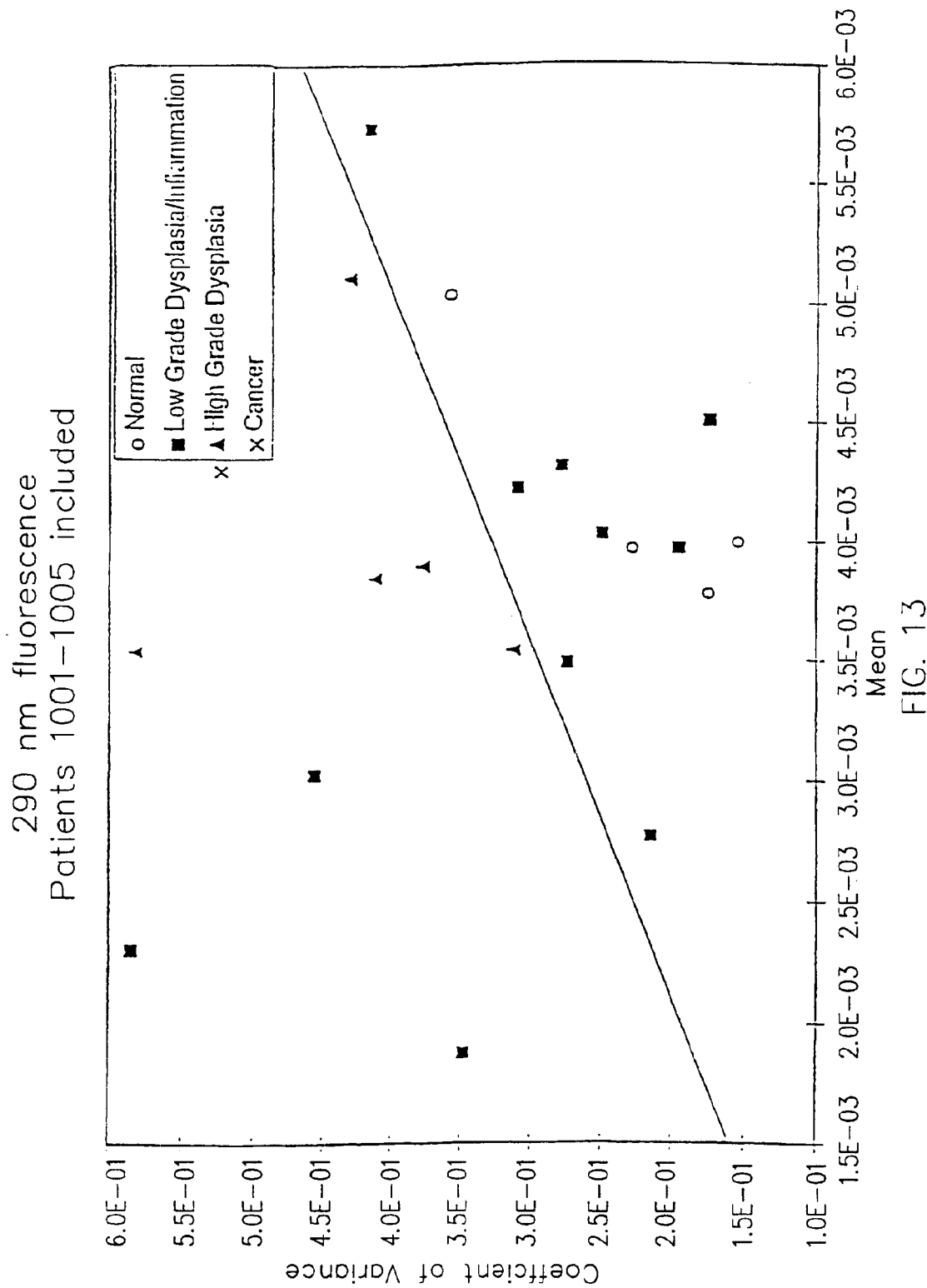
FIGS. 13–51 are graphs illustrating the results of various tests conducted utilizing the invention.
Figure 14:
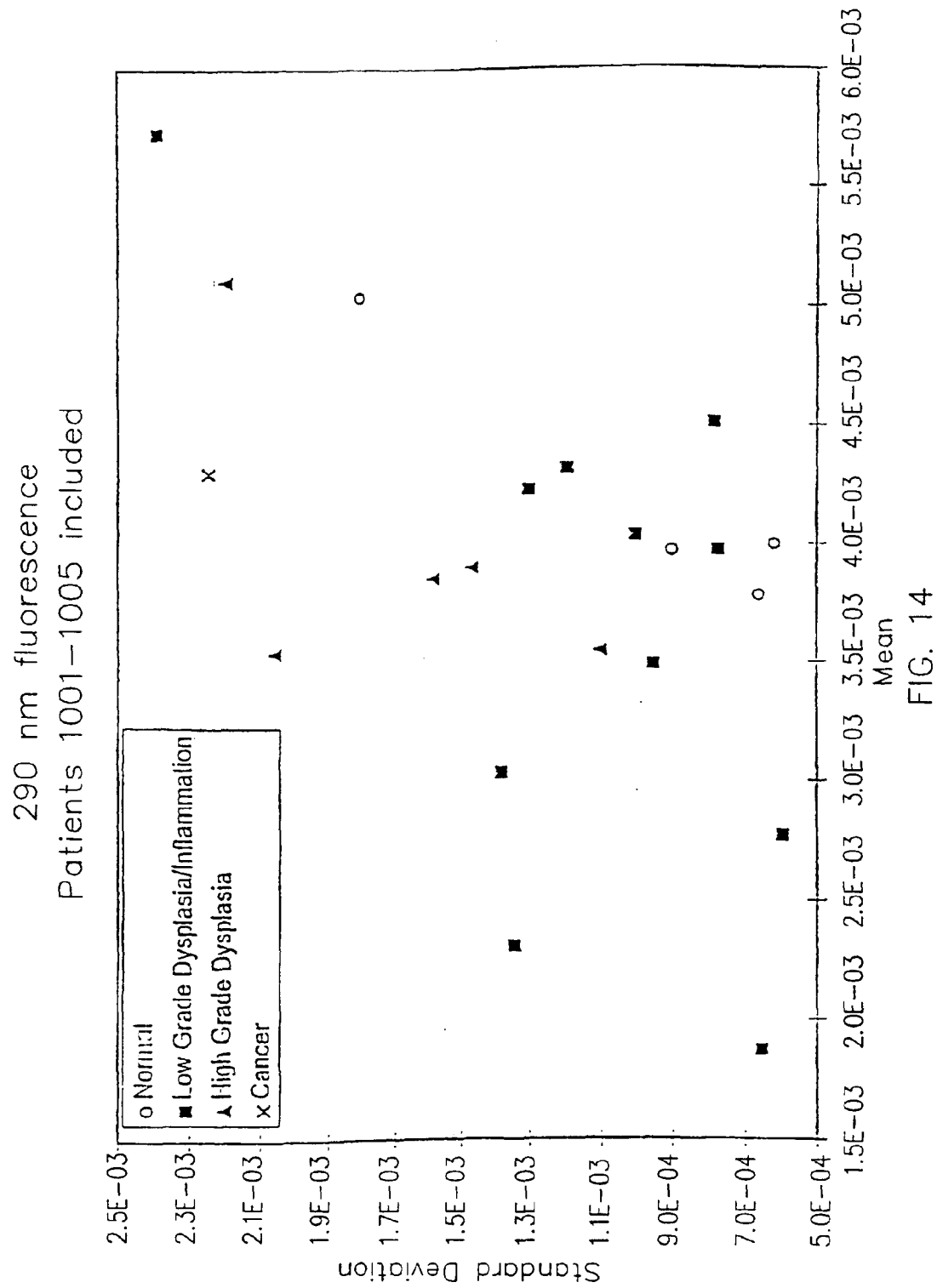
Figure 15:
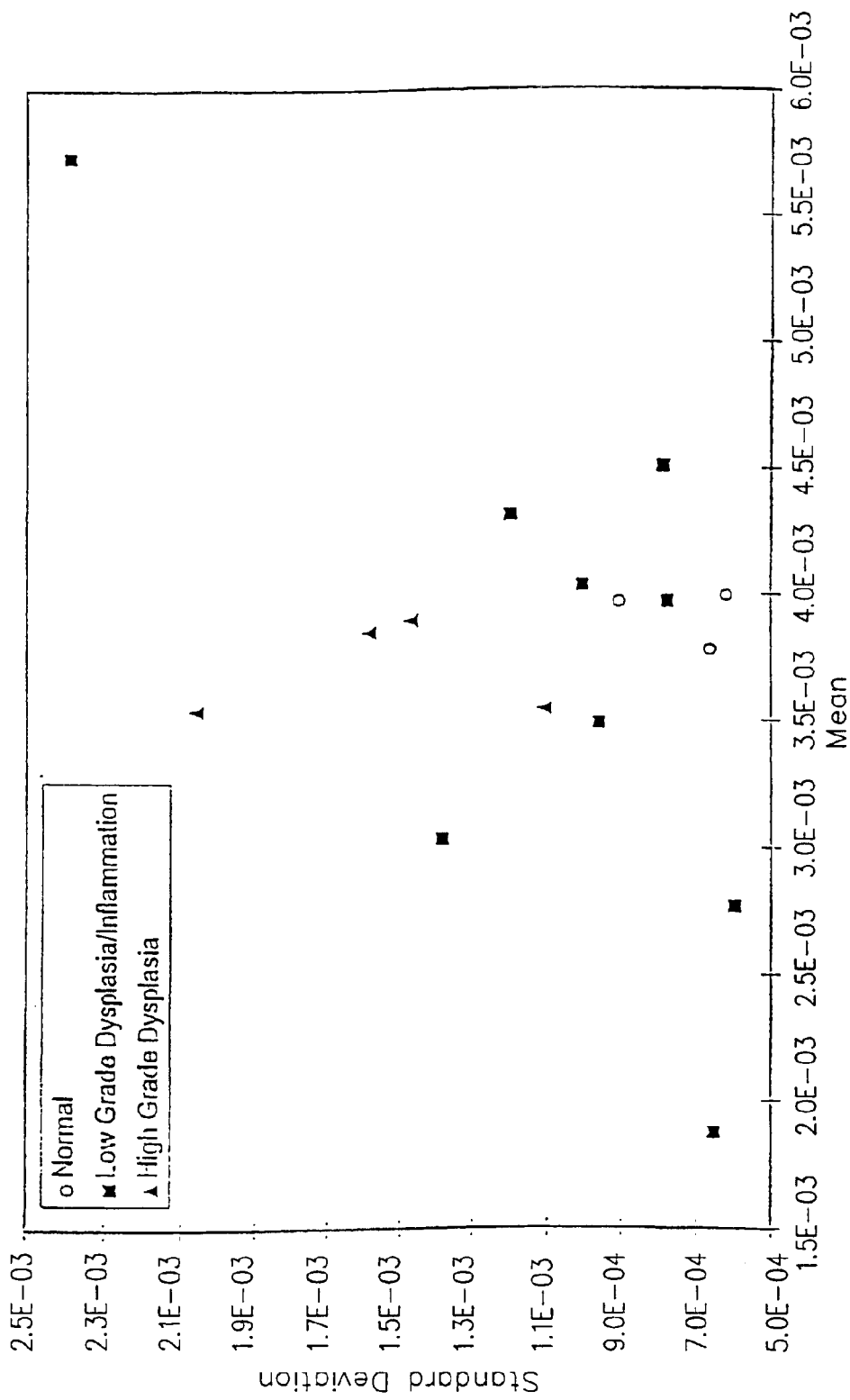
Figure 16:
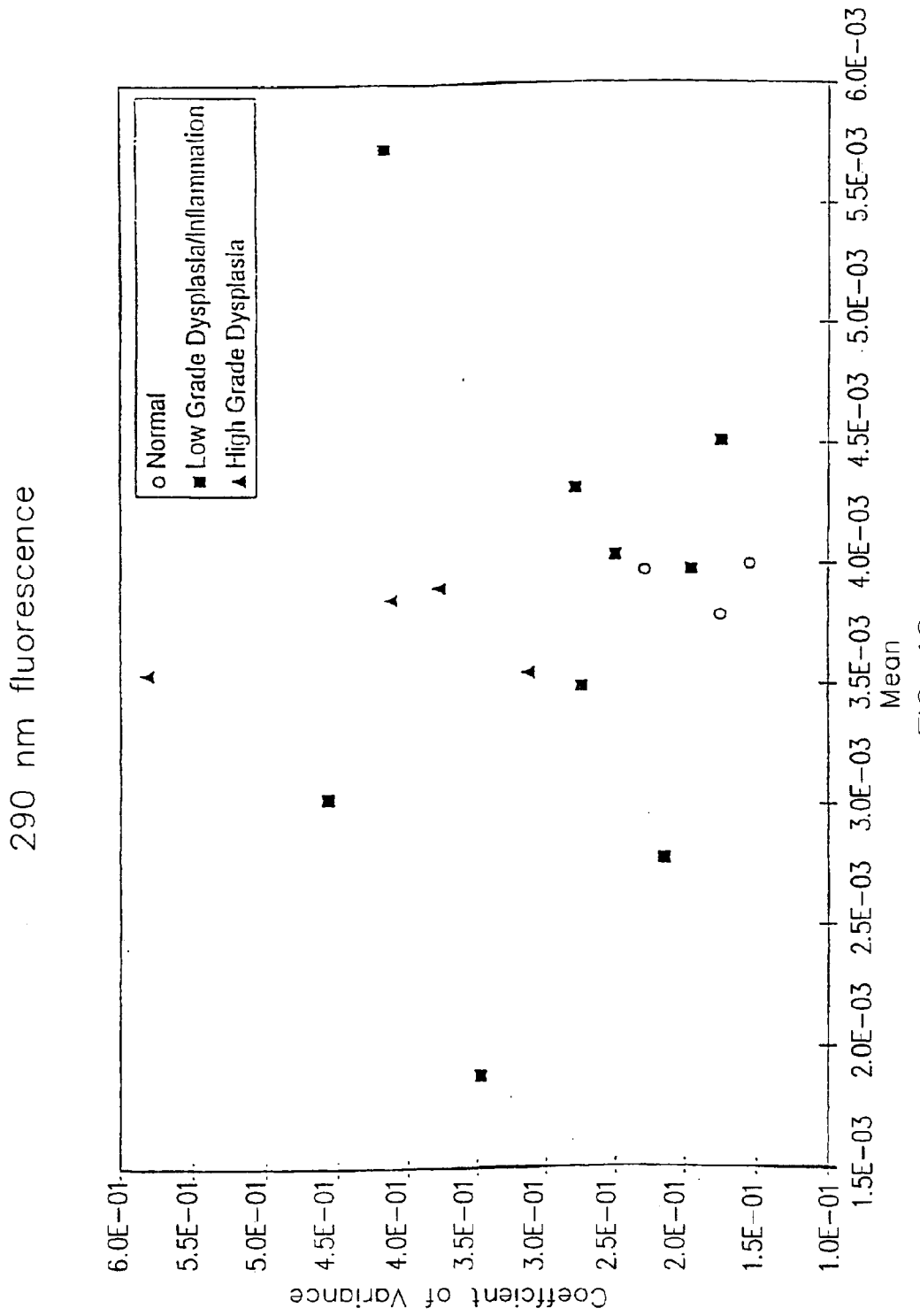
Figure 17:
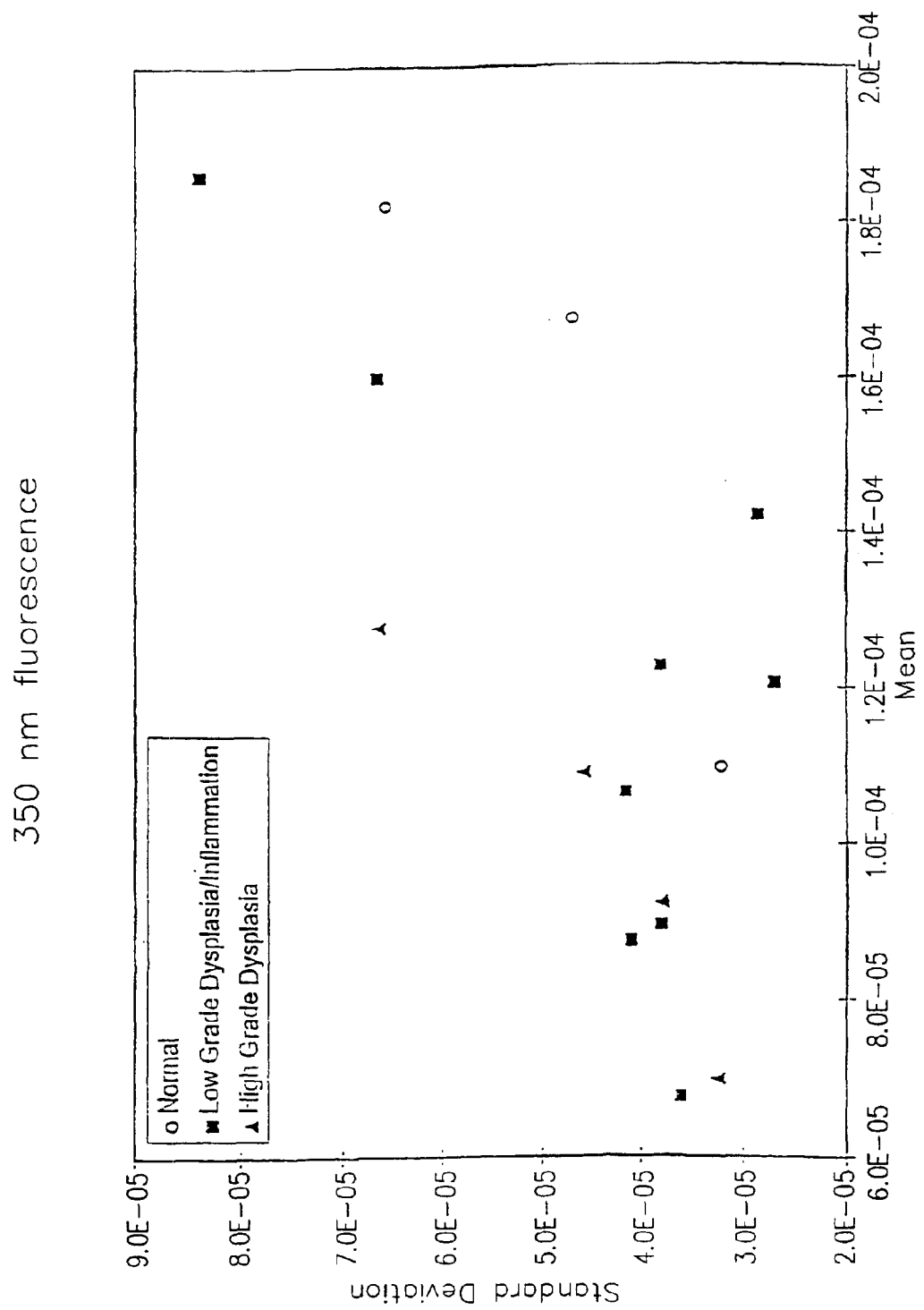
Figure 18:
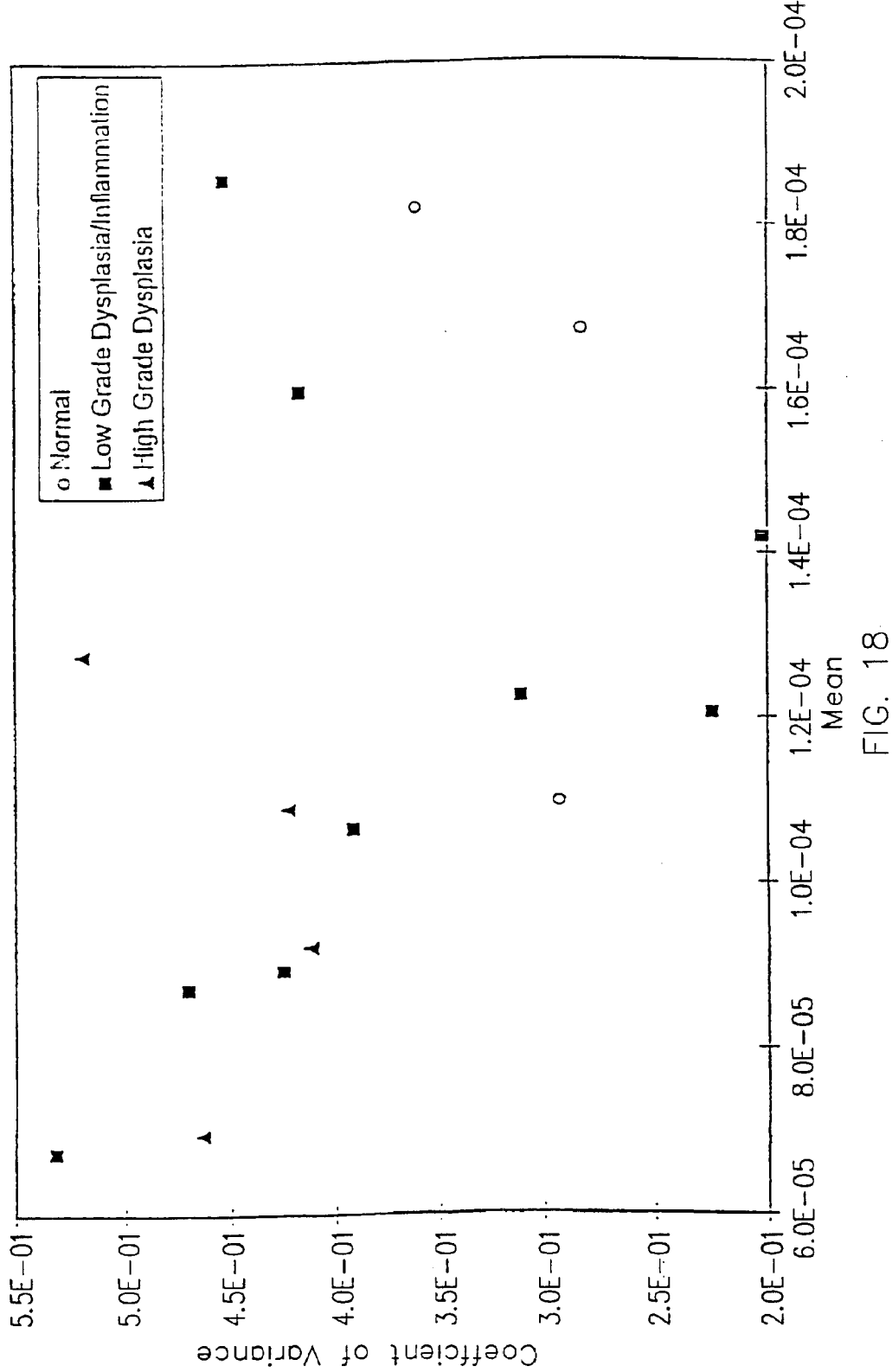
Figure 19:
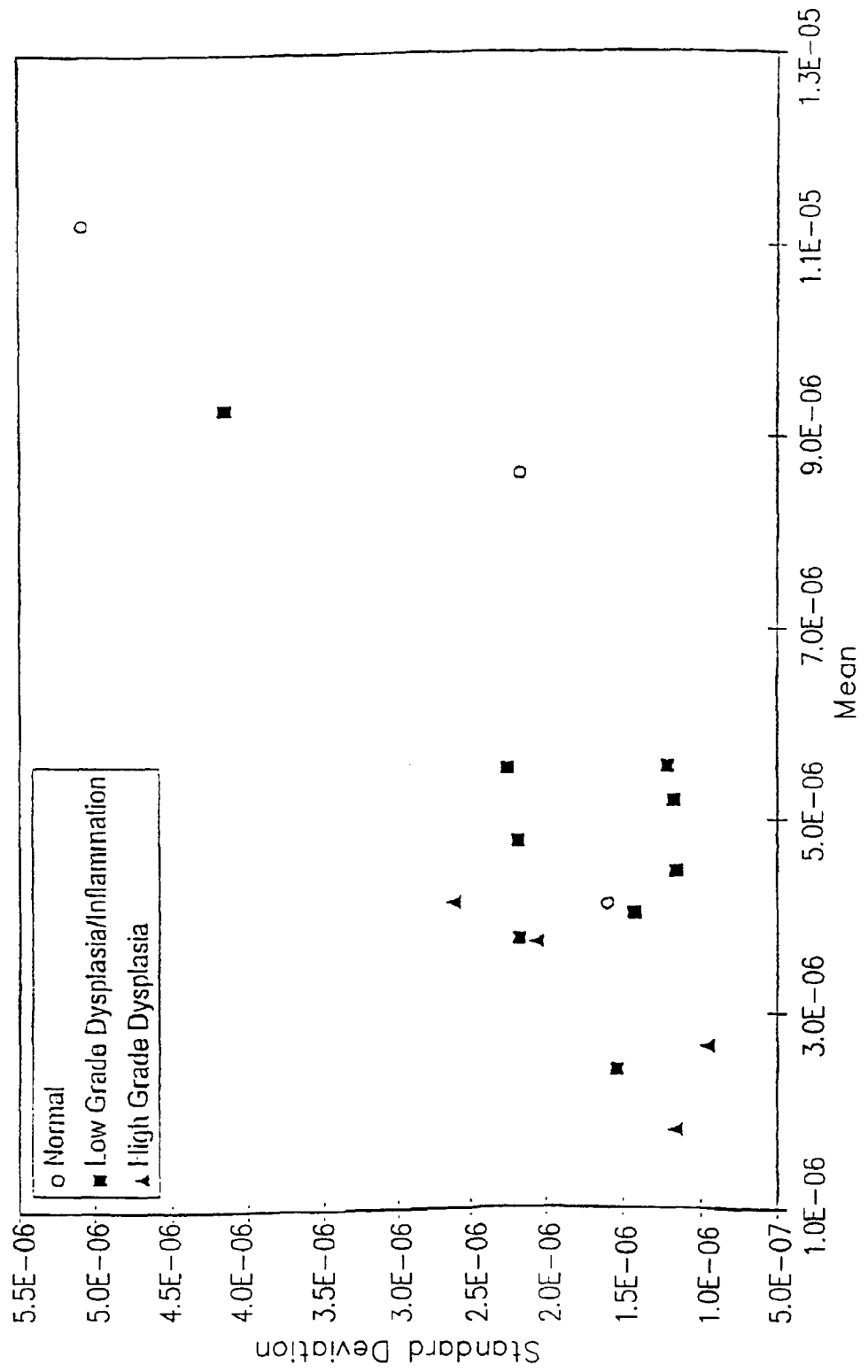
Figure 20:
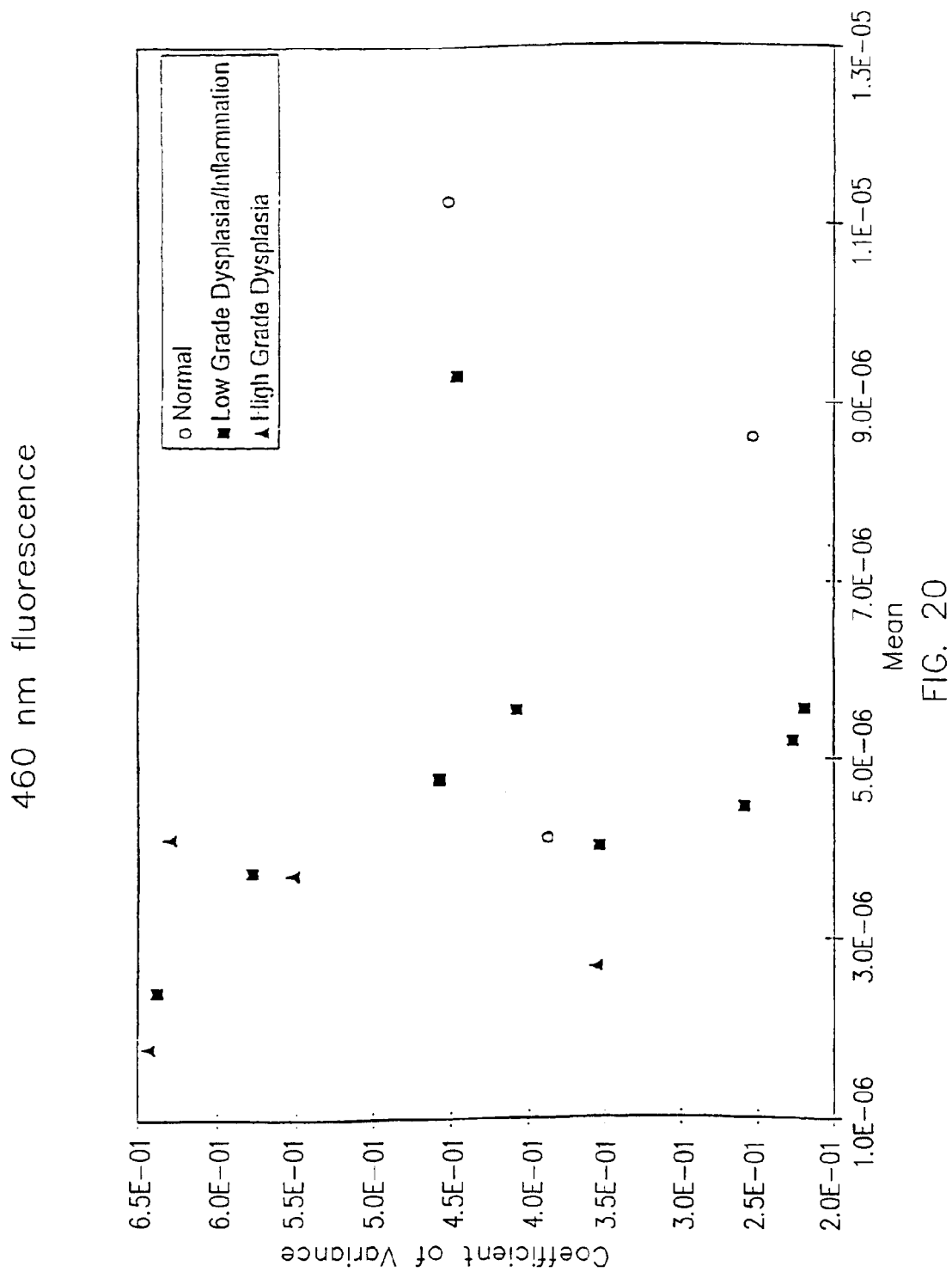
Figure 21:
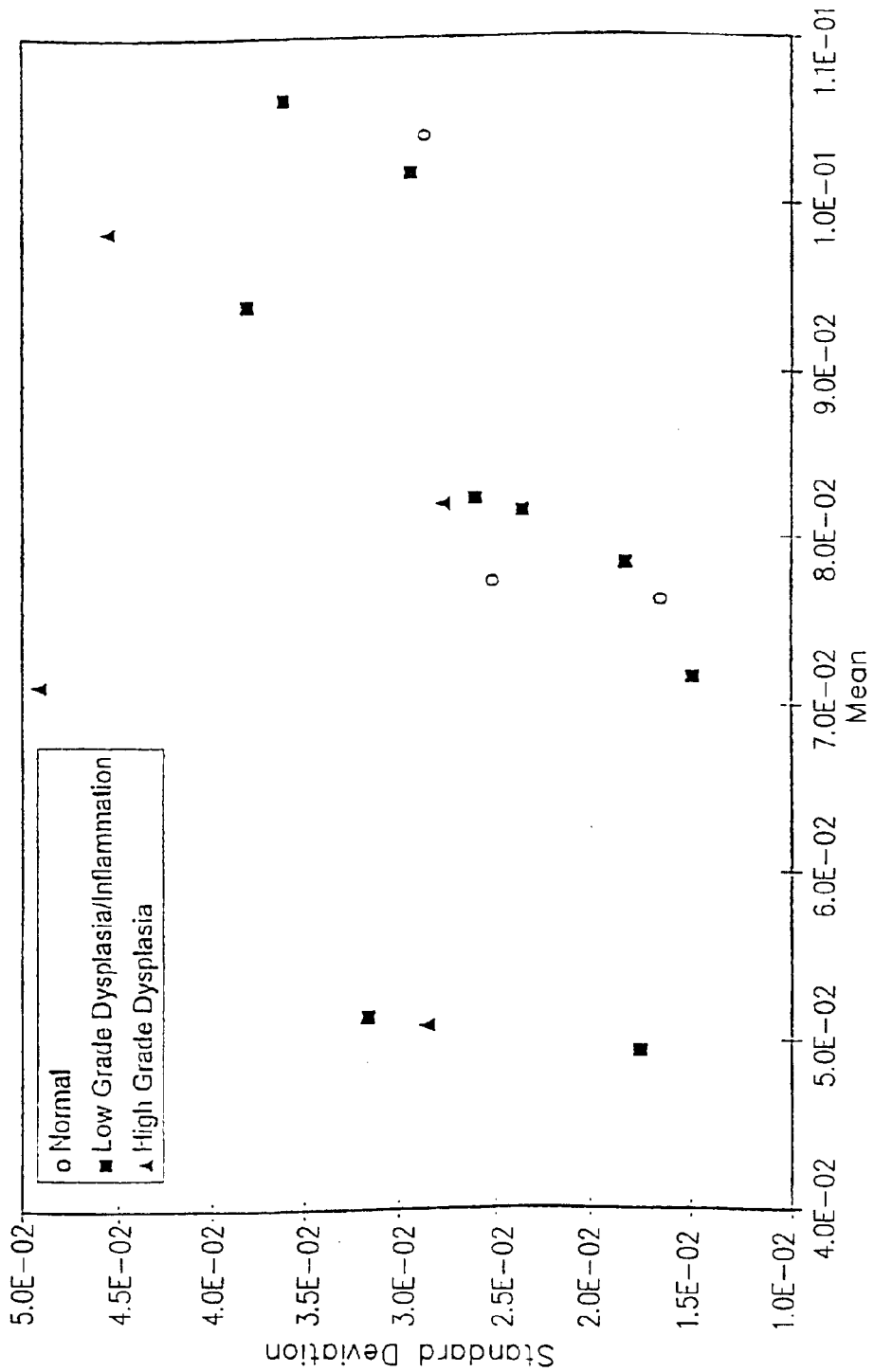
Figure 22:
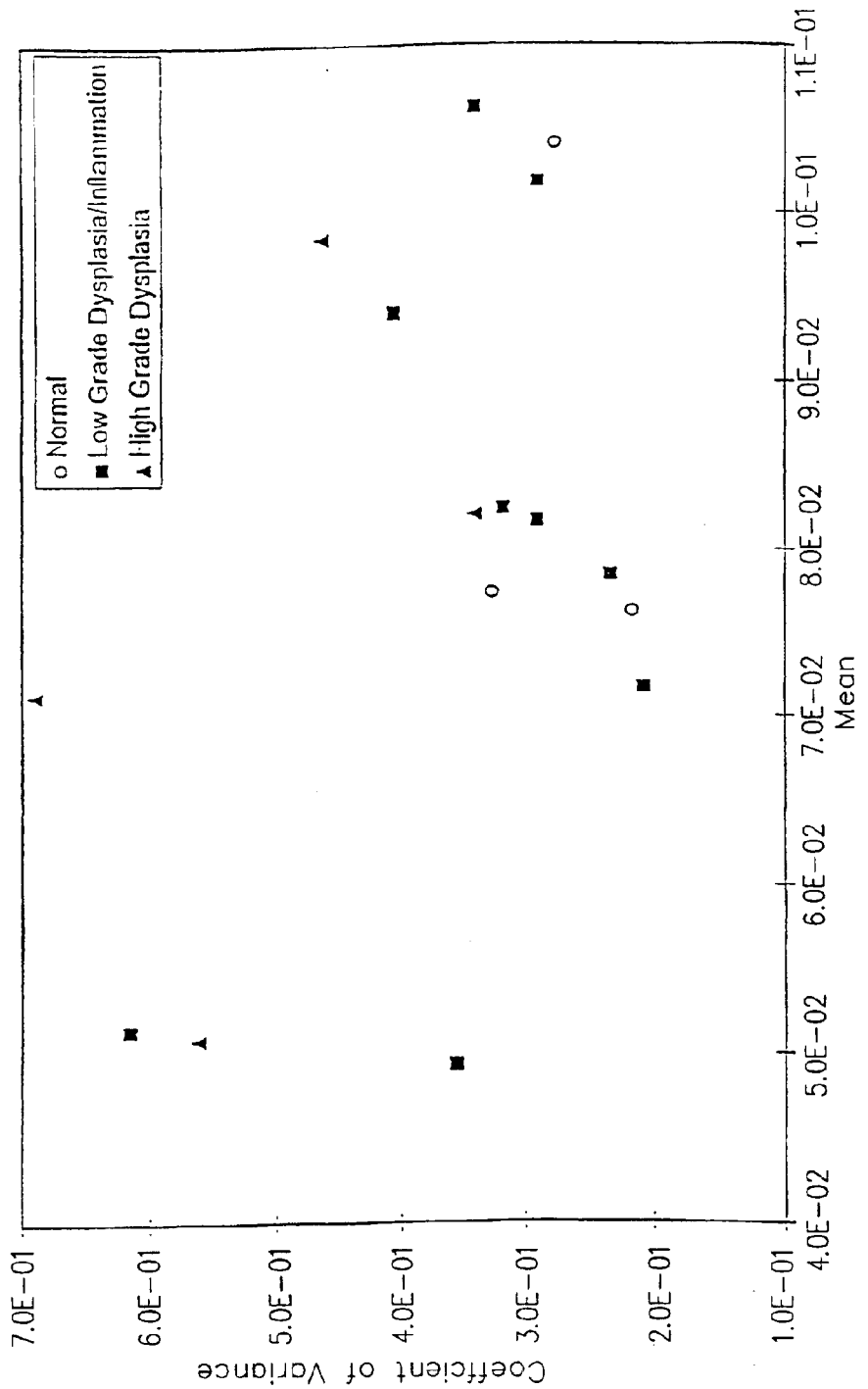
Figure 23:
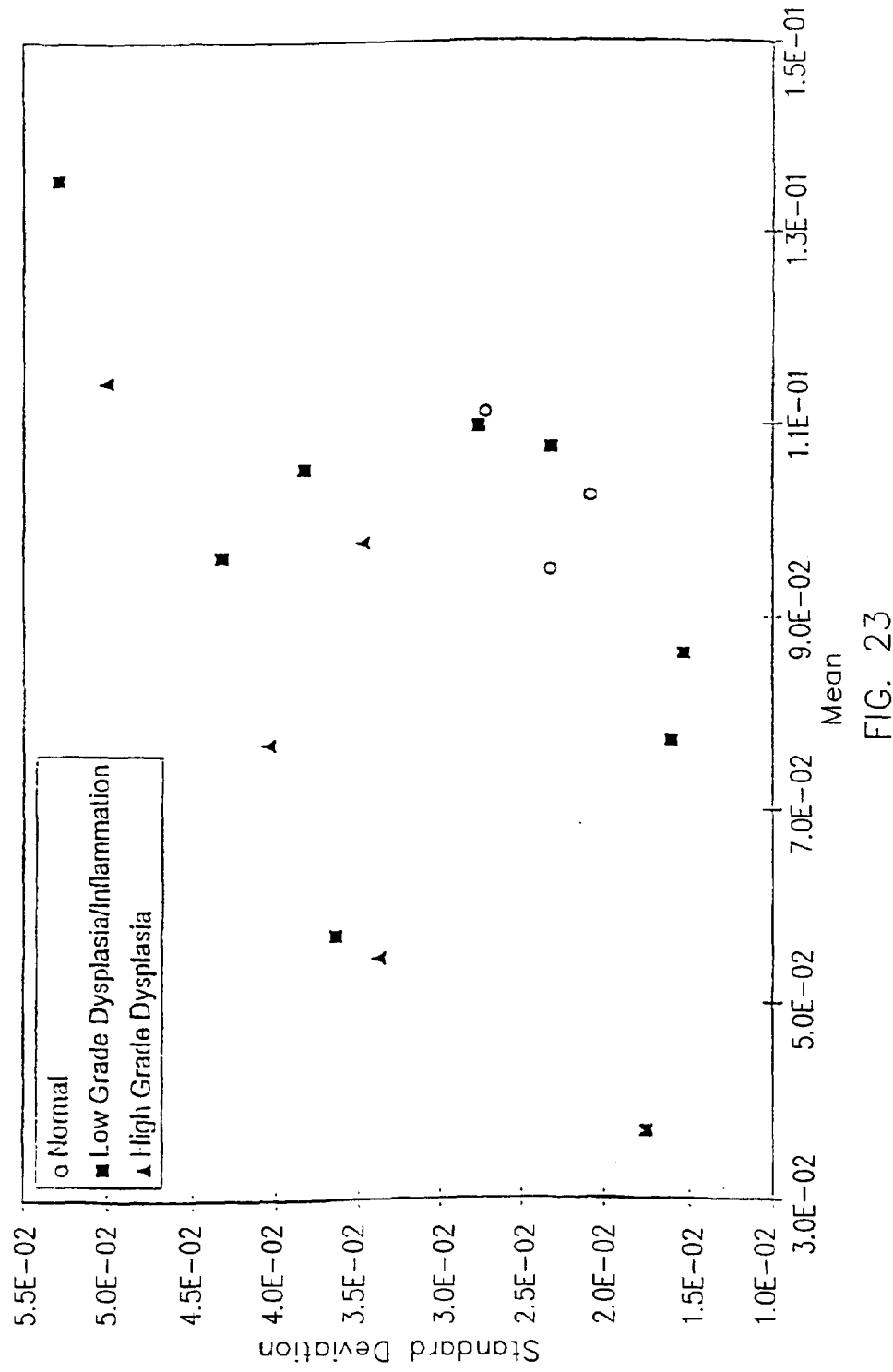
Figure 24:
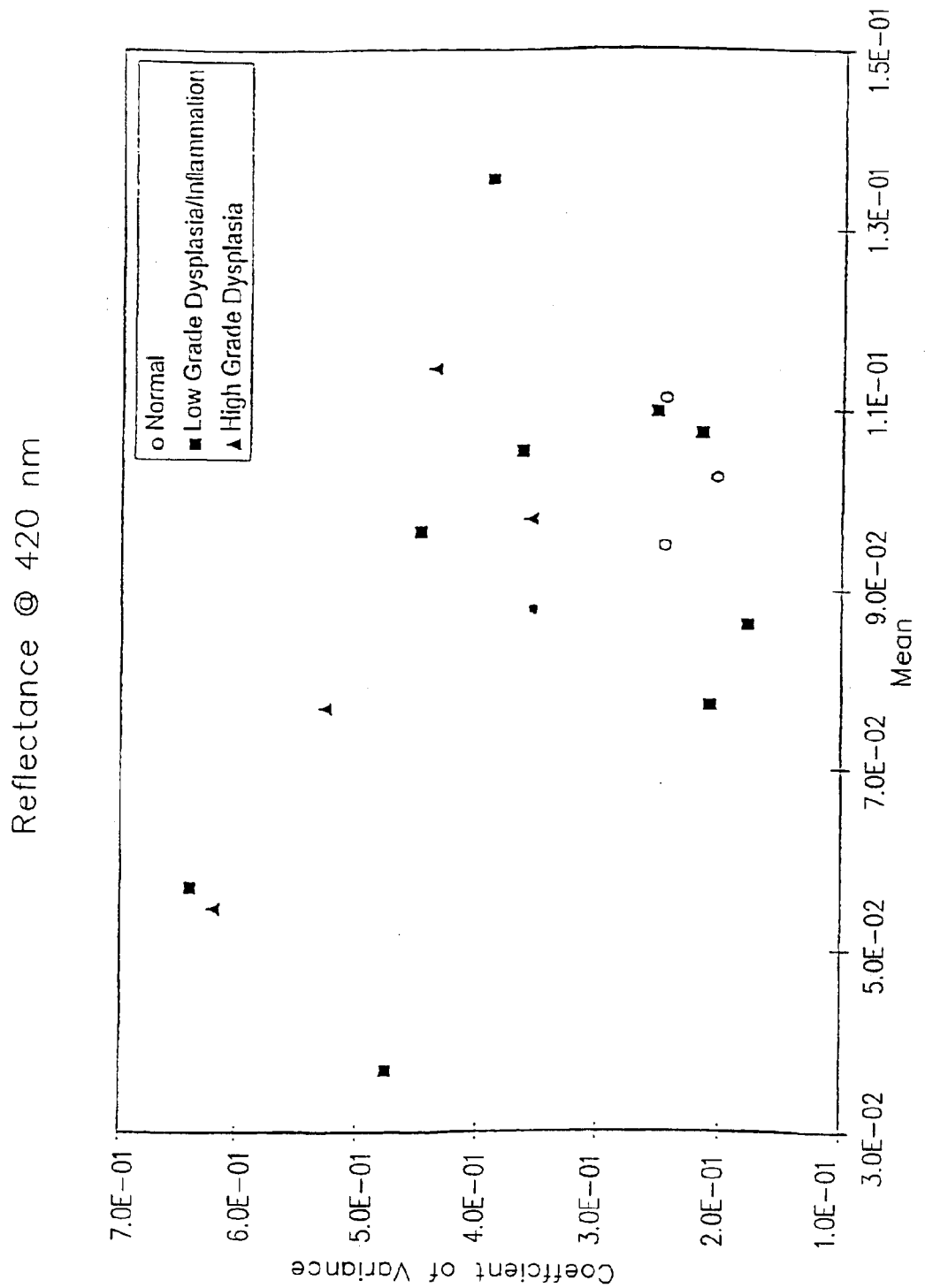
Figure 25:
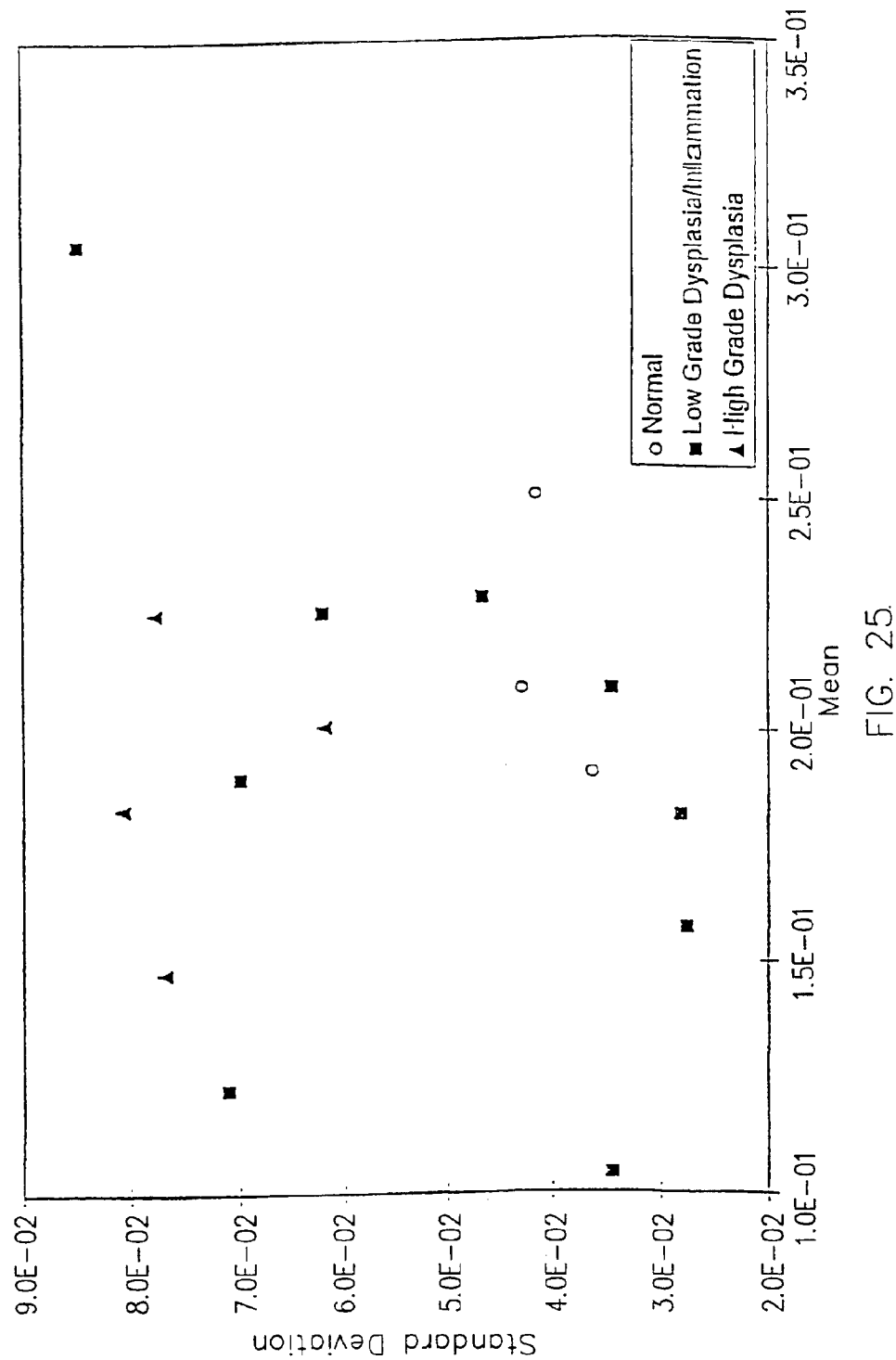
Figure 26:
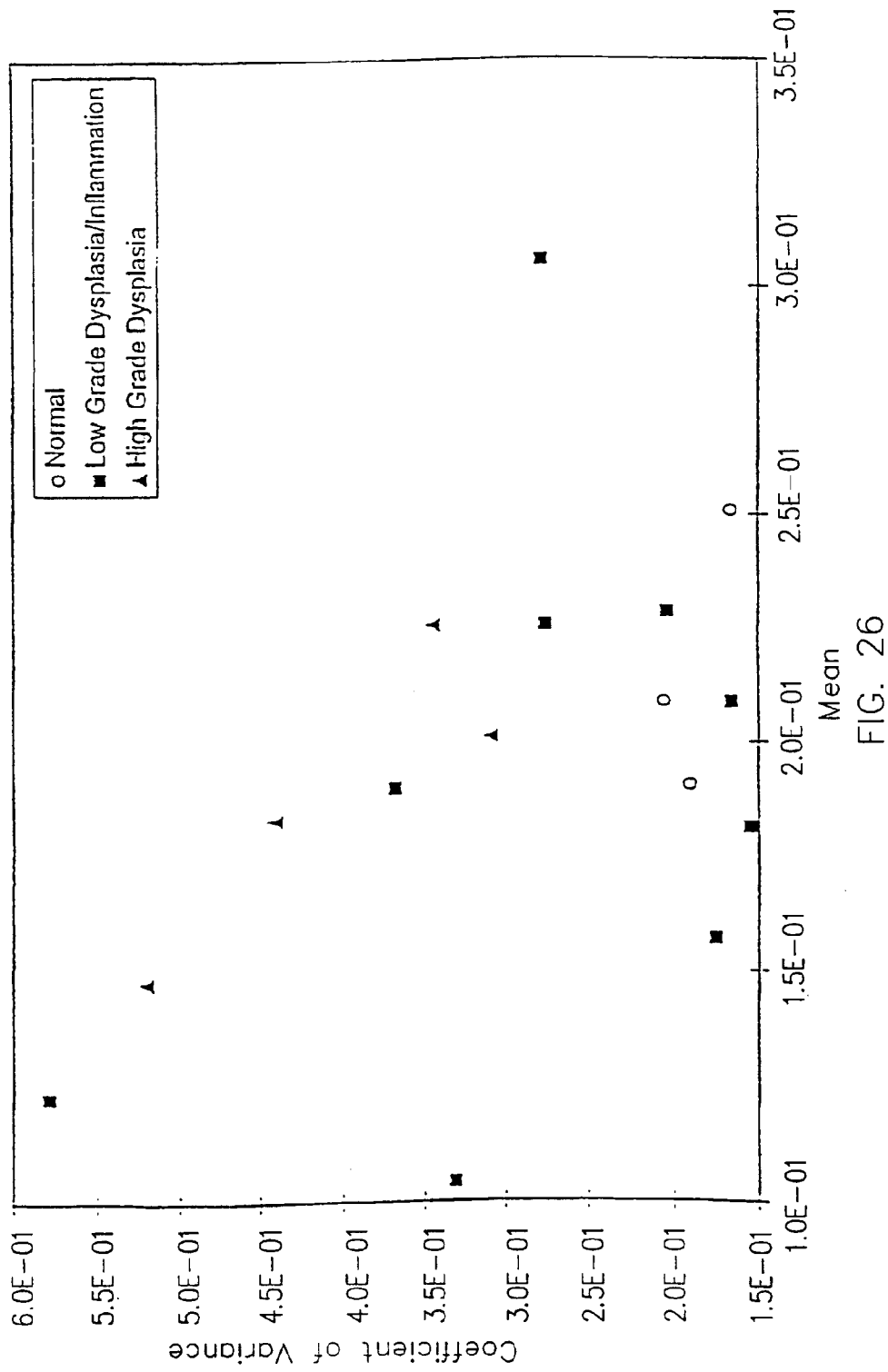
Figure 27:
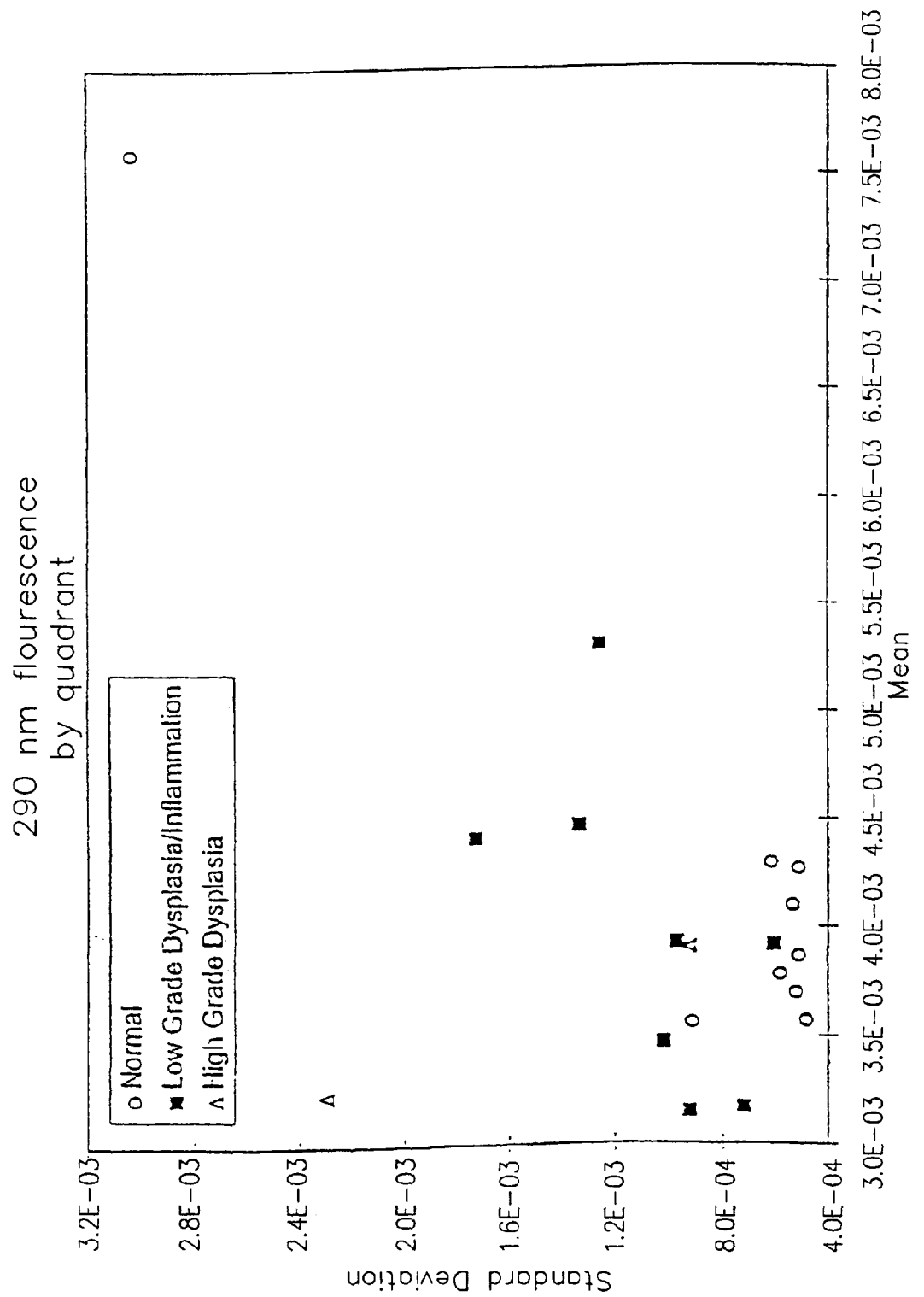
Figure 28:
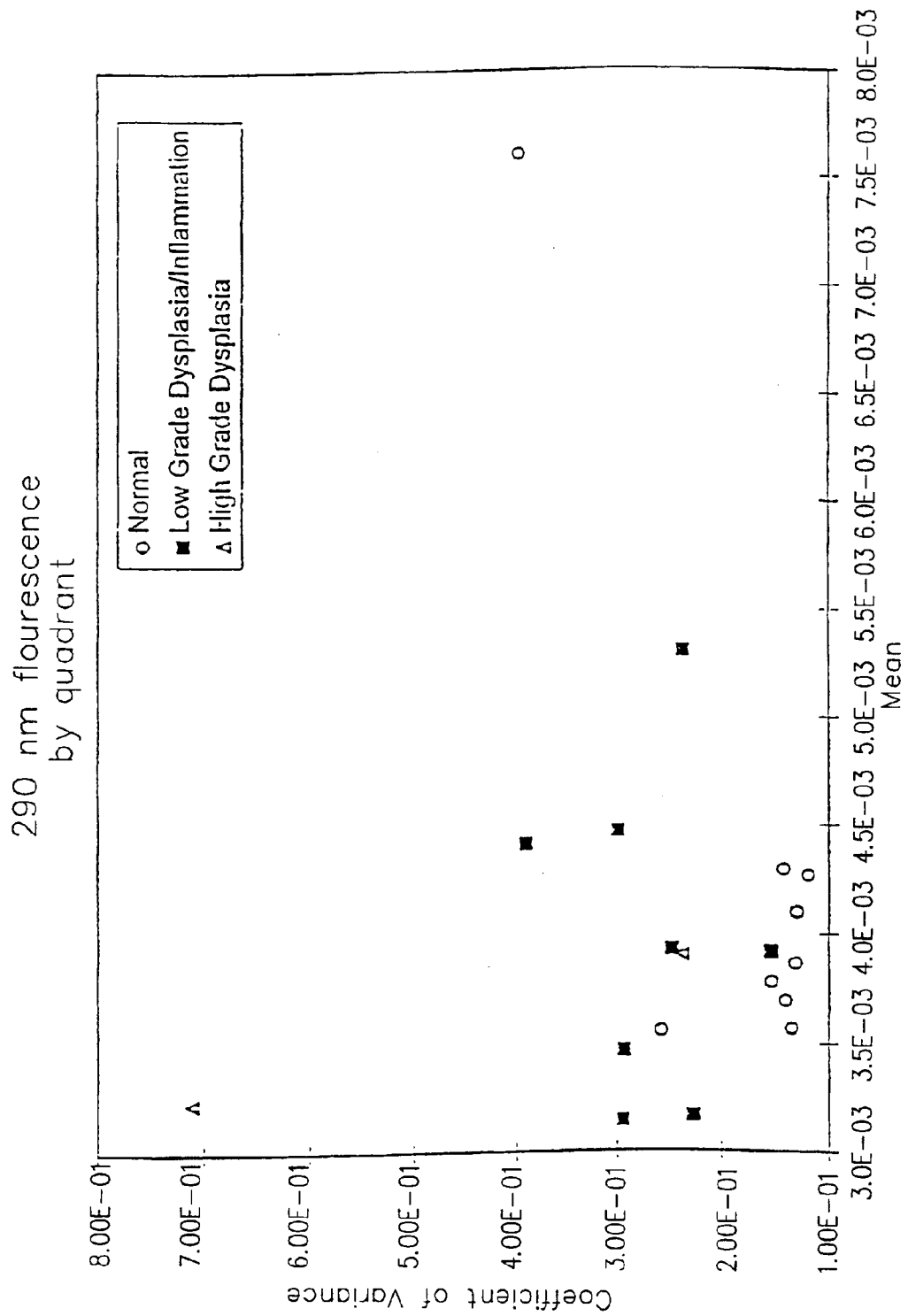
Figure 29:
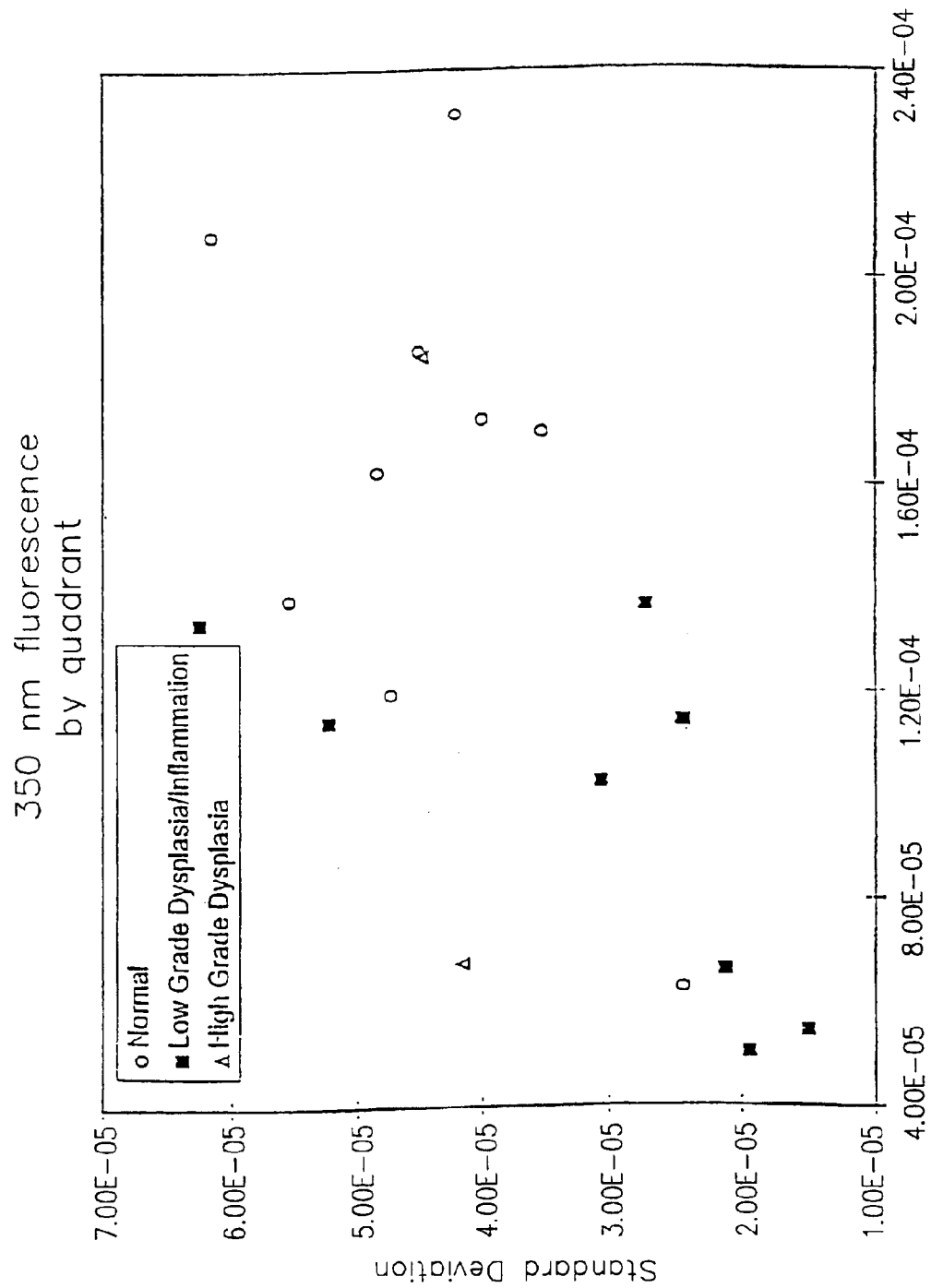
Figure 30:
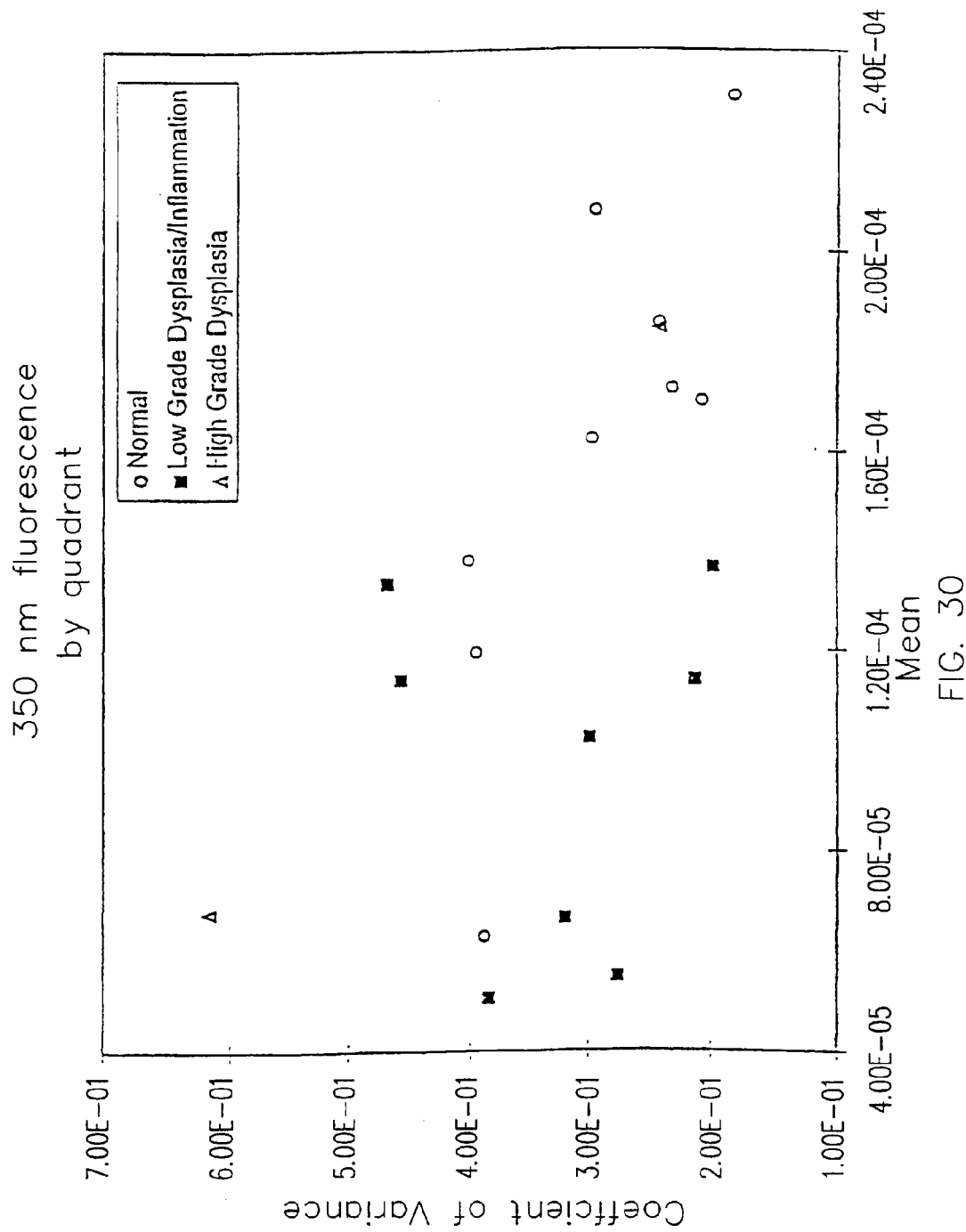
Figure 31:
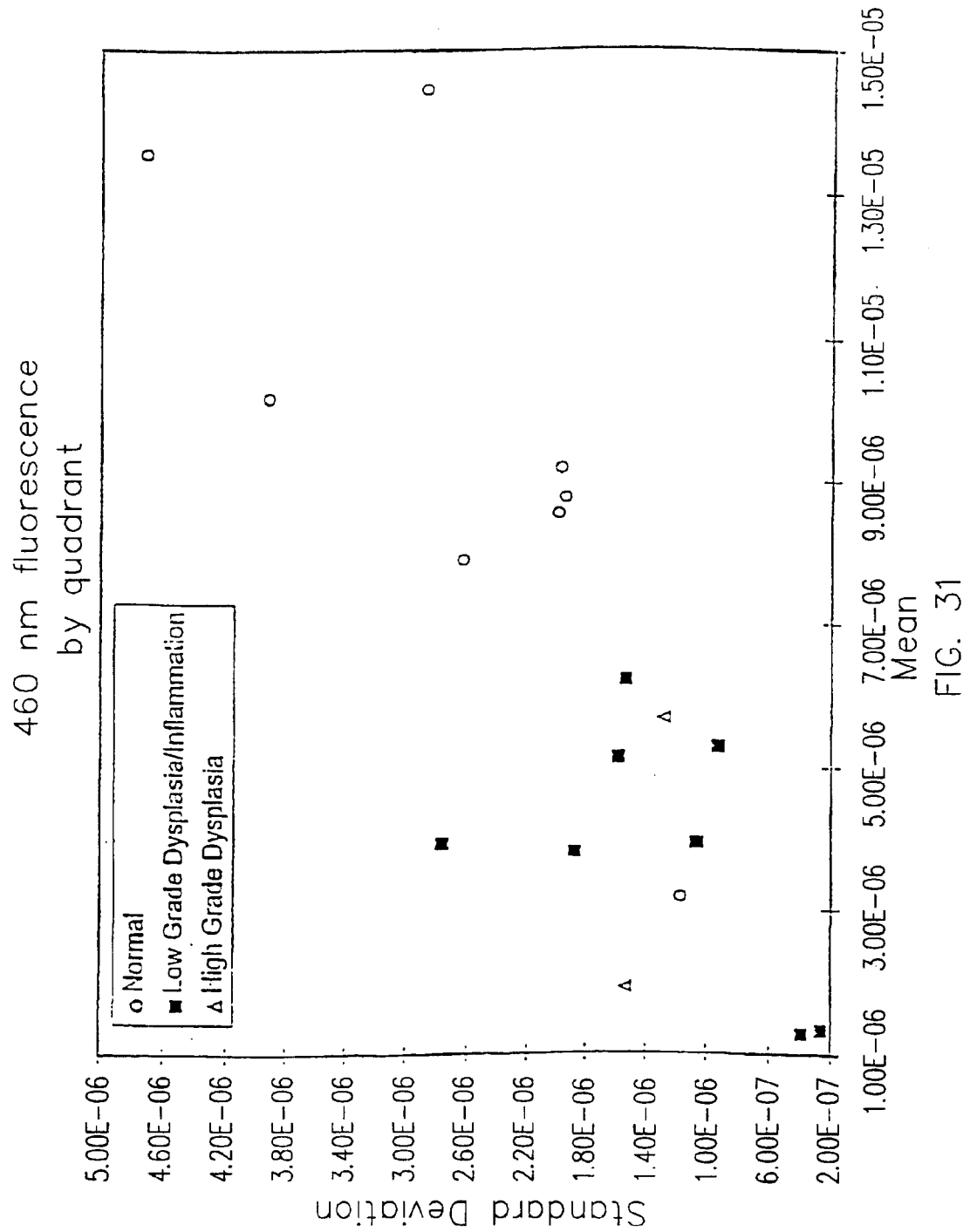
Figure 32:
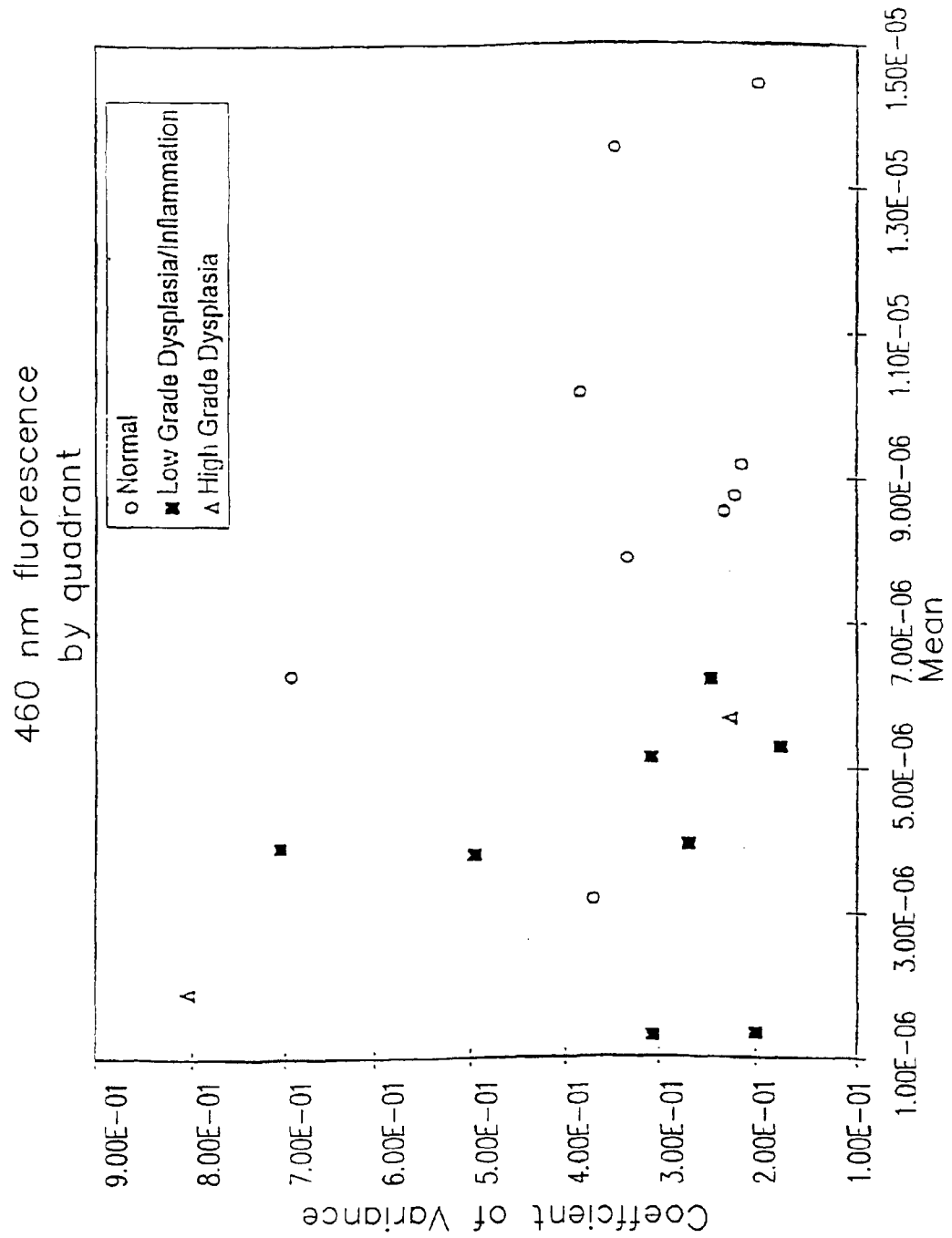
Figure 33:
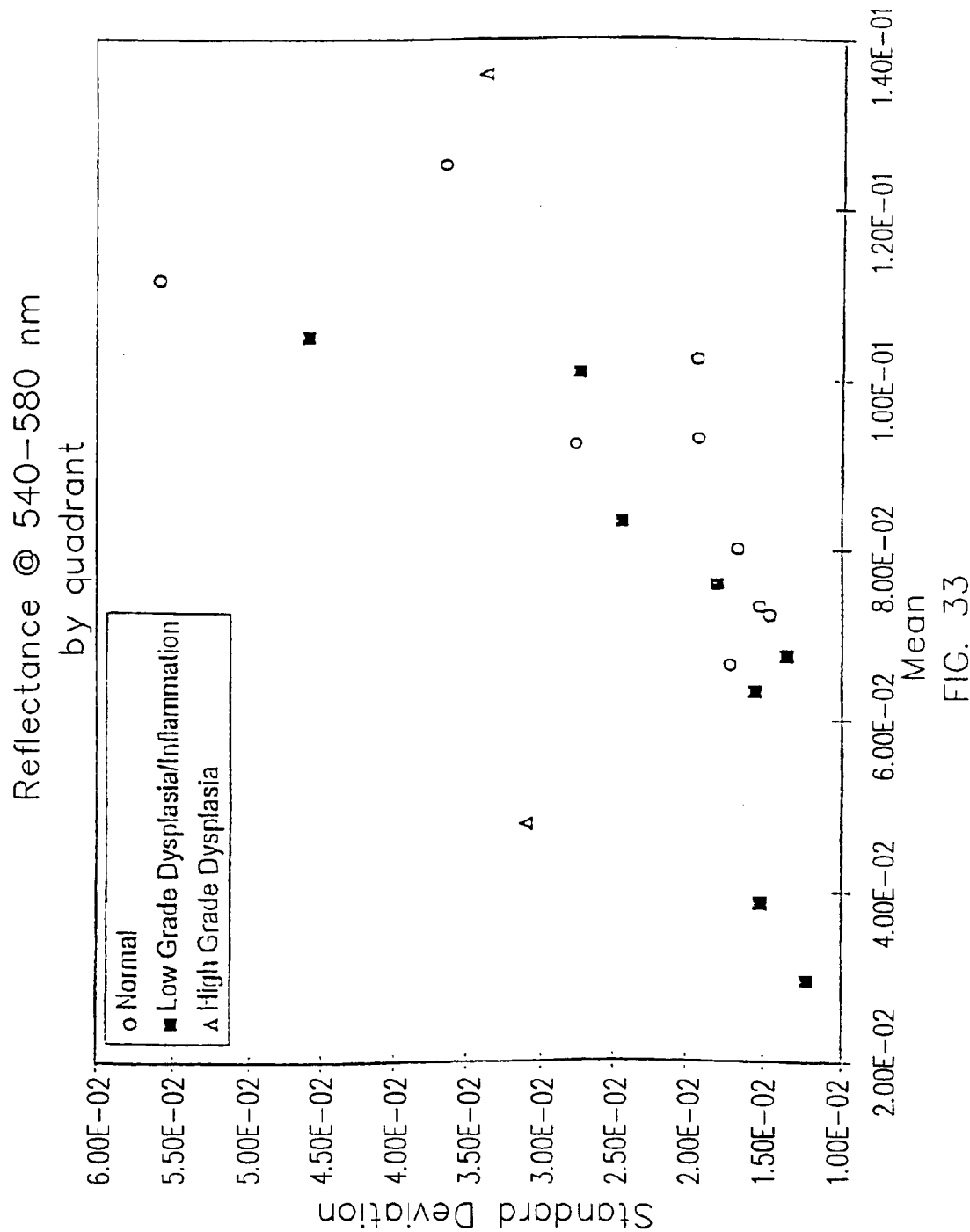
Figure 34:
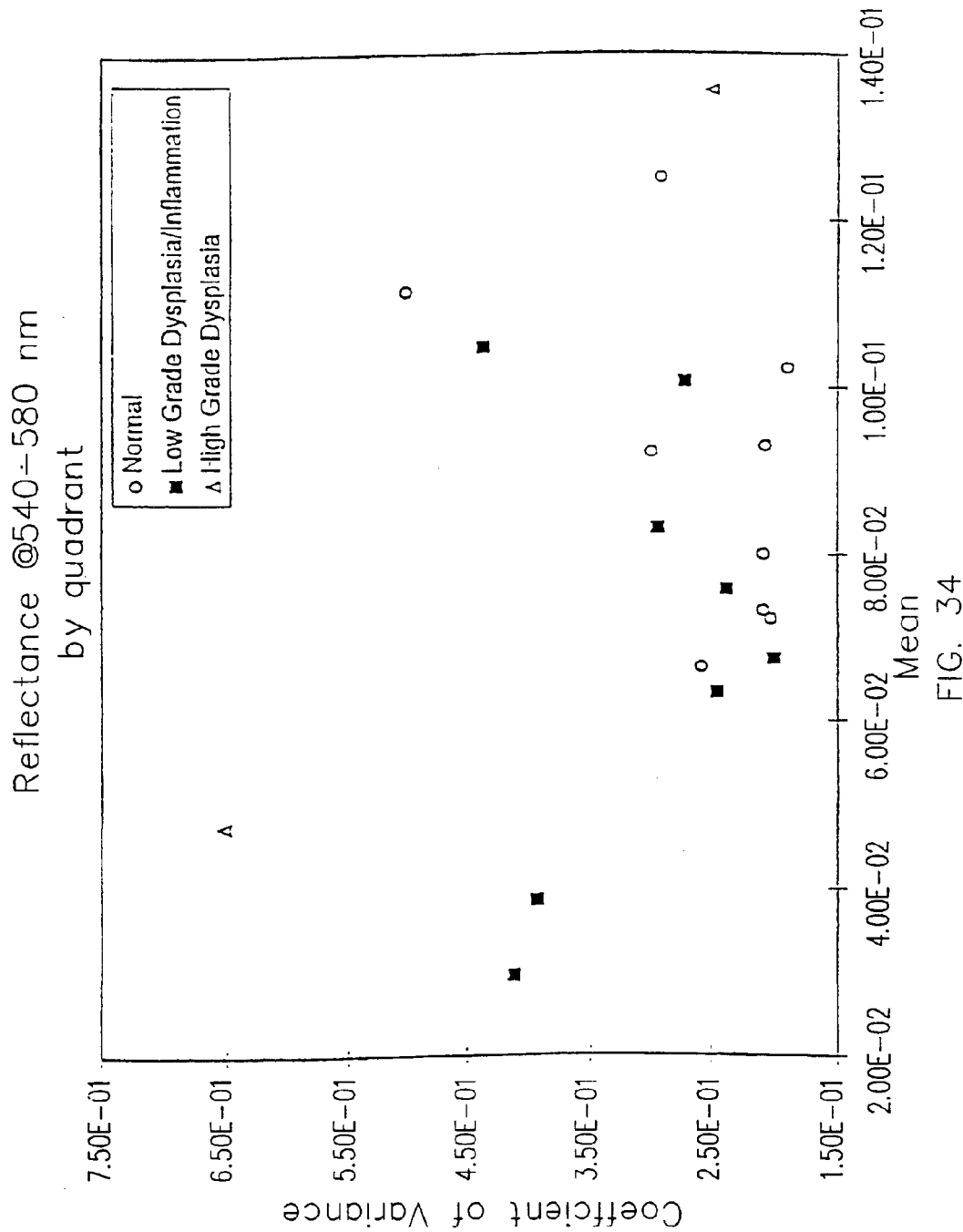
Figure 35:
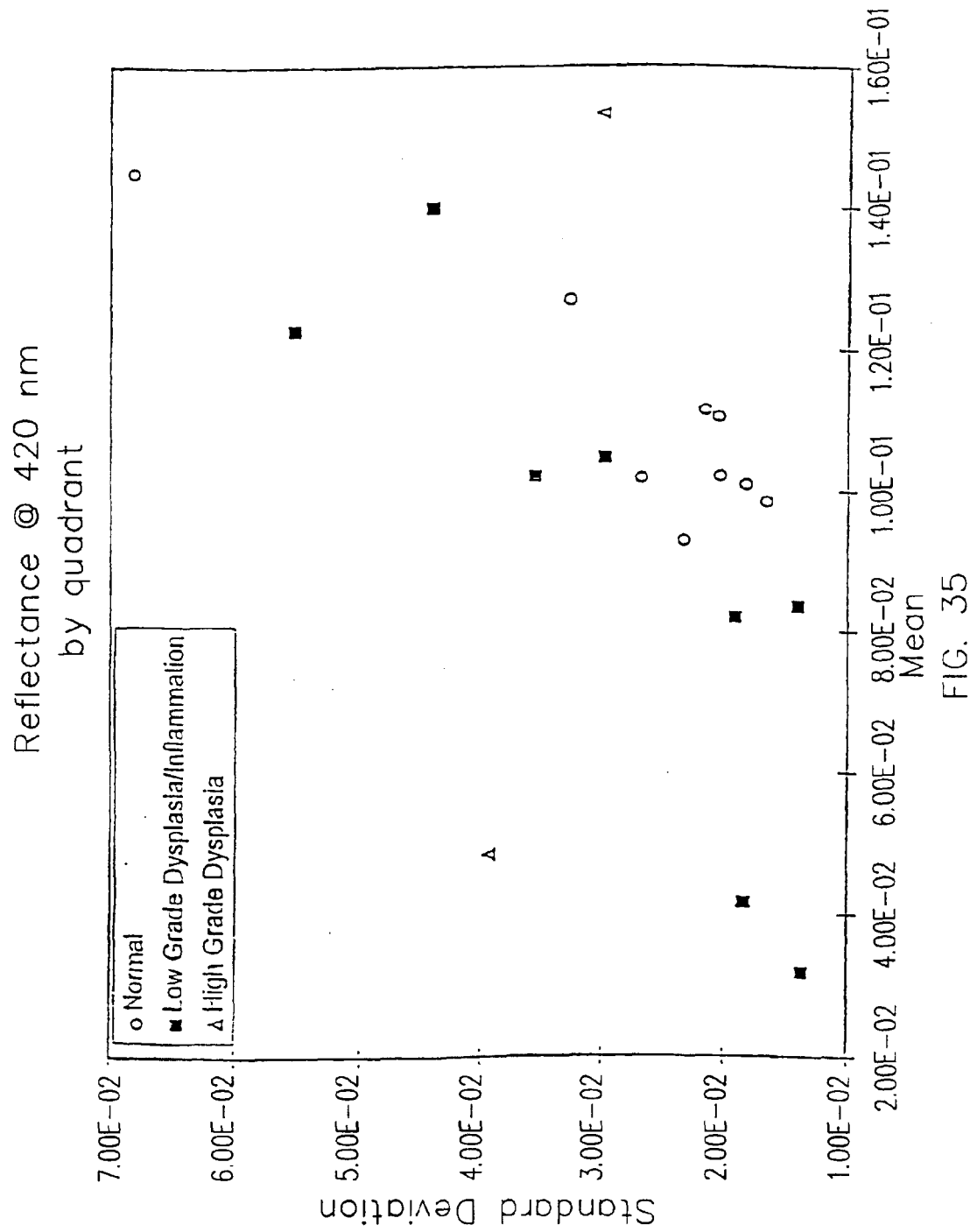
Figure 36:
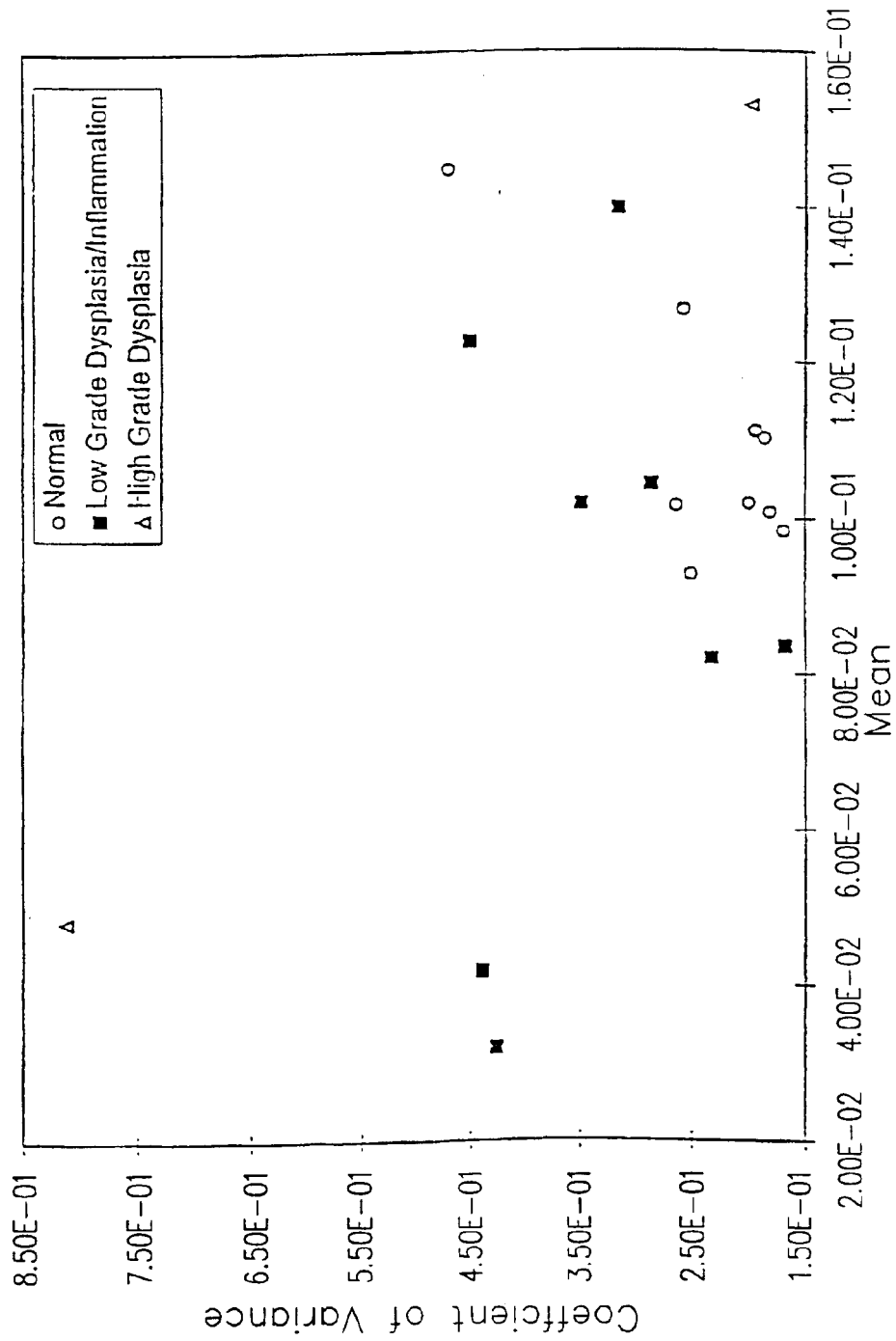
Figure 37:
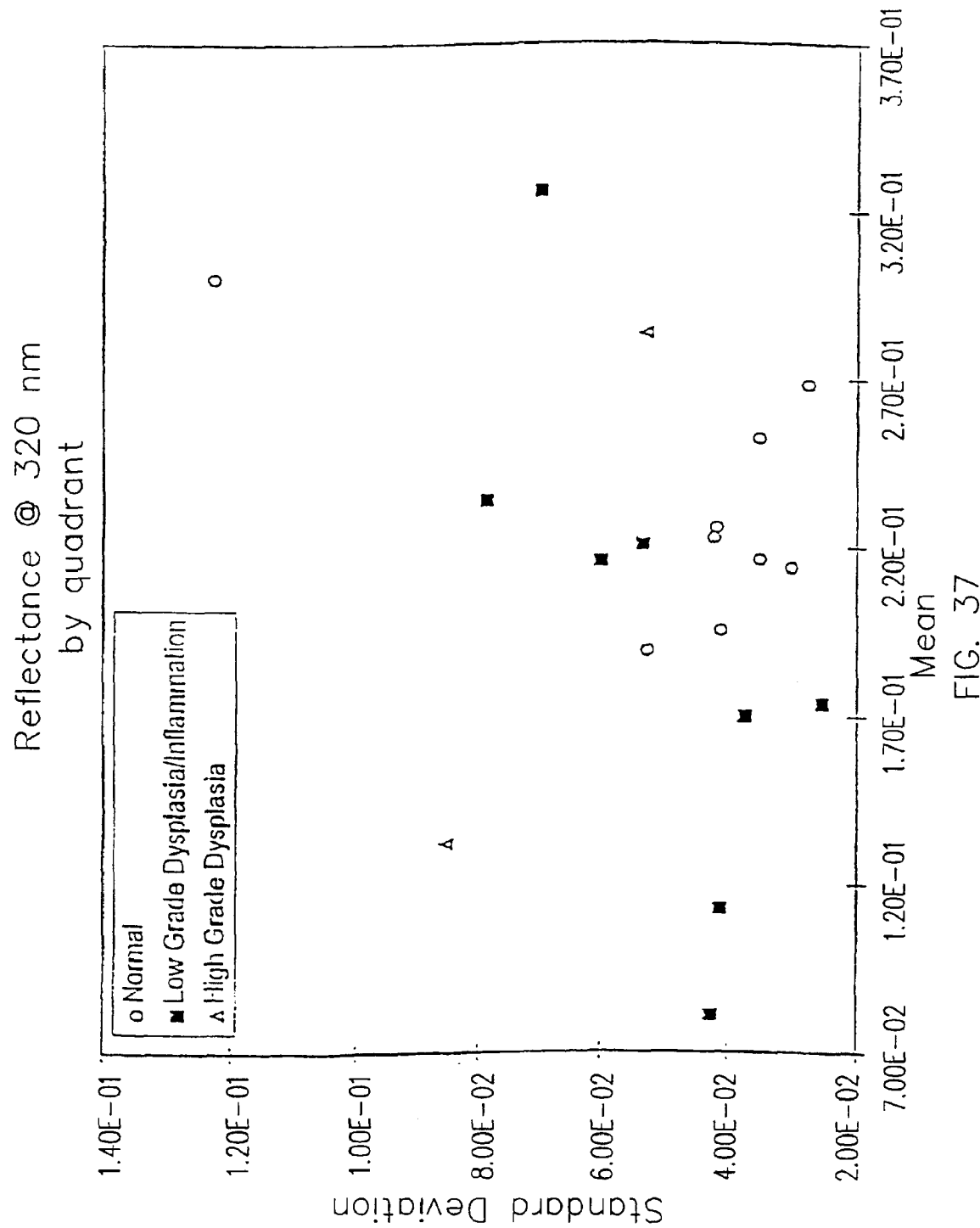
Figure 38:
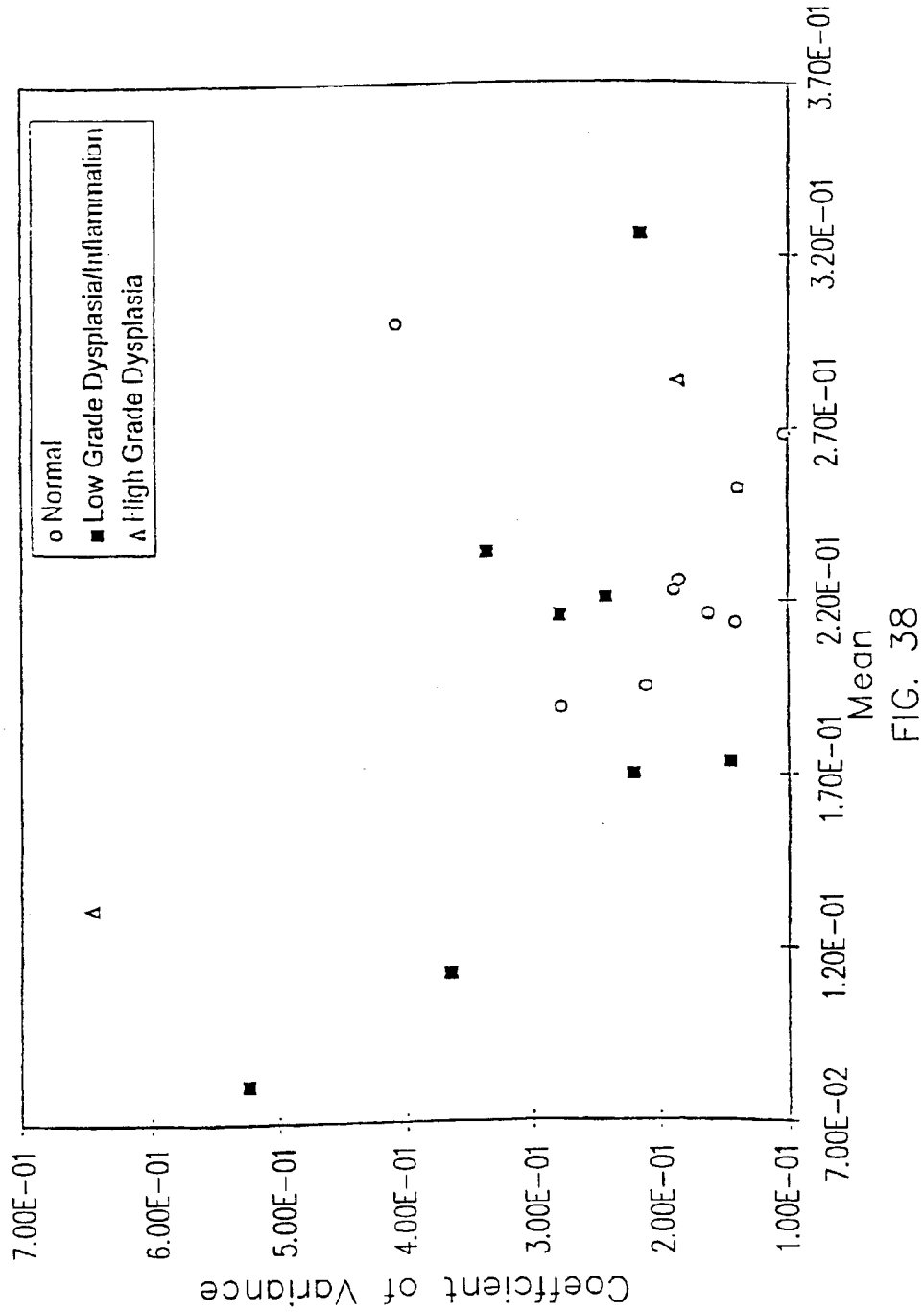
Figure 39:
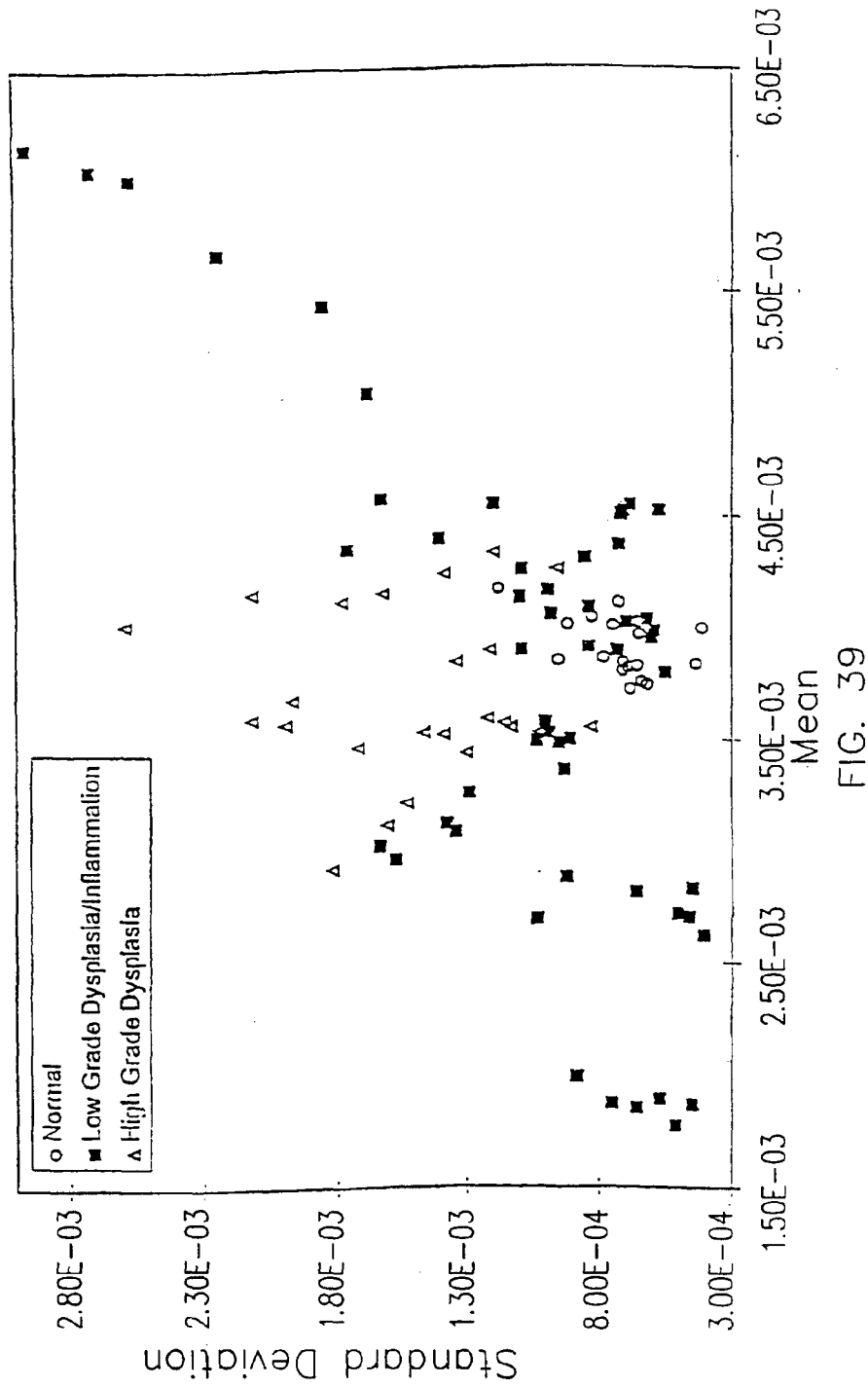
Figure 40:
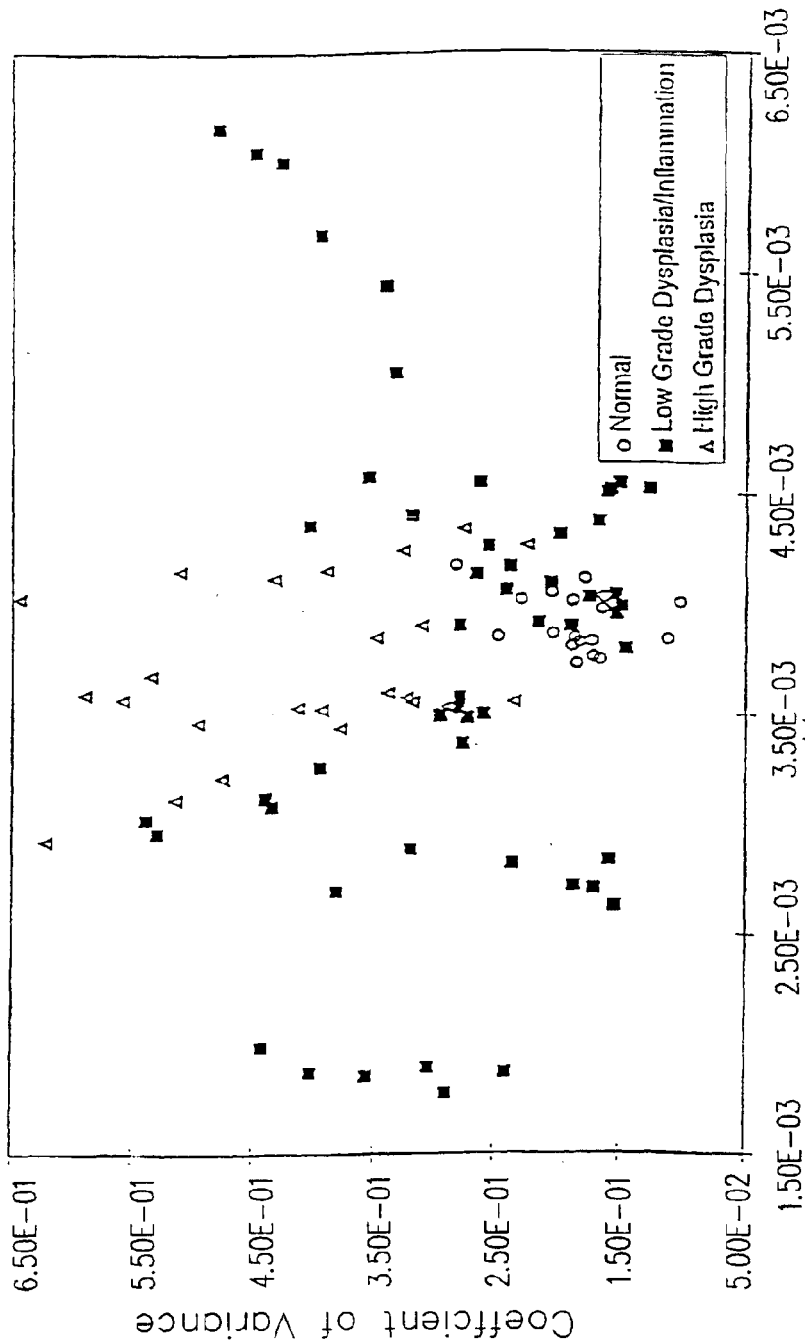
Figure 41:
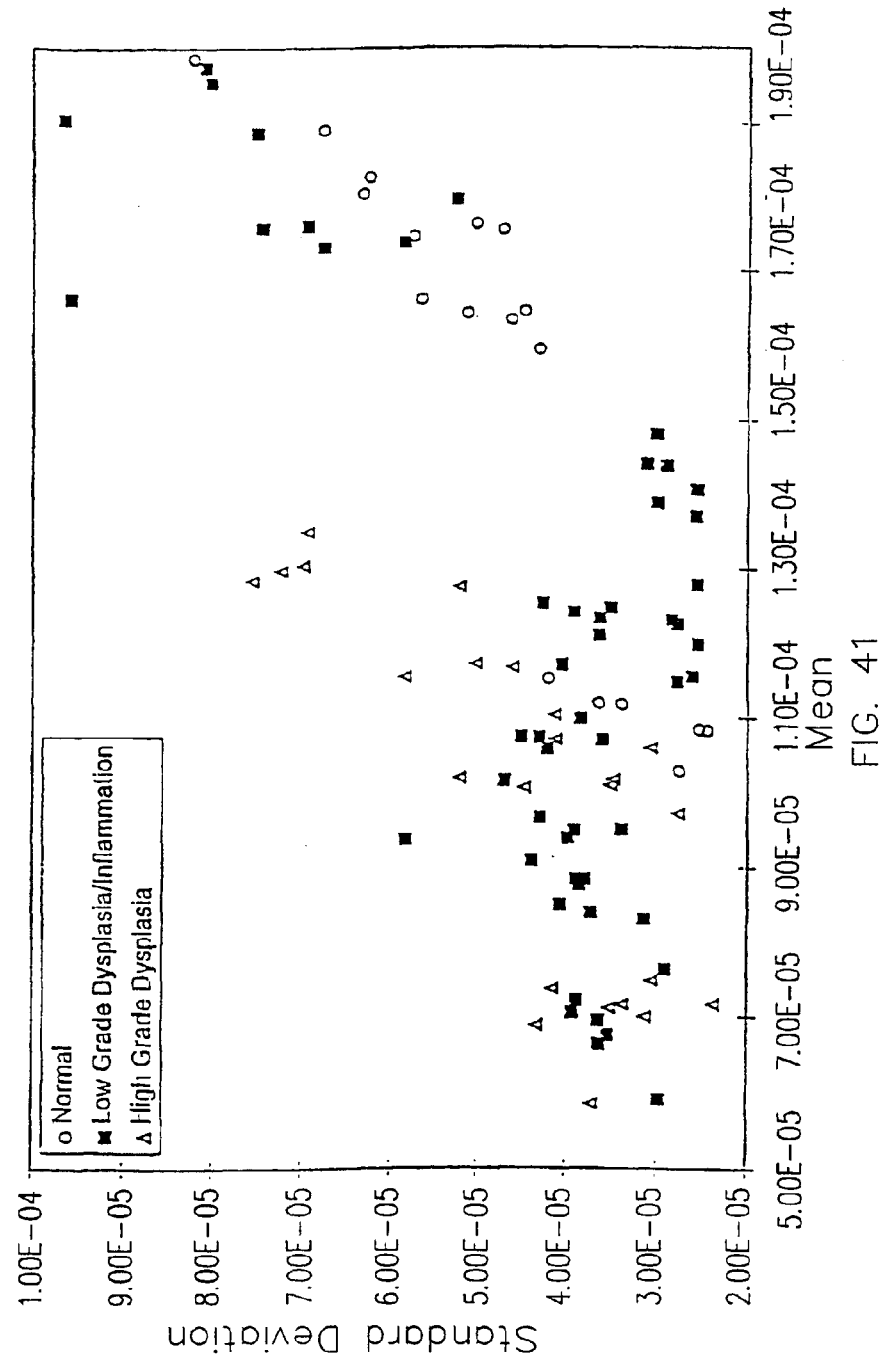
Figure 42:
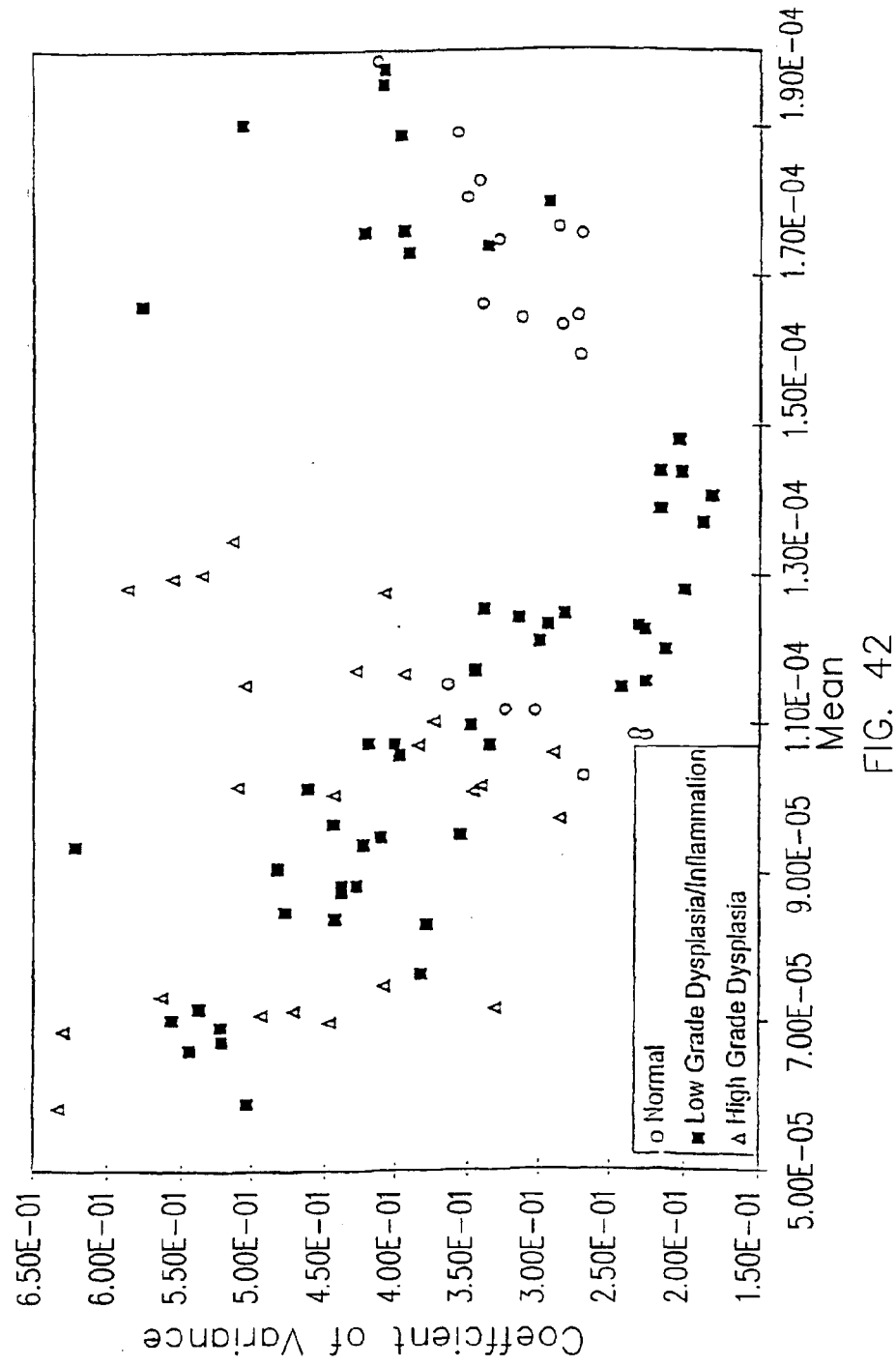
Figure 43:
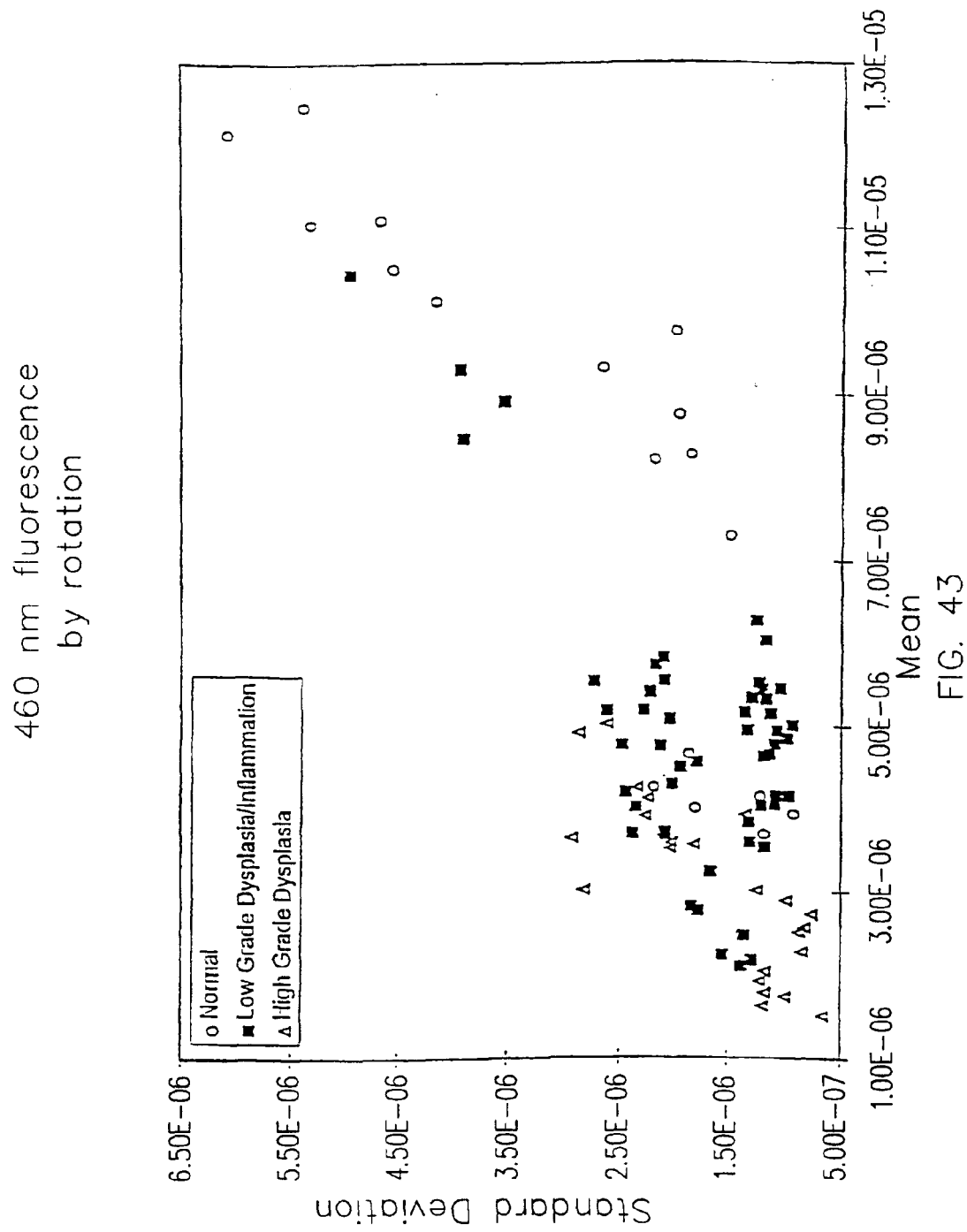
Figure 44:
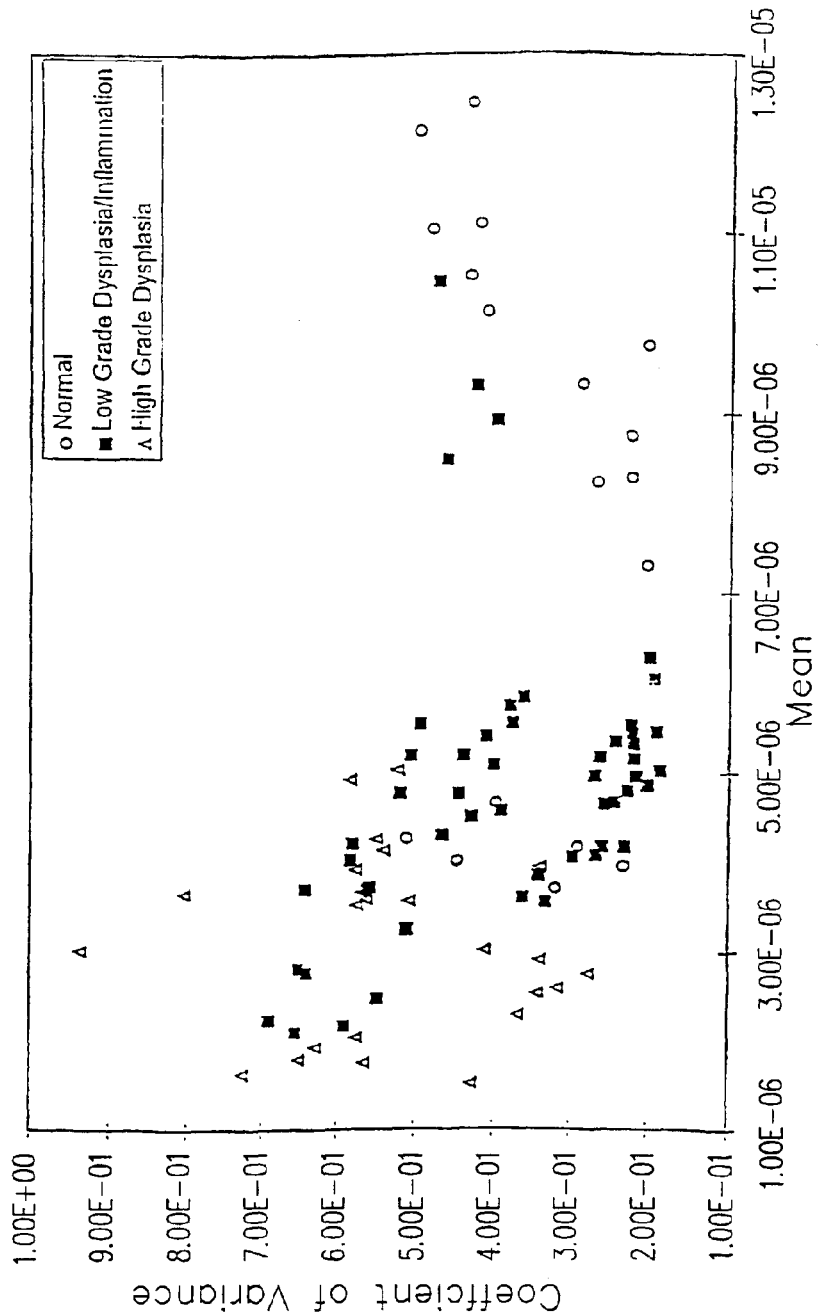
Figure 45:
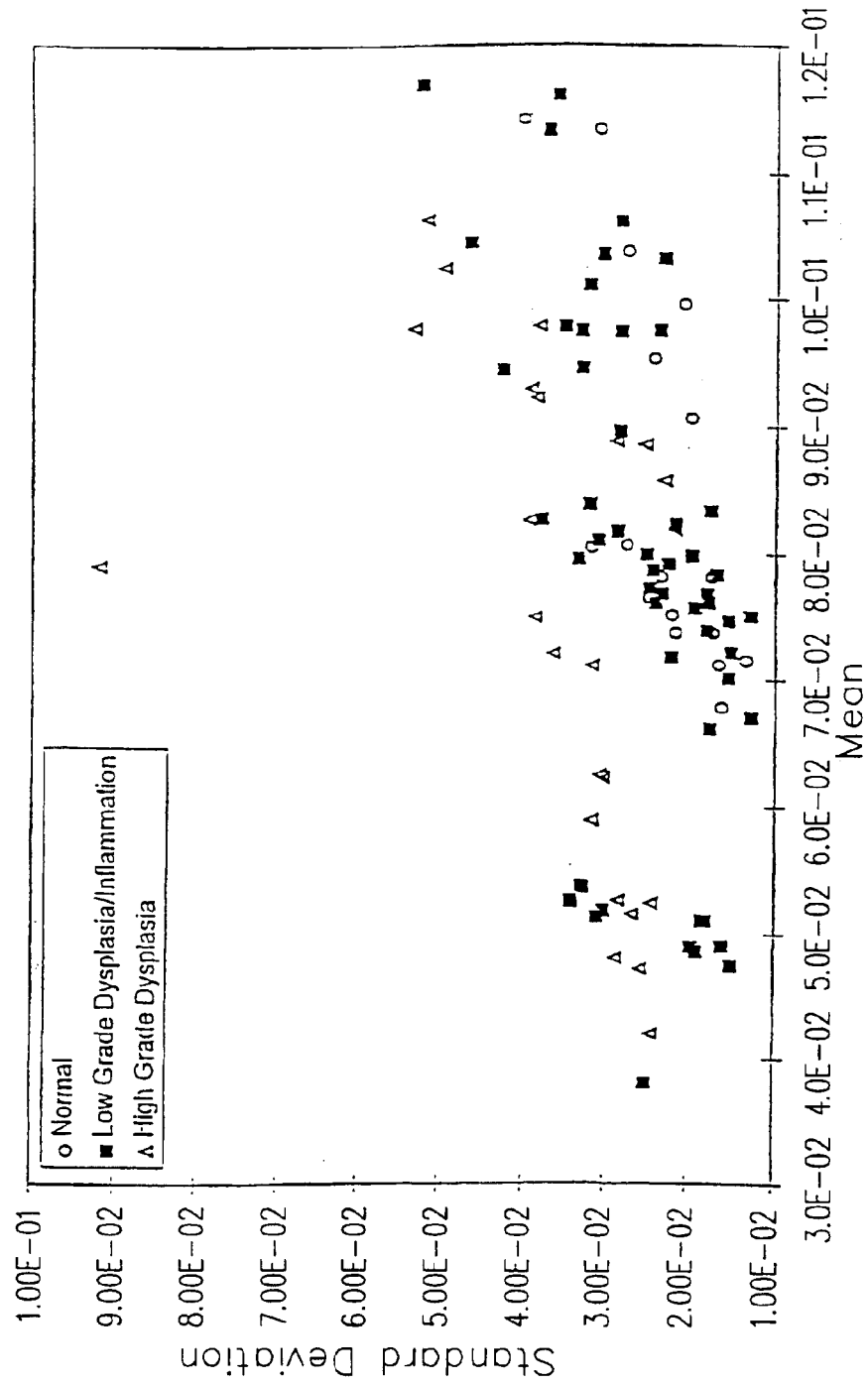
Figure 46:
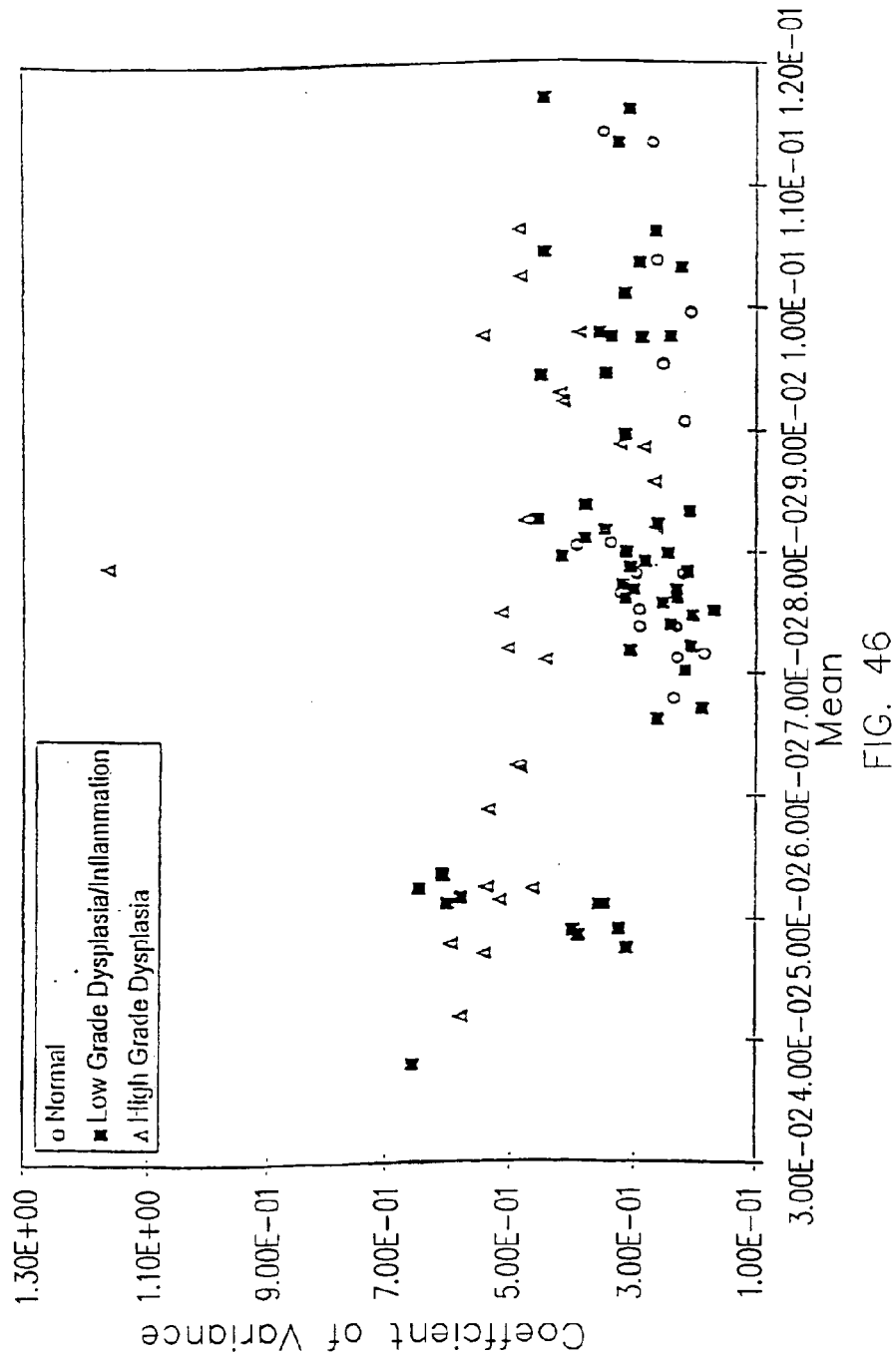
Figure 47:
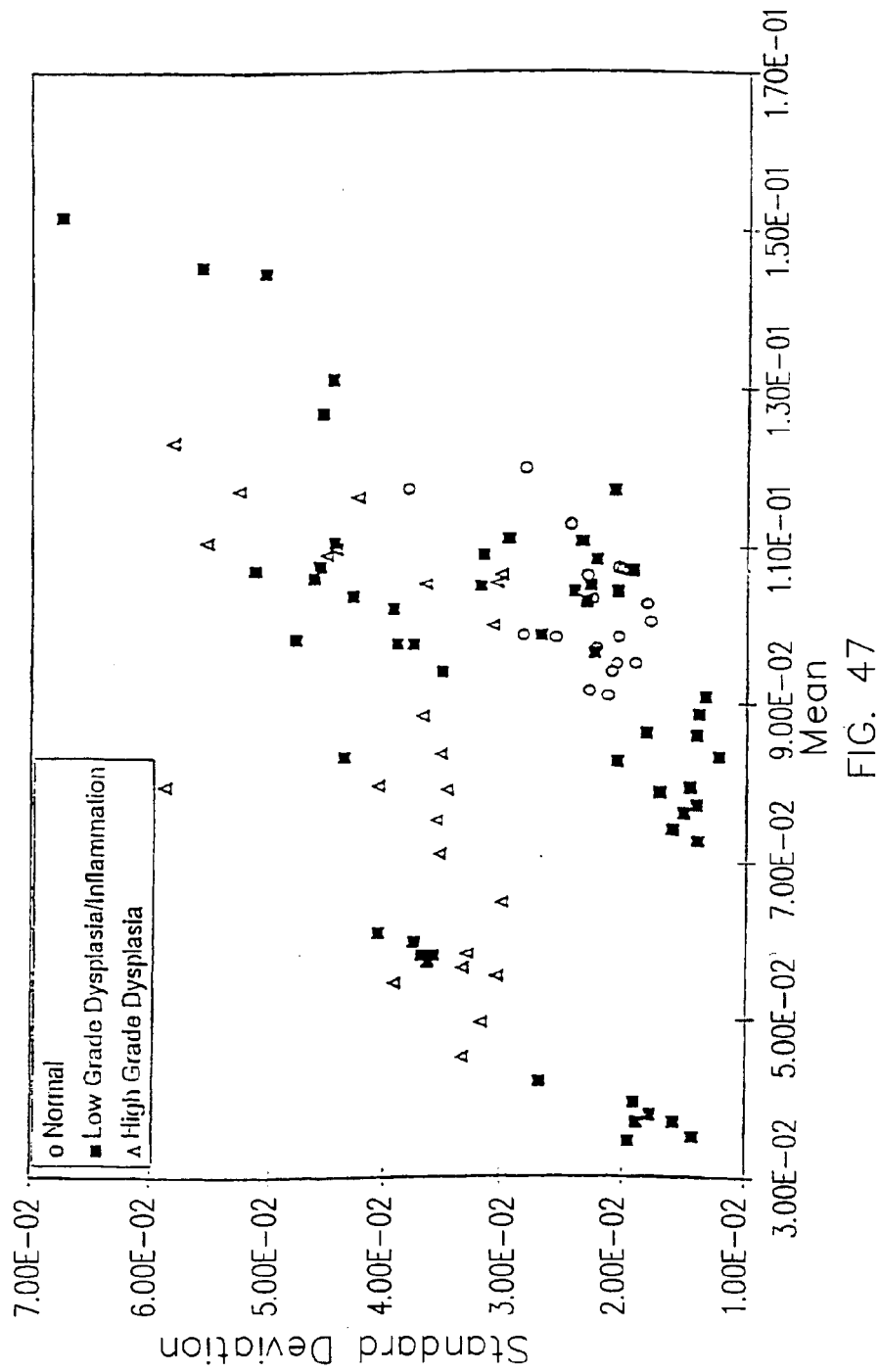
Figure 48:
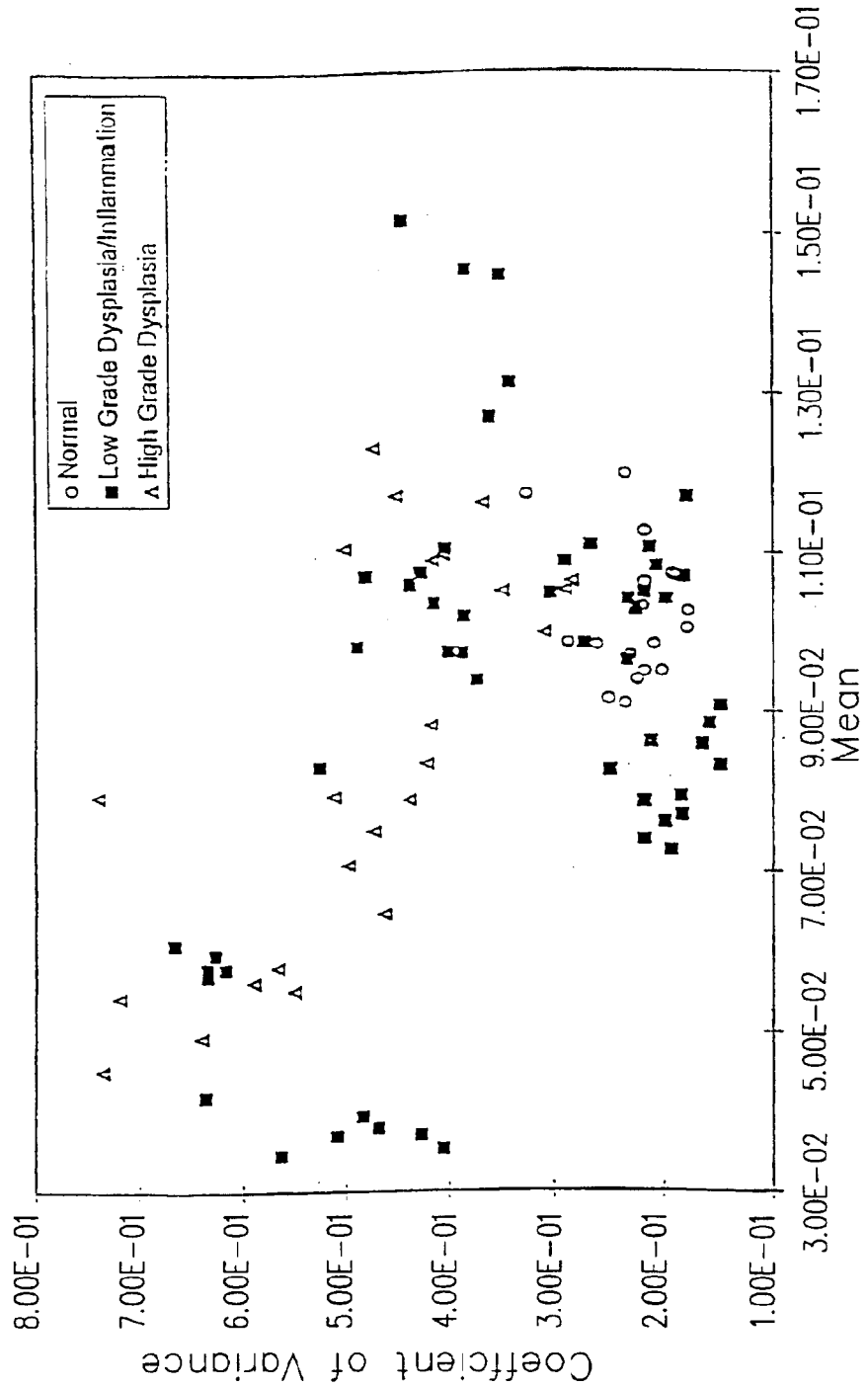
Figure 49:
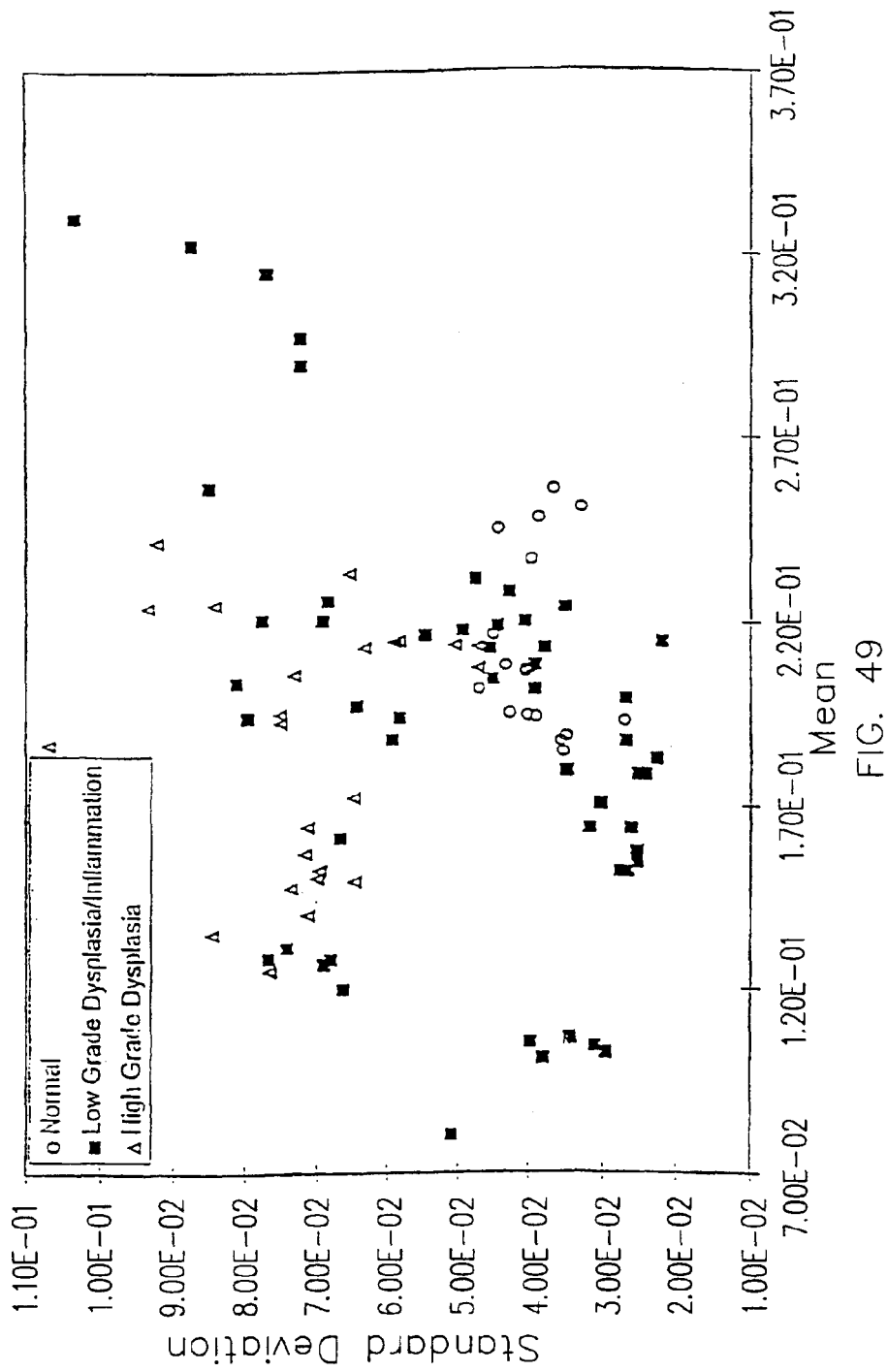
Figure 50:
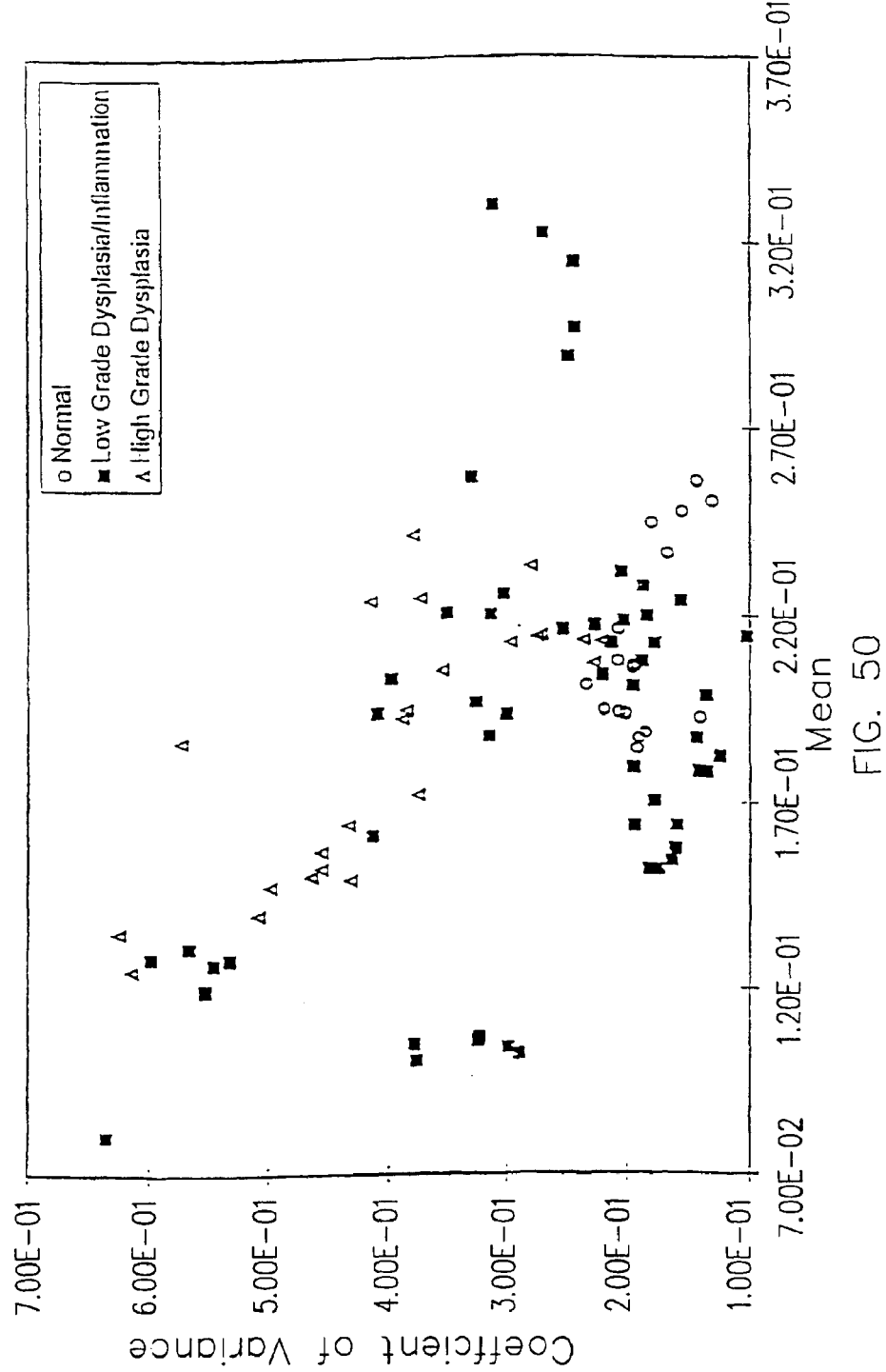

FIGS. 13 and 14 show biparameter plots of the means versus the coefficient of variance (CV) and standard deviation (SD), respectively, for all twenty-one cases. The first five cases were standardized to take into account the differences in window type between these and the other sixteen cases. In FIG. 13, the six high grade/cancer cases appear to be clustered in the upper right hand corner of the graph (above the diagonal line and to the right of the three low grade lesions above the line).

The remaining analyses involved the latter sixteen patients tested with the second generation probe and new monochrometer. FIGS. 15–26 show the calculated values for the whole cervix. Table 2 below summarizes the degree of overlap between high grade cases and low grade/inflammation/normal cases for each of the three fluorescence and reflectance measurements, showing the percentage of correct negative predictions where n=12 using the threshold below the lowest level measure for the four high grade cases (i.e., at 100% sensitivity). Table 2 includes all sub-high grade dysplasia case, including low grade dysplasia (n=7), inflammation (n=3), abnormal Pap results but no biopsy (n=2), symptomless patient with history of disease who underwent an experimental treatment (n=2), and normals (n=1). As can be seen in Table 2, wavelengths of 290 nm for fluorescence measurements and 320 nm for reflectance measurements show the least amount of overlap between high grade and sub-high grade cases.

TABLE 2

| Variable | Mean | Standard Deviation | Coefficient of Variance |
|---|---|---|---|
| 290 FL Excitation | 58% | 75% | 75% |
| 350 FL Excitation | 42% | 17% | 58% |
| 460 FL Excitation | 67% | 0% | 33% |
| 320 Reflectance | 25% | 67% | 75% |
| 420 Reflectance | 8% | 67% | 58% |
| 540–580 Reflectance | 25% | 58% | 67% |

FIGS. 27–38 show the calculated measurements for quadrants that had a sufficiently high signal-to-noise ration, and that were subsequently analyzed to determine their condition. The objective of the by quadrant analysis was to indicate whether spatial information down to the quadrant level was available and to determine whether normal quadrants could be differentiated from abnormal quadrants.

A total of nineteen quadrants could be reliably identified as containing either a diseased or normal biopsied site. Of these, none were normal quadrants, eight contained low grade/inflammatory disease and two contained high grade disease. Use of a wavelength of 290 nm for fluorescence measurements appeared to separate the data by virtue of within quadrant measures of variability (SD and CV). Mean fluorescence appears to be discriminative at 350 and 420 nm. There appears to one high grade lesion, which was diagnosed by Pap test as normal and by colposcopy as metaplasia, which can be misdiagnosed as high grade disease at biopsy. Thus, while it was seen previously that whole cervix measurements were of little diagnostic value, when taken down to the quadrant level, i.e., a smaller field area, the measurements become more diagnosticly "meaningful".

FIGS. 39–50 show the by rotation calculated measurements. This analysis was done in order to determine whether individual rotation data, from a single measurement cycle, provided any clue as to whether all or a subset for the six rotation positions are necessary. In general, the single rotation data mirror that of the integrated data set, with a bit more overlap. Based on the results, it appears that the by-rotation data is similar to the entire cervix data. This suggests that the resolution obtained from 42 interrogation points may be sufficient to accurately predict the condition of the cervix.

Figure 51:
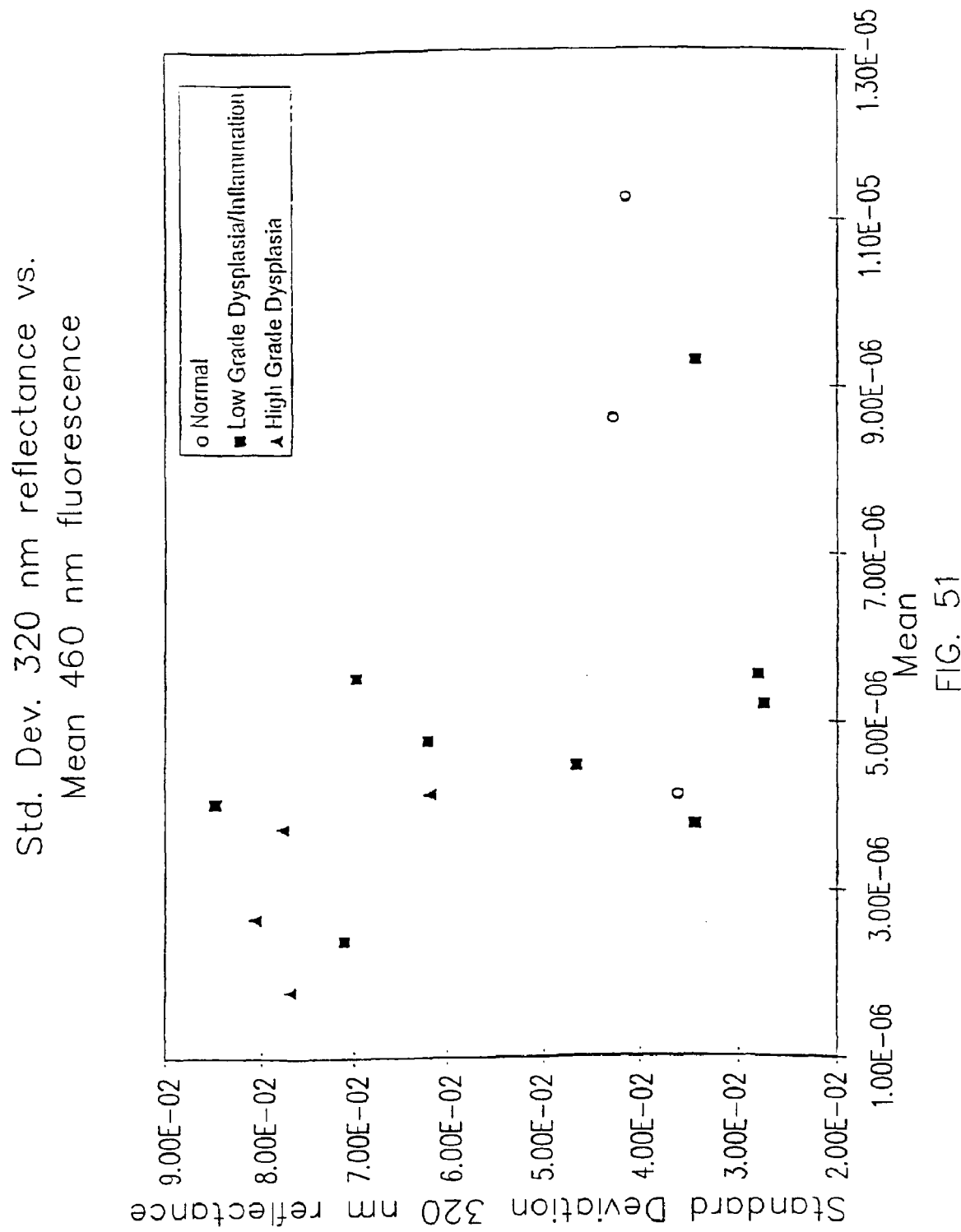

FIG. 51 shows a biparameter plot of the calculated standard deviation of the reflectance measurements using a wavelength of 320 nm against the calculated means of the fluorescence measurements using a wavelength of 460 nm. As can be seen, this plot show a differentiation between normal and high grade lesions.

Although it is premature to draw definitive conclusions regarding this small data set, the result are encouraging. There were high grade lesions misclassified by both Pap tests and colposcopy which could be discriminated by the spectroscopic methods of the invention. Moreover, the results of these preliminary cases are consistent with known biologic phenomena and field effects due to carcinogenesis. Of note is that both fluorescence and reflectance measurements provide discriminative information.

Having looked at overall means, standard deviation and coefficient of variation at individual wavelengths, spatial and spectral information can then be exploited. Those spectra measured from points on the tissue for which histopathology is available (e.g., at/near a biopsy site) can be examined specifically by category, for example, normal versus abnormal. To further utilize spectral information, the preferred method involves taking various intensity ratios at the key wavelengths discussed above. Beyond that approach, advanced statistical analysis techniques (for example, principal component analysis, Bayesian Classification, Classification Trees, Artificial Neural Networks,) may be used to help to identify other wavelengths which can be effective for discriminating and modeling a pattern recognition.

The foregoing embodiments are merely exemplary and are not to be construed as limiting the invention. The present teaching can be readily applied to other types of apparatuses. The description of the invention is intended to be illustrative, and not to limit the scope of the claims. Many alternatives, modifications, and variations will be apparent to those skilled in the art.

What is claimed is:

1. A method for diagnosing a condition of a target tissue in a human or animal, comprising:
    a.) irradiating a target tissue with excitation electromagnetic radiation;
    b.) measuring the received electromagnetic radiation using at least biochemical and morphological spectroscopic methods to generate spectroscopic measurements;
    c.) combining the at least one biochemical and one morphological measurements; and
    d.) determining a condition of the target tissue based on the combined measurements, wherein the biochemical spectroscopic method comprises at least one of fluorescence, time resolved fluorescence, or fluorescence anisotropy and the morphological spectroscopic method comprises at least one of absorption, reflectance, or polarized reflectance.

2. The method of claim 1, wherein the time resolved fluorescence comprises at least one of phase modulation techniques, polarization anisotropic techniques and techniques that directly monitor the decay profile of fluorescent emissions.

3. A method for diagnosing a condition of a target tissue, comprising:
    a.) irradiating a target tissue with excitation electromagnetic radiation;
    b.) sensing a returned electromagnetic radiation returned from the target tissue;
    c.) determining characteristics of the returned electromagnetic radiation using at least two spectroscopic methods;
    d.) combining the characteristics determined by the at least two spectroscopic methods, thereby decoupling and detecting biochemical changes and morphological changes in the target tissue; and
    e.) determining a condition of the target tissue based on the combined determined characteristics, wherein step b.) comprises sensing electromagnetic radiation emitted from the target tissue in response to the excitation electromagnetic radiation and then subsequently sensing excitation electromagnetic radiation that is scattered from the target tissue.

4. The method according to claim 3, wherein a critical timing window, which is defined as the time period between sensing electromagnetic radiation emitted from the target tissue in response to the excitation electromagnetic radiation and subsequently sensing excitation electromagnetic radiation that is scattered from the target tissue, is not greater than approximately 0.25 seconds.

5. The method of claim 3, wherein step c.) comprises making intensity based measurements on both said electromagnetic radiation emitted from the target tissue in response to the excitation electromagnetic radiation and said excitation electromagnetic radiation that is scattered from the target tissue.

6. The method of claim 1, wherein step b.) comprises sensing measuring electromagnetic radiation receive from a plurality of interleaved interrogation points distributed over the target tissue.

7. The method according to claim 1, further comprising dividing the target tissue into two or more field areas, wherein step d.) comprises determining a condition of the target tissue in each of said field areas and then further determining a condition of the target tissue by comparing each of said field areas.

8. A method for diagnosing a condition of a target tissue, comprising:
  a.) irradiating a target tissue with excitation electromagnetic radiation;
  b.) sensing a returned electromagnetic radiation returned from the target tissue;
  c.) determining characteristics of the returned electromagnetic radiation using at least two spectroscopic methods;
  d.) combining the characteristics determined by the at least two spectroscopic methods, thereby decoupling and detecting biochemical changes and morphological changes in the target tissue;
  e.) determining a condition of the target tissue based on the combined determined characteristics;
  f.) identifying visual characteristics of the target tissue; and
  g.) dividing the target tissue into a first set of field areas, wherein step c.) comprises determining characteristics of the returned electromagnetic radiation in each of said first set of field areas using at least two spectroscopic methods, step d.) comprises combining the characteristics determined by the at least two spectroscopic methods for each of said first set of field areas and step e.) comprises determining a condition of the target tissue by comparing the combined determined characteristics of each of said first set of field areas; and wherein the field areas are selected based on the identified visual characteristics of the target tissue.

9. A method for diagnosing a condition of a target tissue, comprising:
  a.) irradiating a target tissue with excitation electromagnetic radiation;
  b.) sensing a returned electromagnetic radiation returned from the target tissue;
  c.) determining characteristics of the returned electromagnetic radiation using at least two spectroscopic methods;
  d.) combining the characteristics determined by the at least two spectroscopic methods, thereby decoupling and detecting biochemical changes and morphological changes in the target tissue;
  e.) determining a condition of the target tissue based on the combined determined characteristics; and
  f.) dividing the target tissue into a first set of field areas, wherein step c.) comprises determining characteristics of the returned electromagnetic radiation in each of said first set of field areas using at least two spectroscopic methods, step d.) comprises combining the characteristics determined by the at least two spectroscopic methods for each of said first set of field areas and step e.) comprises determining a condition of the target tissue by comparing the combined determined characteristics of each of said first set of field areas, and wherein the field areas are selected based on previously identified characteristics of the target tissue.

10. The method according to claim 9, wherein the previously identified characteristics of the target tissue comprise characteristics of the target tissue identified through previous testing of the target tissue using at least one of cytology, colposcopy and histopathology.

11. A method for diagnosing a condition of a target tissue, comprising:
  a.) irradiating a target tissue with excitation electromagnetic radiation;
  b.) sensing a returned electromagnetic radiation returned from the target tissue;
  c) determining characteristics of the returned electromagnetic radiation using at least two spectroscopic methods;
  d.) combining the characteristics determined by the at least two spectroscopic methods, thereby decoupling and detecting biochemical changes and morphological changes in the target tissue;
  e.) determining a condition of the target tissue based on the combined determined characteristics;
  f.) dividing the target tissue into a first set of field areas, wherein step c.) comptises determining characteristics of the returned electromagnetic radiation in each of said first set of field areas using at least two spectroscopic methods, step d.) comprises combining the characteristics determined by the at least two spectroscopic methods for each of said first set of field areas and step e.) comprises determining a condition of the target tissue by comparing the combined determined characteristics of each of said first set of field areas; and
  g.) after determining a condition of the target tissue by comparing the combined determined characteristics of each of said first set of field areas, re-dividing the target tissue into a second set of field areas, different from said first set of field areas and the determining characteristics of the returned electromagnetic radiation in each of said second set of field areas using at least two spectroscopic methods, combining the characteristics determined by the at least two spectroscopic methods for each of said second set of field areas and determining a condition of the target tissue by comparing the combined determined characteristics of each of said second set of field areas.

12. A method for diagnosing a condition of a target tissue, comprising:
  a.) irradiating a target tissue with excitation electromagnetic radiation;
  b.) sensing a returned electromagnetic radiation returned from the target tissue;
  c.) determining characteristics of the returned electromagnetic radiation using at least two spectroscopic methods;
  d.) combining the characteristics determined by the at least two spectroscopic methods, thereby decoupling and detecting biochemical changes and morphological changes in the target tissue; and e.) determining a condition of the target tissue based on the combined determined characteristics, wherein the method is performed using an apparatus comprising an irradiation source, a detector and a processor, and wherein sensing electromagnetic radiation returned from a plurality of interrogation points comprises:

sensing electromagnetic radiation returned from the target tissue from a first subset of the plurality of interrogation points;

moving at least one of the apparatus and the tissue;

sensing electromagnetic radiation returned from the target tissue from a second subset of the plurality of interrogation points;

again moving at least one of the apparatus and the tissue; and continuing this process until sensing has been performed at all of the plurality of interrogation points.

13. The method of claim 1, further comprising generating a map of conditions of different portions of the target tissue based on the combined determined characteristics.

14. The method of claim 1, further comprising conducting a pattern recognition process to determine whether a pattern of conditions exists within the target tissue.

15. A system for determining a condition of a target tissue in a human or animal, comprising:
   a electromagnetic radiation source for irradiating tissue;
   a device that couples the electromagnetic radiation to a target tissue;
   a device that senses electromagnetic radiation received from the target tissue; and
   a processor configured to determine characteristics of the target tissue using at least one biochemical and one morphological spectroscopic methods, wherein the processor combines the characteristics determined by each of the two or more spectroscopic methods and determines a condition of the target tissue based on the combined determined characteristics, and wherein the biochemical spectroscopic method comprises at least one of fluorescence, time resolved fluorescence, or fluorescence anisotropy and the morphological spectroscopic method comprises at least one of absorption, reflectance, or polarized reflectance.

16. The system of claim 15, wherein the device that senses received electromagnetic radiation is configured to substantially simultaneously sense fluorescent radiation emitted by endogenous fluorophores in response to the excitation radiation and excitation electromagnetic radiation that is scattered from the target tissue.

17. The system of claim 16, wherein the processor uses intensity based measurements on both said fluorescent radiation emitted by endogenous fluorophores in response to the excitation radiation and said excitation electromagnetic radiation that is scattered from the target tissue.

18. A system for determining a condition of a target tissue in a human or animal, comprising:
   an electromagnetic radiation source for providing excitation electromagnetic radiation;
   a device that couples the excitation electromagnetic radiation to a target tissue;
   a device that senses electromagnetic radiation returned from the target tissue; and
   a processor configured to determine characteristics of the returned electromagnetic radiation using at least two spectroscopic methods, wherein the processor combines the characteristics determined by each of the at least two spectroscopic methods in order to decouple and detect biochemical changes and morphological changes in the target tissue and determines a condition of the target tissue based on the combined determined characteristics, wherein the device that senses electromagnetic radiation is configured to first sense fluorescent radiation emitted by fluorophores in response to the excitation radiation and then subsequently sense excitation electromagnetic radiation that is scattered from the target tissue.

19. The system according to claim 18, wherein a critical timing window, which is defined as the time period between sensing electromagnetic radiation emitted from the target tissue in response to the excitation electromagnetic radiation and subsequently sensing excitation electromagnetic radiation that is scattered from the target tissue, is not greater than approximately 0.25 seconds.

20. The system of claim 18, wherein the processor uses intensity based measurements on both said fluorescent radiation emitted by endogenous fluorophores in response to the excitation radiation and said excitation electromagnetic radiation that is scattered from the target tissue.

21. The system of claim 15, wherein the device that senses electromagnetic radiation is configured to sense substantially simultaneously electromagnetic radiation returned from a plurality of interleaved interrogation points distributed over the target tissue.

22. The system according to claim 15, wherein the processor divides the target tissue into two or more field areas, determines characteristics of the received electromagnetic radiation in each of said field areas and determines a condition of the target tissue based on comparing the determined characteristics of the respective field areas.

23. A system for determining a condition of a target tissue in a human or animal, comprising:
   a electromagnetic radiation source for providing excitation electromagnetic radiation;
   a device that couples the excitation electromagnetic radiation to a target tissue;
   a device that senses electromagnetic radiation returned from the target tissue; and
   a processor configured to determine characteristics of the returned electromagnetic radiation using at least two spectroscopic methods, wherein the processor combines the characteristics determined by each of the at least two spectroscopic methods in order to decouple and detect biochemical changes and morphological changes in the target tissue and determines a condition of the target tissue based on the combined determined characteristics, wherein the processor divides the target tissue into a first set of field areas, determines characteristics of the returned electromagnetic radiation in each of said first set of field areas using said at least two spectroscopic methods, combines the characteristics determined by each of said at least two spectroscopic methods for each of said first set of field areas and determines a condition of the target tissue in each of said first set of field areas based on the combined determined characteristics of the respective field areas, and wherein the target tissue is divided into field areas according to previously identified characteristics of the target tissue.

24. The system according to claim 23, wherein the previously identified characteristics of the target tissue are visually identified characteristics of the target tissue.

25. The system according to claim 23, wherein the previously identified characteristics of the target tissue are characteristics of the target tissue identified through previous testing of the target tissue using at least one of cytology, colposcopy and histopathology.

26. A system for determining a condition of a target tissue in a human or animal, comprising:
    an electromagnetic radiation source for providing excitation electromagnetic radiation;
    a device that couples the excitation electromagnetic radiation to a target tissue;
    a device that senses electromagnetic radiation returned from the target tissue; and
    a processor configured to determine characteristics of the returned electromagnetic radiation using at least two spectroscopic methods, wherein the processor combines the characteristics determined by each of the at least two spectroscopic methods in order to decouple and detect biochemical changes and morphological changes in the target tissue and determines a condition of the target tissue based on the combined determined characteristics, wherein the processor divides the target tissue into a first set of field areas, determines characteristics of the returned electromagnetic radiation in each of said first set of field areas using said at least two spectroscopic methods, combines the characteristics determined by each of said at least two spectroscopic methods for each of said first set of field areas and determines a condition of the target tissue in each of said first set of field areas based on the combined determined characteristics of the respective field areas, and wherein the processor is further configured to, after the processor determines a condition of the target tissue in each of the first set of field areas based on the combined determined characteristics of the respective field areas, divide the target tissue into a second set of field areas, different from the first set of field areas, determine characteristics of the returned electromagnetic radiation in each of said second set of field areas using said at least two spectroscopic methods, combine the characteristics determined by each of said at least two spectroscopic methods for each of said second set of field areas and determine a condition of the target tissue in each of the second set of field areas based on the combined determined characteristics of the respective field areas.

27. The system of claim 21, wherein the device that senses electromagnetic radiation is movable to a plurality of pre-determined positions and is configured to sense electromagnetic radiation returned from a subset of the plurality of interrogation points at each pre-determined position.

28. The system of claim 15, wherein the processor is also configured to conduct a pattern recognition process to determine whether a pattern of conditions exists within the target tissue.

29. The system of claim 15, wherein the processor is also configured to create a map of determined conditions of different portions of a target tissue.

30. A method for diagnosing diseased tissue in a human or animal, comprising:
    irradiating a target tissue with excitation electromagnetic radiation;
    sensing an electromagnetic radiation received from the target tissue;
    determining characteristics of the received electromagnetic radiation using at least first and second spectroscopic methods, thereby decoupling and detecting biochemical changes and morphological changes in the target tissue occurring due to disease; and
    determining a condition of the target tissue based the determined characteristics, wherein the first spectroscopic method comprises at least one of fluorescence, time resolved fluorescence, or fluorescence anisotropy and the second spectroscopic method comprises at least one of absorption, reflectance, or polarized reflectance.

31. A system for determining a condition of a target tissue in a human or animal, comprising:
    an electromagnetic radiation source for providing excitation electromagnetic radiation;
    a device that couples the excitation electromagnetic radiation to a target tissue;
    a device that senses electromagnetic radiation received from the target tissue; and
    a processor configured to determine characteristics of the received electromagnetic radiation using at least first and second spectroscopic methods, thereby decoupling and detecting biochemical changes and morphological changes in the target tissue occurring due to disease and determine a condition of the target tissue based on the determined characteristics, wherein the first spectroscopic method comprises at least one of fluorescence, time resolved fluorescence or fluorescence anisotropy and the second spectroscopic method comprises at least one of absorption, reflectance, or polarized reflectance.

32. An endoscope configured to perform the method of claim 12, wherein the endoscope is further configured to sense electromagnetic radiation received from the plurality of interrogation points within a critical timing window.

33. An endoscope comprising the system of claim 15, wherein the endoscope is further configured to sense electromagnetic radiation received from a plurality of interrogation points within a critical timing window.

34. An endoscope comprising the system of claim 21, wherein the endoscope is further configured to sense electromagnetic radiation received from the plurality of interleaved interrogation points within a critical timing window.

35. The method of claim 6, wherein the plurality of interleaved interrogation points are spaced so as to minimize crosstalk between the plurality of interrogation points while preserving spatial resolution.

36. The method of claim 21, wherein the plurality of interleaved interrogation points are spaced so as to minimize crosstalk between the plurality of interrogation points while preserving spatial resolution.

37. The method according to claim 1, further comprising comparing the combined measurements to reference measurements made on tissue of the same human or animal.

38. The method according to claim 15, wherein the processor is further configured to compare the combined measurements to reference measurements made on tissue of the same human or animal.

39. The method according to claim 1, wherein the method is configured to detect changes in a target tissue due to cancer.

40. The system according to claim 15, wherein the system is configured to detect changes in a target tissue due to cancer.

41. The method according to claim 30, wherein the method is configured to detect changes in a target tissue due to cancer.

42. The method according to claim 7, wherein variability of the field areas is used to determine a characteristic of the tissue.

43. The method according to claim 1, wherein step b.) comprises measuring electromagnetic radiation received from a first set of interrogation points and then sensing electromagnetic radiation returned from a second set of interrogation points interleaved with the first set of interrogation points.

44. The method according to claim 1, wherein determining the condition of the target tissue includes the assignment of a score related to the condition of the tissue.

45. The method of claim 6, wherein each group of one or more interrogation points is assigned a score related to the condition of the tissue.

* * * * *